(12) United States Patent
Inman et al.

(10) Patent No.: US 7,528,274 B2
(45) Date of Patent: May 5, 2009

(54) ACYLTHIOLS AND COMPONENT THIOL COMPOSITIONS AS ANTI-HIV AND ANTI-RETROVIRAL AGENTS

(75) Inventors: John K. Inman, Bethesda, MD (US); Atul Goel, Lucknow (IN); Ettore Appella, Chevy Chase, MD (US); Jim Turpin, Frederick, MD (US); Marco Schito, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 45 days.

(21) Appl. No.: 10/485,165

(22) PCT Filed: Jul. 25, 2002

(86) PCT No.: PCT/US02/23924

§ 371 (c)(1), (2), (4) Date: Aug. 26, 2004

(87) PCT Pub. No.: WO03/014062

PCT Pub. Date: Feb. 20, 2003

(65) Prior Publication Data

US 2005/0020831 A1    Jan. 27, 2005

Related U.S. Application Data

(60) Provisional application No. 60/310,133, filed on Aug. 3, 2001.

(51) Int. Cl.
*C07C 327/16*    (2006.01)
*A61K 31/21*    (2006.01)

(52) U.S. Cl. .......................... 558/256; 558/257; 549/70; 549/71; 549/484; 546/313; 514/354; 514/355; 514/448; 514/461; 514/513

(58) Field of Classification Search .................. 558/256, 558/257; 514/513, 354, 355, 448, 461; 546/313; 549/70, 71, 484
See application file for complete search history.

(56) References Cited

U.S. PATENT DOCUMENTS 2,850,491 A    9/1958    Brenner
4,560,506 A    12/1985    Weller, III et al.

FOREIGN PATENT DOCUMENTS

WO    WO 99/65871 A2    12/1999
WO    WO 03/060098 A2    7/2003

OTHER PUBLICATIONS

Goel, A., et al., "Benzamide—Based Thiolcarbamates: A New Class of HIV-1 NCp7 Inhibitors," Bioorganic & Medicinal Chemistry Letters, 2002, vol. 12, pp. 767-770.
Song, Y., et al., "Synthesis and Biological Properties of Amino Acid Amide Ligand-Based Pyridinioalkanoyl Thioesters as Anti-HIV Agents," Bioorganic & Medicinal Chemistry, 2002, vol. 10, pp. 1263-1273.
Turpin, et al., "Synthesis and Biological Properties of Novel Pyridinioalkanoyl Thiolesters (PATE) as Anti-HIV-1 Agents That Target the Viral Nucleocapsid Protein Zinc Fingers", *J. Med. Chem.* (1999) 42:67-86.

*Primary Examiner*—Shailendra Kumar
(74) *Attorney, Agent, or Firm*—Townsend and Townsend and Crew LLP

(57) ABSTRACT

Certain thiol and acylthiol compounds inhibit retrovirus growth by attacking the highly conserved zinc finger regions of essential viral proteins. These compounds, compositions containing them, and methods of using them to treat retroviral infections such as HIV are described. These compounds are also useful for preparation of vaccines comprised of inactivated retroviruses such as HIV, prevention of the transmission of such retroviruses, and detection of retroviral proteins.

26 Claims, 24 Drawing Sheets

1  3  5

8  9  10

11  12

13　　　　　　　　14　　　　　　　　15

17　　　　　　　　18

19　　　　　　　　20　　　　　　　　21

22　　　　　　　　23　　　　　　　　24

25

26

27

28

29

30

31

33

34

35

37
 38
 39

40
 41
 42

43
 44
 45

46
 47
 48

49      50      51

52      53      54

55      56

57      59

61

62

63

64

66

67

68

69

70

72

73

74

77

78

85

86

87

88

89

95

96

97

98

99

100

101

102

103

104

117

118

119

120

121

122

123

124

125

126

127

128

129

130

131

132

133

134

135

136

137

138

139

140

141

142

188   189   190

191   192   193

194   195   201

207

208

209

210

212

213

214

215

216

217

218

219

220

221

222

223

224

225

226

227

228

229

230

231

232

ACYLTHIOLS AND COMPONENT THIOL COMPOSITIONS AS ANTI-HIV AND ANTI-RETROVIRAL AGENTS

CROSS-REFERENCES TO RELATED APPLICATIONS

This application is a 371 PCT/US02/23924, filed Jul. 25, 2002, and claims priority to U.S. Provisional Application No. 60/310,133, filed Aug. 3, 2001.

STATEMENT AS TO RIGHTS TO INVENTIONS MADE UNDER FEDERALLY SPONSORED RESEARCH OR DEVELOPMENT

Not Applicable

BACKGROUND OF THE INVENTION

Viruses, especially the hyper-mutable retroviruses such as HIV, can rapidly become resistant to drugs used to treat the infection. This extreme mutability has allowed HIV to diverge into two major species, HIV-1 and HIV-2, each of which has many types, subtypes and drug-resistant variations.

Strategies for coping with the emergence of viral drug-resistant strains include combination drug therapies (see, e.g., Lange (1996) AIDS 10 Supplement 1:S27-S30). Drugs against different viral proteins and drugs against multiple sites on the same protein are commonly used as a strategy to overcome the adaptability of the virus. Combination therapies for retroviruses, using, e.g. protease inhibitors and nucleoside analogues, such as AZT, ddI, ddC and d4T, can become ineffectual. The virus can develop a complete resistance to the drugs in a relatively short period of time (see, e.g., Birch (1998) AIDS 12:680-681; Roberts (1998) AIDS 12:453-460; Yang (1997) Leukemia 11 Supplement 3:89-92; Demeter (1997) J. Acquir. Immune Defic. Syndr. Hum. Retrovirol. 14(2):136-144; Kuritzkes (1996) AIDS 10 Supplement 5:S27-S31). Furthermore, although recent advances in testing HIV-SIV vaccine strategies in monkeys have been reported (see, e.g., Amara et al, (2001) Science 291:1879-1881), no antiretroviral vaccine with proven effectiveness is currently available for use in humans (see, e.g., Haynes (2001) Immunol. Res. 22:263-269; Bolognesi (1998) Nature 391:638-639; Bangham (1997) Lancet 350:1617-1621).

The HIV-1-caused AIDS epidemic began about 20 years ago. As of December 2000, the total number of cases of HIV infection and AIDS since the start of the epidemic was estimated to be around 58 million worldwide, which includes 22 million deaths and 36 million people living with HIV/AIDS (UNAIDS-WHO Internet report). Thus, there exists a great need for compounds that are more effective against retroviruses such as HIV-1, especially against varieties of HIV that have developed resistance to current treatments.

A "zinc finger" motif is a highly conserved and essential structure found in many viruses, including retroviruses such as HIV. For example, Gag and Gag-Pol proteins in the Retroviridae, except for Spumaviruses, contain a highly conserved zinc finger motif (Cysteine-Cysteine-Histidine-Cysteine: CCHC) within the nucleocapsid p7 (NCp7) protein portion of the polyprotein (see definitions below). Mutations of the chelating residues in the zinc fingers yield a non-infectious virus. The absolute conservation of the metal chelating cysteine and histidine residues along with other residues of the protein, and the participation of NCp7 in essential functions during early and late phases of virus replication, identifies this feature as a particularly appealing antiviral target for hyper-mutable retroviruses, including HIV. Because these zinc fingers are identical in most retroviruses, drugs targeting zinc fingers could provide broad spectrum antivirals that would greatly reduce resistance issues.

Various C-nitroso compounds, disulfide-containing compounds and azoic compounds, such as cystamine, thiamine disulfide, disulfiram and azodicarbonamide (ADA) can oxidize zinc finger cysteine thiolates and induce intra- and intermolecular disulfide cross-linking (see, e.g., McDonnell (1997) J. Med. Chem. 40:1969-1976; Rice (1997) Nature Medicine 3:341-345; Rice (1997) Antimicrob. Agents and Chemotherapy 41: 419-426; Rice (1996) J Med. Chem. 39:3606-3616; Rice (1996) Science 270:1194-1197; Rice (1993) Proc. Natl. Acad. Sci. USA 90:9721-9724; Rice (1993) Nature 361:473-475; Henderson, et al. WO 96/09406; Vandevelde (1996) AIDS Res. Hum. Retroviruses 12:567-568). Cysteine thiols in each of the two zinc fingers of HIV are rapidly attacked by reagents such as $Cu^{2+}$, $Fe^{3+}$, C-nitroso compounds, disulfides maleimides, alpha-halogenated ketones and nitric oxide derivatives, with simultaneous loss of the native protein structure. For example, treatment of intact HIV-1 with an oxidizing agent, such as 3-nitrosobenzamide, a C-nitroso compound, induces disulfide linkage of the nucleocapsid protein and inactivates viral infectivity through oxidation of the zinc fingers (Rice (1993) Nature 361:473; Rice (1993) Proc. Natl. Acad. Sci. USA 90:9721-9724). C-nitroso compounds can also inactivate eukaryotic CCHC zinc finger containing poly(ADP-ribose) polymerase (Buki (1991) FEBS Letters 290:181). However, these compounds tend to be toxic, have poor solubility and bioavailability, and are quickly reduced and inactivated in biological solutions.

It has recently been shown that certain compounds containing acylthio groups interact with the NCp7 zinc fingers via their acylthiol moiety. This interaction involves an acyl transfer from the acylthiol to a target cysteine sulfur atom and does not require an oxidation step as with the above-mentioned compounds (Turpin et al. (1999) J. Med. Chem. 42:67-86; Basrur et al. (2000) J. Biol. Chem. 275:14890-14897). Various members of this class of acylthiol compounds frequently exhibited acceptable antiviral potency. Pyridinioalkanoyl thioesters (PATEs) exhibited superior anti-HIV-1 activity with minimal cellular toxicity and showed appreciable water solubility. PATEs were shown to preferentially target the NCp7 C-terminal zinc finger when tested against other molecular targets. These compounds thus possessed broad spectrum antiviral activity, particularly against retroviruses such as HIV.

Despite the promising activity of the PATE compounds, the compounds of the present invention provide a significant advance in the treatment of viral infections. The PATE compounds are charged species, and as such they are quite hygroscopic. This makes isolation and purification difficult. More importantly, it increases hydrophilicity so much that uptake is inhibited and excretion is accelerated. As a result, those compounds have poor delivery characteristics for oral administration. Furthermore, many compounds of the present invention show improved hydrolytic stability in test systems containing serum, which are used to estimate the in vivo lifetime of compounds to be evaluated as drug candidates.

The compounds of the present invention possess broad spectrum antiviral activity like the PATEs. However, the acylthiols and thiols of the present invention are generally neutral species at physiological pH, so they provide better delivery characteristics than the PATE compounds. The acylthiol compounds of the present invention have increased in vivo stability, which allows more efficient delivery of the active acylthiol species to the targeted zinc finger viral proteins. Compounds of the present invention also possess other advantages, such as greater in vivo stability and greater ease of synthesis, isolation, purification, and storage, which make them still more advantageous relative to the PATEs. The compounds of the present invention are thus useful for the prevention and treatment of retroviral infections, for the preparation of inactivated viruses, and for the detection and production of antibodies to inactivated viral proteins.

The compounds of the present invention, by virtue of their antiviral activity, are also useful for the manufacture of compositions that can be used to inactivate viruses in vitro or in vivo. These compositions can be used to inactivate viruses to prevent the transmission of a viral infection, to treat a viral infection, or to prepare an inactivated virus as, for example, to prepare a vaccine. They are especially useful for the manufacture of medicaments that can be used to treat mammals infected with viral diseases, particularly retroviral diseases such as, for example, HIV.

SUMMARY OF THE INVENTION

The invention provides compounds, compositions containing such compounds, and methods for using such compounds and compositions for the treatment of viral infections, particularly those caused by retroviruses. These compounds and compositions are also useful to inhibit the transmission of such viruses, to inactivate such viruses on surfaces or in biological tissues or samples, and to detect the presence of zinc finger proteins derived from such viruses.

As such, in one embodiment, the present invention provides compounds of formula (I):

K—J—Q—NR$^1$R$^2$ (I)

wherein K is selected from the group consisting of K$^1$, K$^2$ and K$^3$:

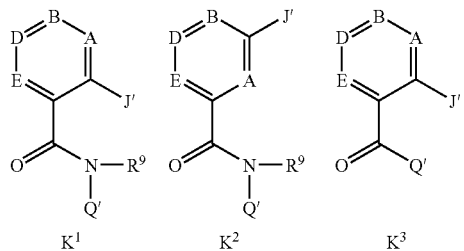

In these structures, A, B, D, and E are each independently CH, N, CR$^5$, CR$^6$, CR$^7$ or CR$^8$, with the proviso that not more than two of A, B, D, and E are nitrogen atoms. J' and Q' designate the attachment points for groups J and Q, respectively, which are described below. Thus K can be a benzamide or a pyridinyl carboxamide, and in either case, it bears a sulfur-containing substituent J that is attached either ortho or meta to the carboxamide group.

The substituents R$^5$, R$^6$, R$^7$ and R$^8$ are independently selected from the group consisting of halogen, CF$_3$, optionally substituted alkyl, optionally substituted alkoxy, optionally substituted aryl, NO$_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido.

In formula (I), J represents a thiol or acylthiol group having the structure (CH$_2$)$_m$—SH, (CH$_2$)$_m$—S—C(Z)—Y—R$^3$, or

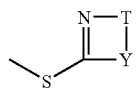

where m is an integer from 0 to 2, and Z is an oxygen atom, sulfur atom, or optionally substituted nitrogen atom (NR$^4$). Y represents a bond, an oxygen atom, a sulfur atom, or an optionally substituted nitrogen atom (NR$^4$). T is an optionally substituted alkylene of up to about 6 carbons, which allows formation of rings containing up to about eight atoms.

R$^3$ in formula (I) is an optionally substituted alkyl, optionally substituted aryl, optionally substituted arylalkyl, optionally substituted cycloalkyl, or optionally substituted cycloalkylalkyl.

R$^4$ is a substituent that may be present on an optional nitrogen atom in an acylthio group. If present, it may be hydrogen, optionally substituted alkyl, optionally substituted alkoxy, optionally substituted aryl, or optionally substituted acyl.

R$^9$ is a functional group including, but not limited to, hydrogen, optionally substituted amino, optionally substituted acyl, optionally substituted aminoacyl, optionally substituted acyloxy, optionally substituted alkoxyacyl, optionally substituted aryloxyacyl, optionally substituted thioamido, hydroxy, optionally substituted alkyl, optionally substituted aryl, optionally substituted arylalkyl, optionally substituted cycloalkyl, or optionally substituted cycloalkylalkyl.

Q is a linking group that may be a bond, optionally substituted alkylene, optionally substituted alkylene-C(O), optionally substituted phenylene, optionally substituted cycloalkylene, optionally substituted alkylcycloalkylene, optionally substituted cycloalkylenealkyl, or a structure chosen from the following substructures:

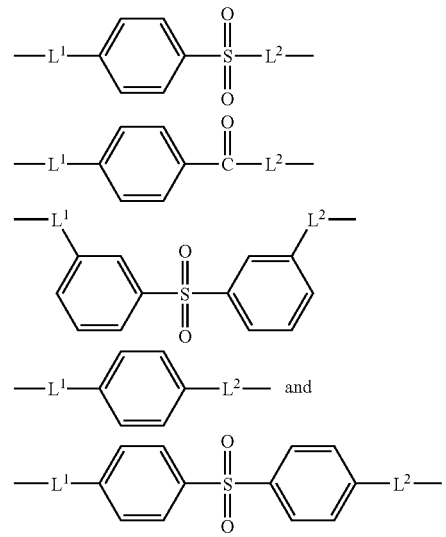

L$^1$ and L$^2$ in these substructures are independently selected, and may be a bond or an optionally substituted alkylene chain of up to 4 carbons.

R¹ is a functional group including, but not limited to, hydrogen, optionally substituted alkyl, optionally substituted aryl, optionally substituted heteroaryl, optionally substituted heteroalkyl, or optionally substituted heterocycloalkyl.

R² can be the same as R¹ or different, and is a group including, but not limited to, hydrogen, hydroxyl, amino, optionally substituted alkyl, optionally substituted aryl, optionally substituted arylalkyl, optionally substituted alkylamine, optionally substituted arylamine, optionally substituted alkoxy, optionally substituted acyl, optionally substituted aminoacyl, optionally substituted alkoxyacyl, optionally substituted alkylthioacyl, optionally substituted arylaminoacyl, optionally substituted aryloxyacyl, optionally substituted arylthioacyl, optionally substituted heteroaryl, optionally substituted heteroalkyl, optionally substituted heterocycloalkyl or optionally substituted acylamino. Alternatively, R¹ and R² can be optionally linked together to form a ring of up to about seven atoms including the N to which both are attached. This ring may be optionally substituted.

Some of the structures described above can include relatively basic groups such as amines or pyridine rings. In those embodiments, the invention also includes pharmaceutically acceptable salts of the compounds described.

In another embodiment, the present invention relates to a pharmaceutical composition including at least one compound of the present invention or a pharmaceutically acceptable salt thereof. Such compositions may optionally include a second anti-retroviral compound such as, for example, a protease inhibitor, a reverse transcriptase inhibitor, an integrase inhibitor, a fusion inhibitor and an attachment inhibitor.

In yet another embodiment of the present invention, methods are provided for treating or preventing viral infections using compounds of formula (I). Pharmaceutical compositions comprising at least one compound of the present invention can be administered by any known method to prevent or treat an infection caused by a virus or retrovirus that is sensitive to the compounds of the present invention. For example, the compound can be administered topically, as to a mucosal surface, e.g., intra-vaginally or intra-rectally, or, as an inhalant, to inhibit the transmission of a virus. Alternatively, the compositions can be administered parenterally (including intravenously), intrathecally, subcutaneously, orally and the like.

In alternative aspects, compositions comprising at least one compound of the present invention are administered to a human as a pharmaceutical formulation, or to an animal as a veterinary pharmaceutical formulation.

In one aspect, these compositions further comprise a second antiviral agent. The second antiviral agent can be another compound of the present invention, but is preferably a different type of antiviral agent, such as a reverse transcriptase inhibitor, an integrase inhibitor, a fusion inhibitor or a protease inhibitor. The nucleoside analogue can be an AZT, a ddCTP or a ddI, for example, and the fusion inhibitor can be T-20, for example.

Because of their antiviral activity, in one embodiment of the present invention, the compounds of the present invention are useful for the manufacture of medicaments. These medicaments include formulations and compositions useful for the treatment of viral diseases affecting mammals, including humans. These medicaments are also useful for inhibiting the transmission of viral diseases from one mammal to another.

In another embodiment, the present invention provides methods for dissociating a metal ion from a zinc finger-containing protein, the method comprising the step of contacting the zinc finger with a compound of the present invention. In one aspect, the zinc finger is part of a viral protein, such as a nucleocapsid protein, a Gag protein or a Gag-Pol protein. The invention also provides methods for dissociating a metal ion from a zinc finger-containing protein on an intact virus (e.g., viral particle, virion). The contacting of the virus or viral protein with the compound can be performed in vitro or in vivo. In one aspect, the zinc finger comprises a retroviral protein, e.g., a virus from an avian sarcoma retroviral group, a mammalian B-type retroviral group, a human T cell leukemia retroviral group, a bovine leukemia retroviral group, a D-type retroviral group, a murine leukemia-related group or a lentivirus group. The retroviral protein can be derived from an HIV-1, an HIV-2, an SIV, a BIV, an EIAV, a Visna, a CaEV, an HTLV-1, a BLV, an MPMV, an MMTV, an RSV, an MuLV, a FeLV, a BaEV or an SSV retrovirus.

In yet another embodiment, the invention provides a method for detecting the presence of a zinc finger-containing protein, comprising the steps of contacting the zinc finger-containing protein with a compound of the present invention to dissociate a metal ion, usually zinc, and detecting the metal ion or detecting a change caused by its dissociation. In one aspect, detecting the dissociation of the metal ion from the zinc finger can be carried out using a method such as, for example, capillary electrophoresis, immunoblotting, nuclear magnetic resonance (NMR), high performance liquid chromatography (HPLC), detecting release of radioactive zinc-65, detecting fluorescence or detecting a gel mobility shift.

The invention further provides a method for inactivating a virus, the method comprising contacting a virus with an effective amount of a composition comprising at least one compound of the present invention, wherein contacting the virus with the compound inactivates the virus. This inactivation can be partial (e.g., an attenuation) or complete. In one aspect, the compound of the present invention dissociates a zinc ion from a polypeptide, e.g., a zinc finger. The virus can be a retrovirus derived from an avian sarcoma or leukosis retroviral group, a mammalian B-type retroviral group, a human T cell leukemia or bovine leukemia retroviral group, a D-type retroviral group, a murine leukemia-related group or a lentivirus group. The retrovirus can be an HIV-2, an SIV, a BIV, an EIAV, a Visna, a CaEV, an HTLV-1, a BLV, an MPMV, an MMTV, an RSV, an MuLV, a FeLV, a BaEV or an SSV retrovirus. The retrovirus can also be an HIV-1 retrovirus. The contacting of the virus with the compound can be performed in vivo. In one aspect, the compound is administered to inhibit the transmission of infectious virus from cell to cell or from individual to individual. In another aspect, the compound is administered to treat an existing viral infection.

In alternative aspects, the contacting of the virus with a composition comprising at least one compound of the invention is performed in vitro. The contacting of the virus with the compound or composition can be performed in or on any biological tissue, food, chemical or device, such as a blood product, blood plasma, tissue or organ for transplantation, nutrient media, protein, a pharmaceutical, a cosmetic, a sperm or oocyte preparation, cells, cell cultures, bacteria, viruses, food, drink, implant, prosthesis and the like.

The invention further provides an isolated and inactivated virus, wherein the virus is inactivated by a method comprising contacting the virus with a compound of the present invention, wherein contacting the virus with the compound inactivates the virus. The invention provides a vaccine formulation comprising an inactivated virus of the present invention. The inactivated virus can be a retrovirus, e.g., an avian sarcoma retroviral group, a mammalian B-type retroviral group, a human T cell leukemia retroviral group, a bovine leukemia retroviral group, a D-type retroviral group, a murine leukemia-related group or a lentivirus group. The isolated and inactivated virus can be an HIV-2, an SIV, a BIV, an EIAV, a Visna, a CaEV, an HTLV-1, a BLV, an MPMV, an MMTV, an RSV, an MuLV, a FeLV, a BaEV and an SSV retrovirus. The inactivated virus can also be an HIV-1.

In certain aspects, the invention provides a method of selecting a compound capable of dissociating a metal ion chelated with a zinc finger of a viral protein, the method comprising: (a) contacting the zinc finger with a compound of the present invention; and (b) detecting the dissociation of the metal ion from the zinc finger of the viral protein. The metal ion can be a zinc ion. The step of detecting the dissociation of the metal ion from the zinc finger can be carried out using a variety of analytical methods such as capillary electrophoresis, immune-blotting, nuclear magnetic resonance (NMR), high performance liquid chromatography (HPLC), detecting release of radioactive zinc-65, detecting fluorescence, detecting gel mobility shift, or combinations of such methods.

In yet another embodiment, the present invention provides a kit for selecting a compound capable of dissociating a metal ion from a zinc finger of a protein, e.g., a viral protein, the kit comprising the protein, e.g., a retroviral protein, and instructions for detecting the dissociation of the metal ion from the viral protein, the instructions comprising directions for the selection of a compound of the present invention. In one aspect, a zinc ion is chelated with the zinc finger of the viral protein. In one aspect, the viral protein is incorporated in an intact virus, e.g., a retrovirus. The zinc finger can be derived from a virus, such as an avian sarcoma retroviral group, a mammalian B-type retroviral group, a human T cell leukemia retroviral group, a bovine leukemia retroviral group, a D-type retroviral group, a murine leukemia-related group or a lentivirus group. The zinc finger can be derived from a virus, e.g., an HIV-2, an SIV, a BIV, an EIAV, a Visna, a CaEV, an HTLV-1, a BLV, an MPMV, an MMTV, an RSV, an MuLV, a FeLV, a BaEV, or an SSV retrovirus. The zinc finger can also be derived from an HIV-1 virus. In alternative aspects of the kit of the present invention, the instructions are directed to detecting the dissociation of the metal ion from the protein using capillary electrophoresis, immune-blotting, nuclear magnetic resonance (NMR), high performance liquid chromatography (HPLC), detecting release of radioactive zinc-65, detecting fluorescence or detecting a gel mobility shift. The kit can also be used for the detection of the presence of a zinc finger-containing viral protein.

The invention also provides a virucidal composition comprising a compound of the present invention. The virucidal composition can further comprise blood plasma, tissue or organs for transplantation, nutrient media, protein, a pharmaceutical, a cosmetic, a sperm or oocyte preparation, cells, cell cultures, bacteria, viruses, food, drink, implants, prostheses and the like. The present invention provides blood plasma, nutrient media, protein, a pharmaceutical, a cosmetic, a sperm or oocyte preparation, cells, cell cultures, bacteria, viruses, food, drink, implants, prostheses comprising a compound of the present invention.

The invention further provides a pharmaceutical formulation comprising a compound of the present invention. The pharmaceutical formulation can further comprise a pharmaceutically acceptable excipient, carrier, or diluent, and can also optionally include at least one additional antiviral agent.

The invention provides an array or a bead comprising a compound of the present invention.

The invention provides a kit for screening for the presence of anti-viral antibodies in a biological fluid comprising a polypeptide or a virion comprising a compound of the present invention. The invention provides a method for detecting the presence of an anti-viral antibody in a biological sample comprising the following steps: (a) providing a polypeptide or a virion comprising a compound of the present invention; (b) providing a biological sample; (c) contacting the biological sample with the polypeptide or virion of step (a); and, (d) detecting the presence of an antibody specifically bound to the polypeptide or virion, thereby detecting the presence of an anti-viral antibody in the biological sample. The biological sample can be any biological fluid, or a fluid comprising a biological material (e.g., from a biopsy sample). The biological fluid can be, e.g., a serum, tear, sputum, saliva, blood, urine, vaginal fluid, or a semen sample.

The details of one or more embodiments of the present invention are set forth in the accompanying drawings and the description below. Other features, objects, and advantages of the invention will be apparent from the description and drawings, and from the claims, and are included in the present invention. All publications, patents and patent applications cited herein are hereby expressly incorporated by reference for all purposes.

DETAILED DESCRIPTION OF THE INVENTION

Figure 1:
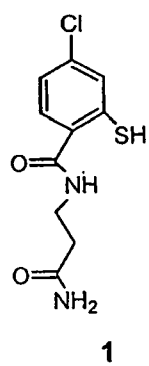
FIG. 1 depicts certain compounds of the present invention. Compound numbers in Table 1 and Table 2 herein, which describe the biological activity of these compounds, refer to the compound numbers in FIG. 1.
Figure 1:
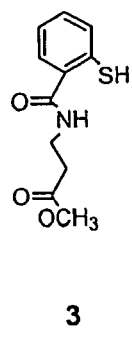
Figure 1:
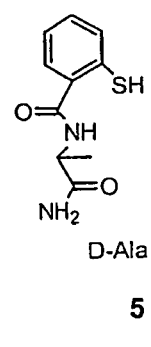
Figure 1:
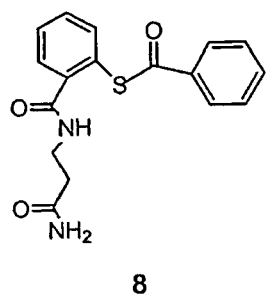
Figure 1:
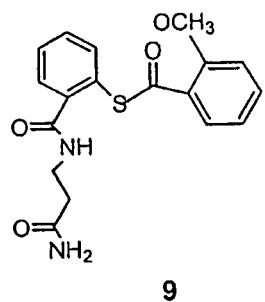
Figure 1:
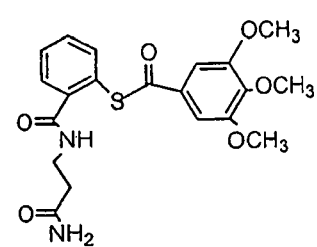
Figure 1:
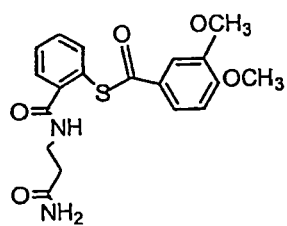
Figure 1:
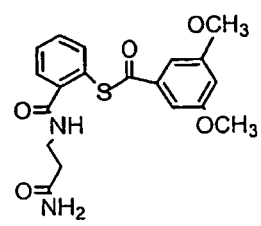
Figure 1:
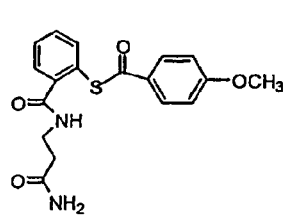
Figure 1:
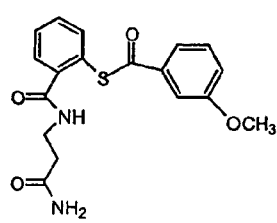
Figure 1:
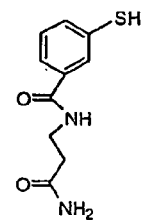
Figure 1:
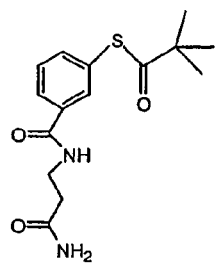
Figure 1:
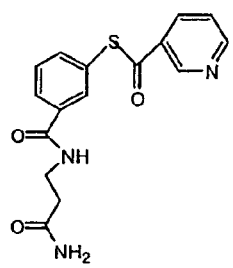
Figure 1:
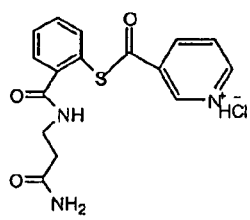
Figure 1:
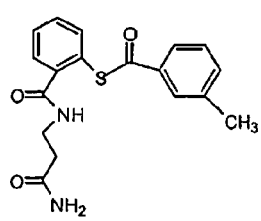
Figure 1:
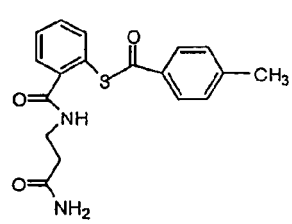
Figure 1:
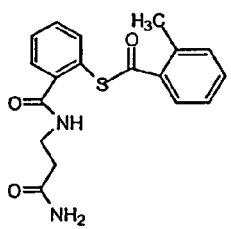
Figure 1:
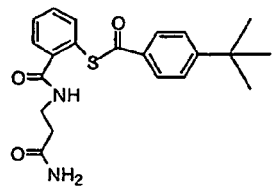
Figure 1:
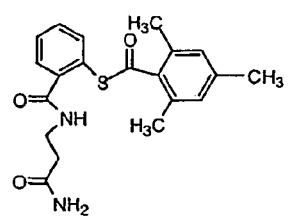
Figure 1:
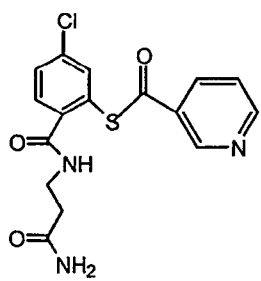
Figure 1:
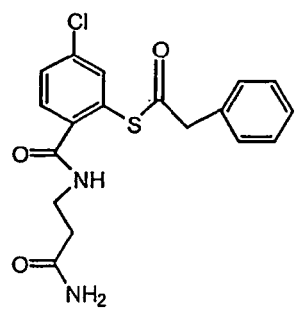
Figure 1:
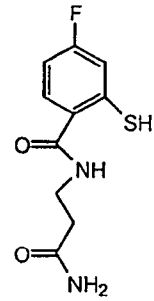
Figure 1:
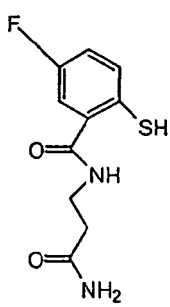
Figure 1:
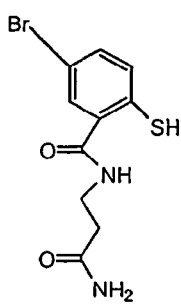
Figure 1:
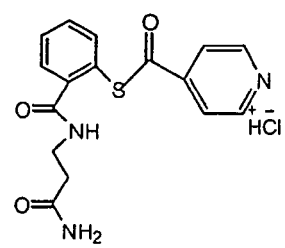
Figure 1:
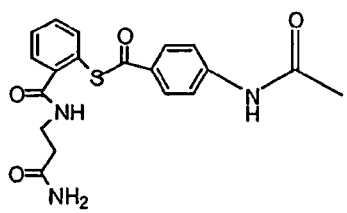
Figure 1:
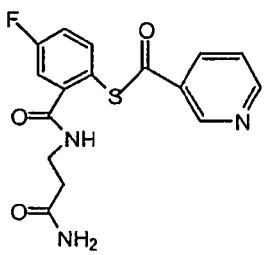
Figure 1:
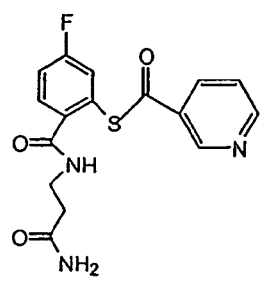
Figure 1:
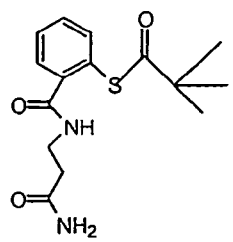
Figure 1:
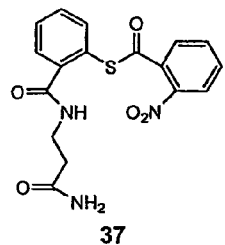
Figure 1:
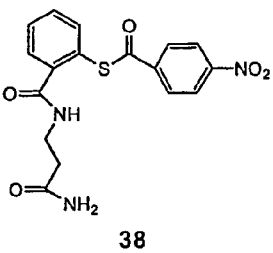
Figure 1:
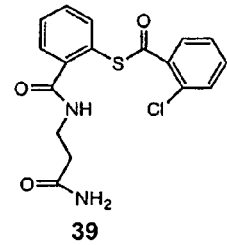
Figure 1:
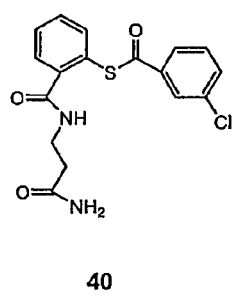
Figure 1:
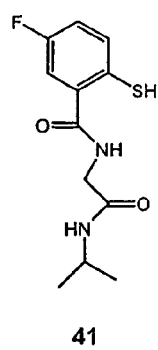
Figure 1:
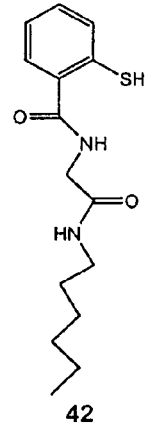
Figure 1:
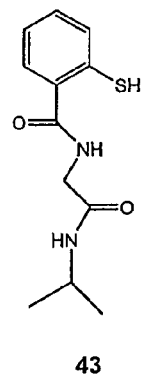
Figure 1:
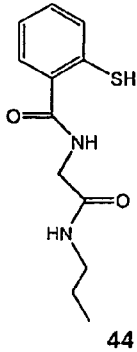
Figure 1:
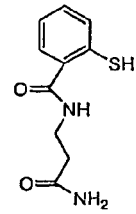
Figure 1:
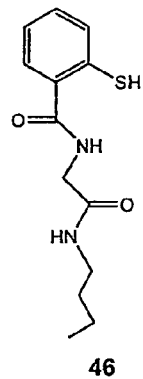
Figure 1:
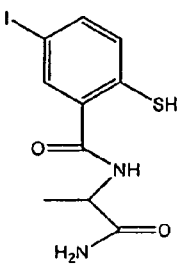
Figure 1:
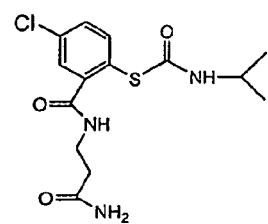
Figure 1:
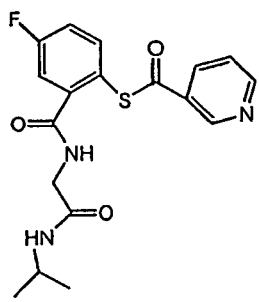
Figure 1:
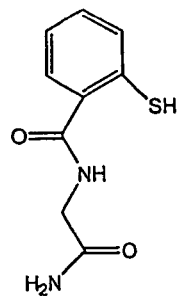
Figure 1:
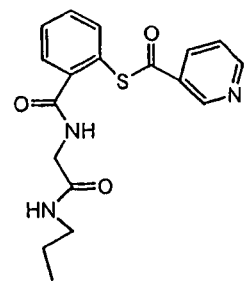
Figure 1:
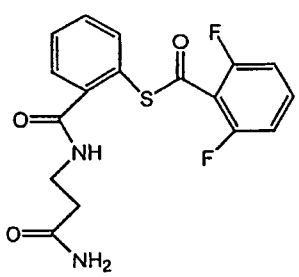
Figure 1:
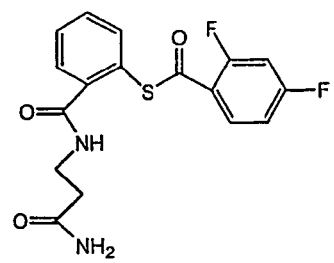
Figure 1:
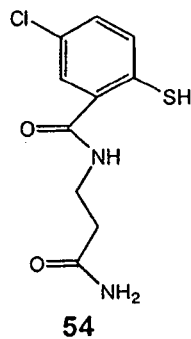
Figure 1:
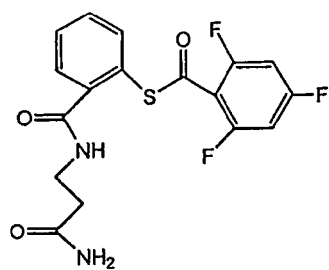
Figure 1:
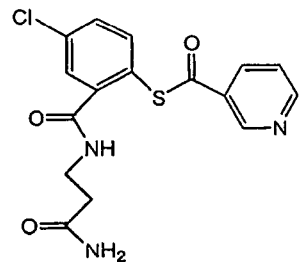
Figure 1:
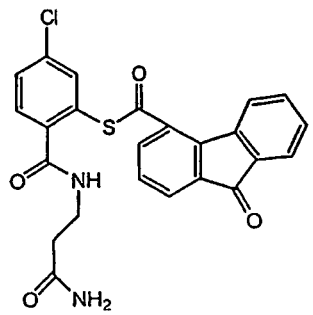
Figure 1:
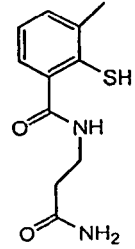
Figure 1:
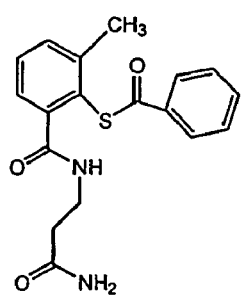
Figure 1:
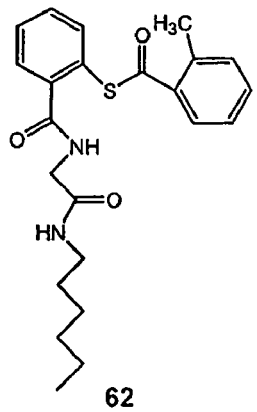
Figure 1:
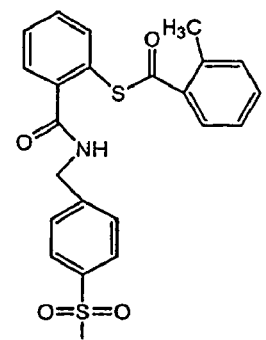
Figure 1:
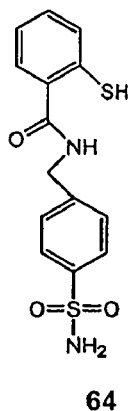
Figure 1:
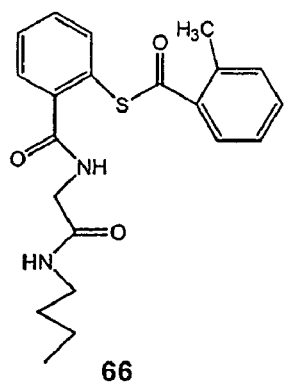
Figure 1:
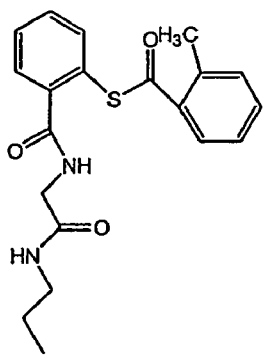
Figure 1:
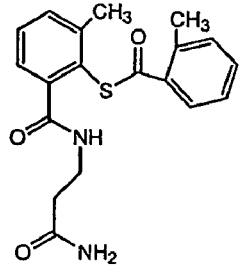
Figure 1:
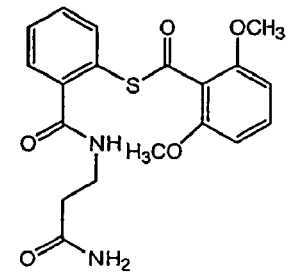
Figure 1:
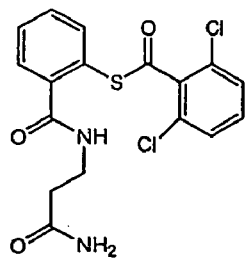
Figure 1:
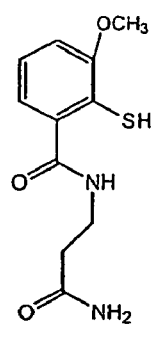
Figure 1:
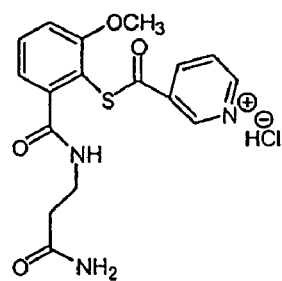
Figure 1:
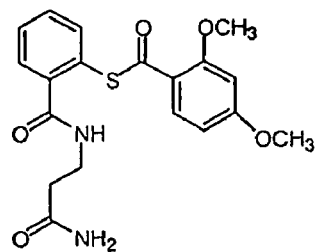
Figure 1:
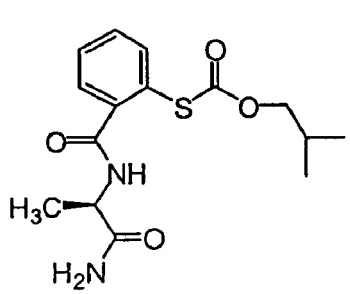
Figure 1:
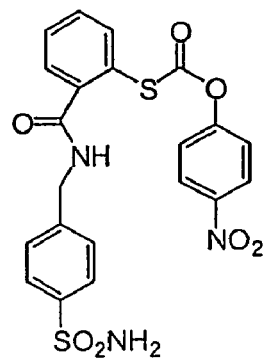
Figure 1:
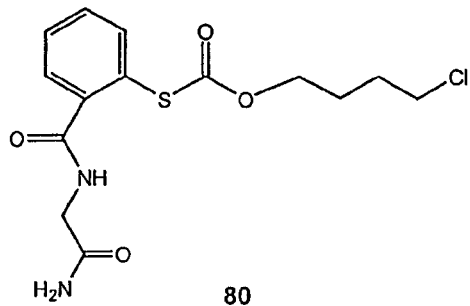
Figure 1:
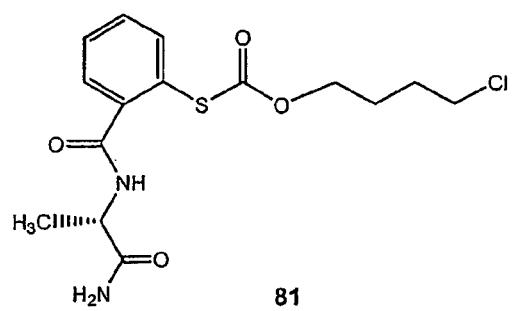
Figure 1:
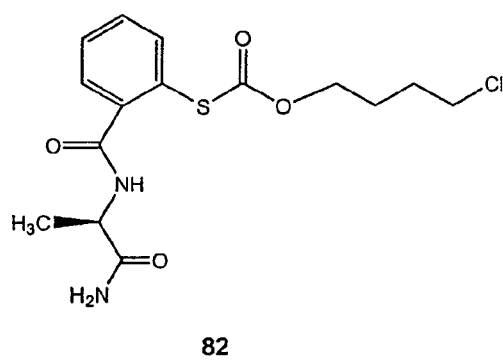
Figure 1:
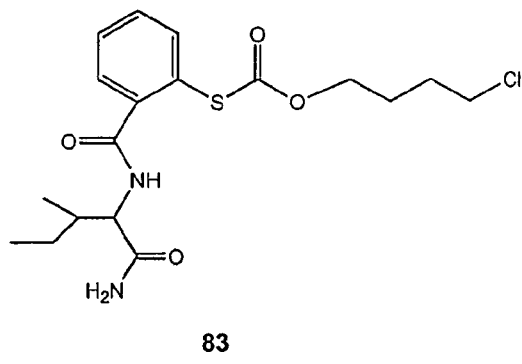
Figure 1:
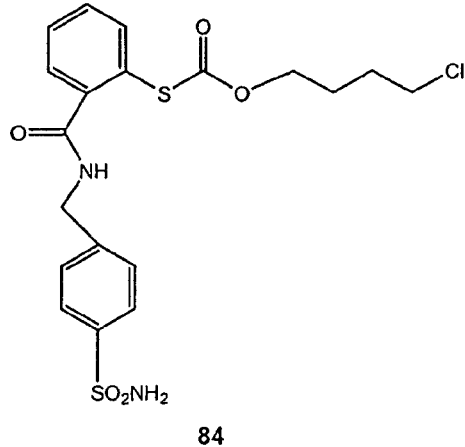
Figure 1:
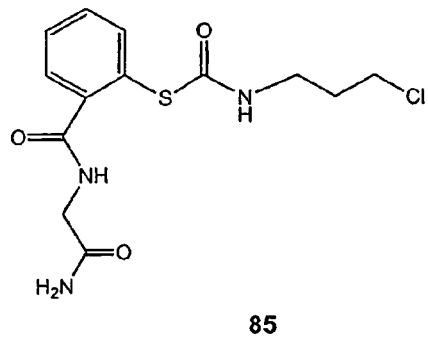
Figure 1:
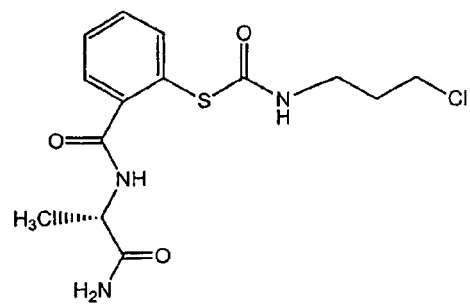
Figure 1:
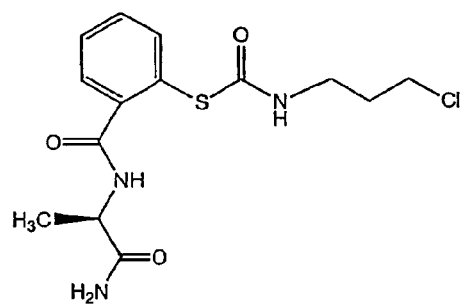
Figure 1:
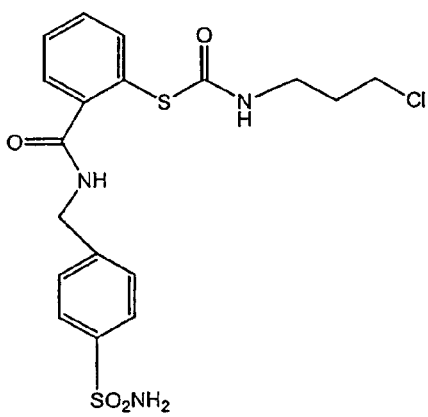
Figure 1:
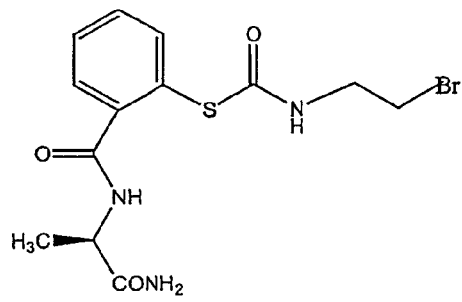
Figure 1:
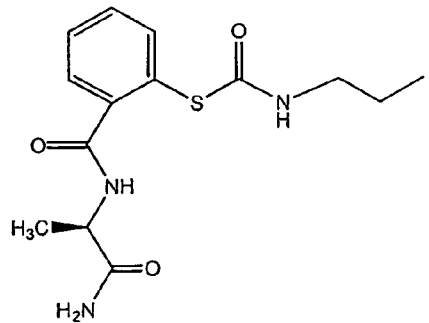
Figure 1:
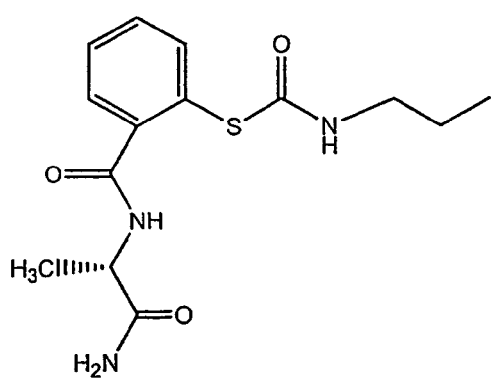
Figure 1:
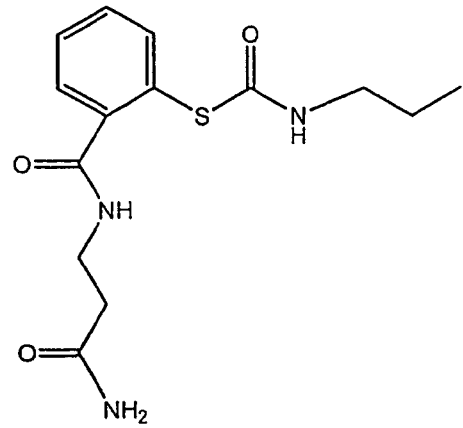
Figure 1:
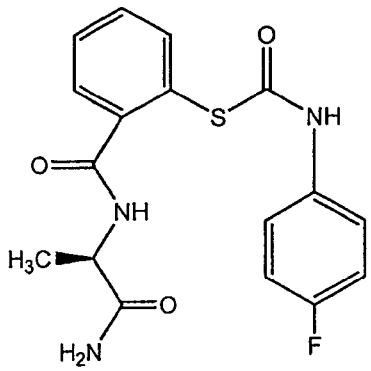
Figure 1:
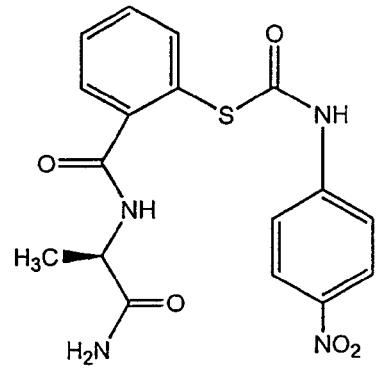
Figure 1:
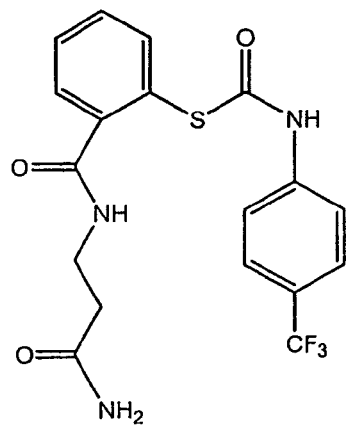
Figure 1:
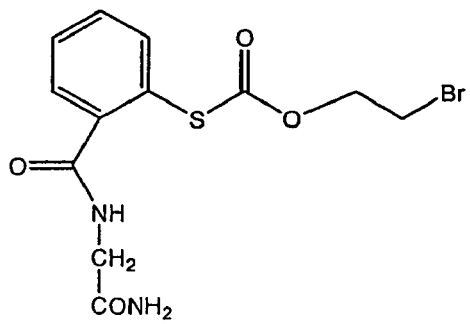
Figure 1:
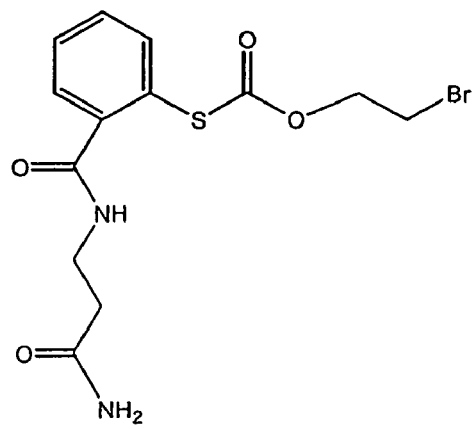
Figure 1:
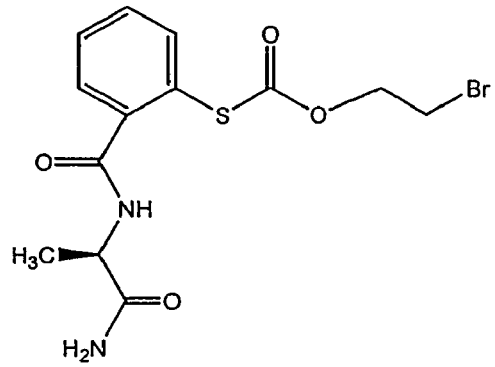
Figure 1:
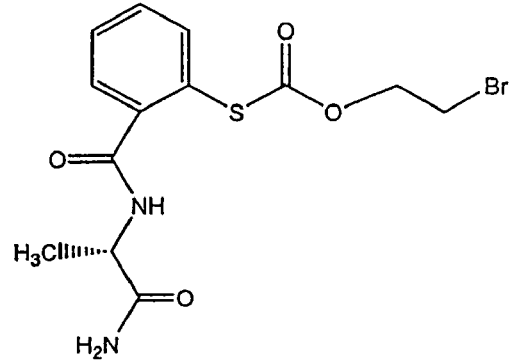
Figure 1:
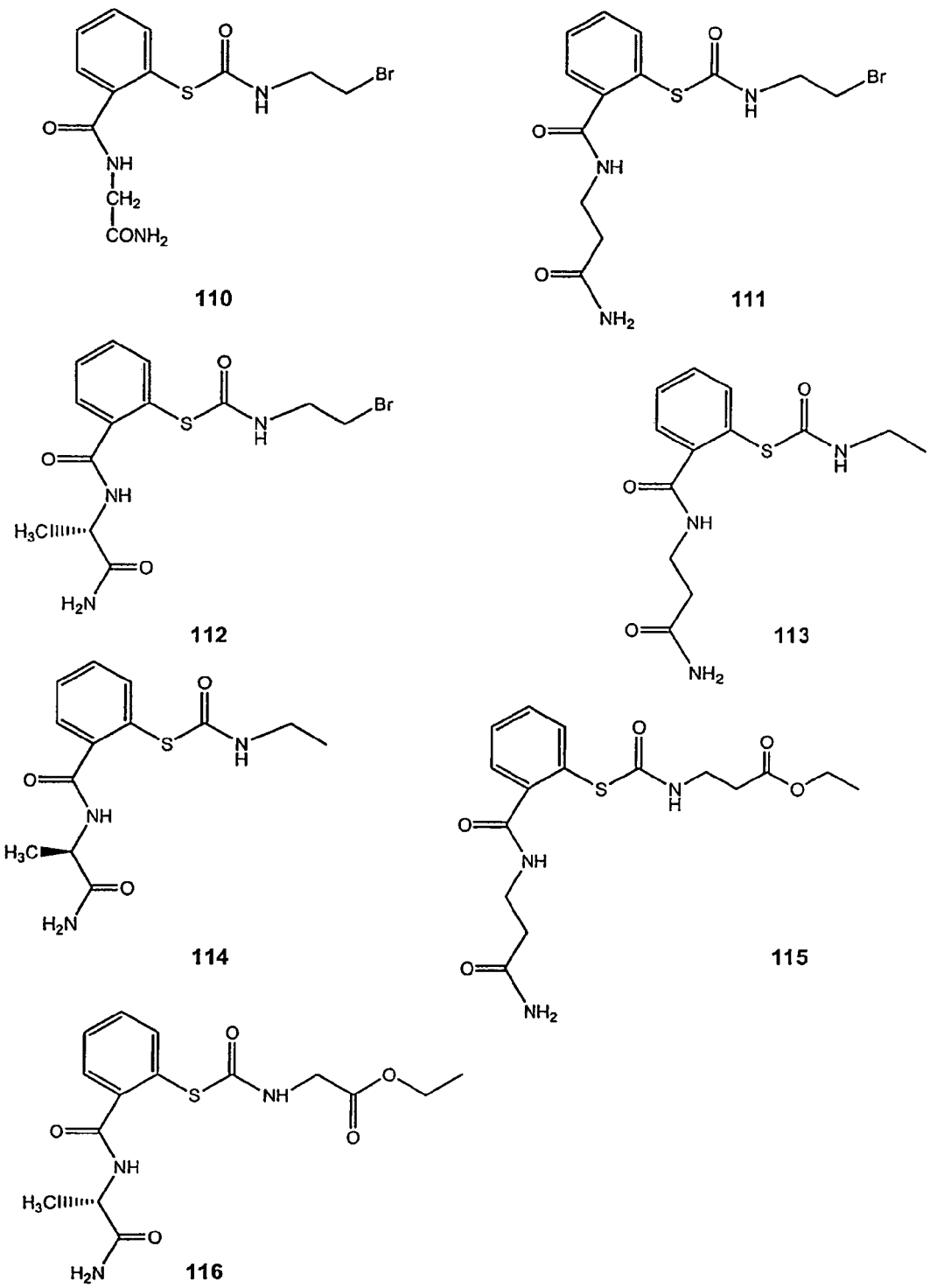
Figure 1:
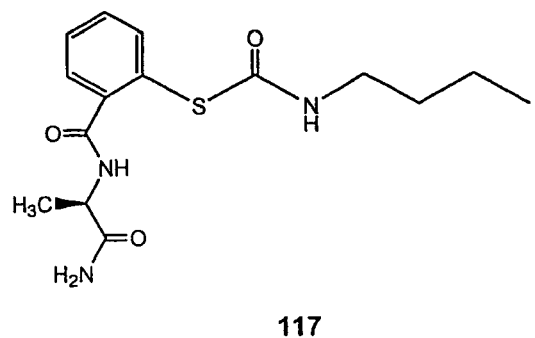
Figure 1:
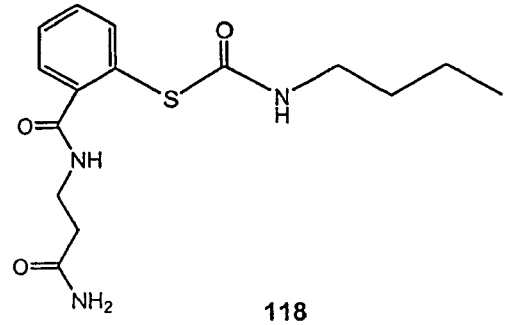
Figure 1:
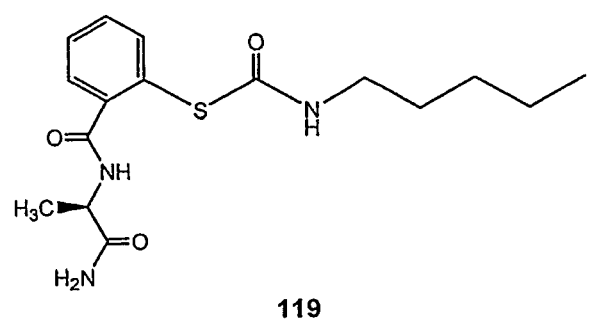
Figure 1:
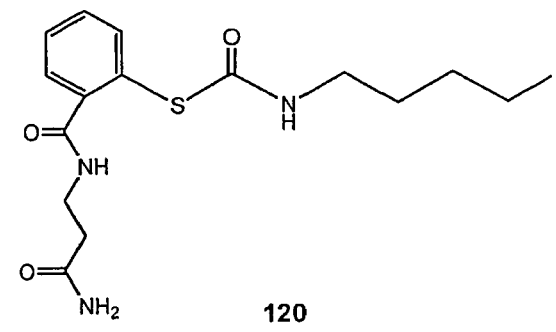
Figure 1:
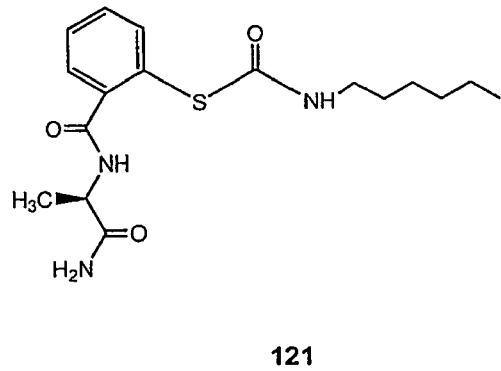
Figure 1:
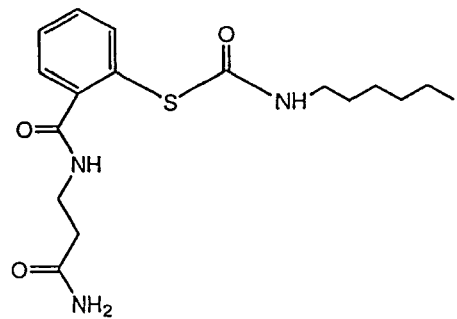
Figure 1:
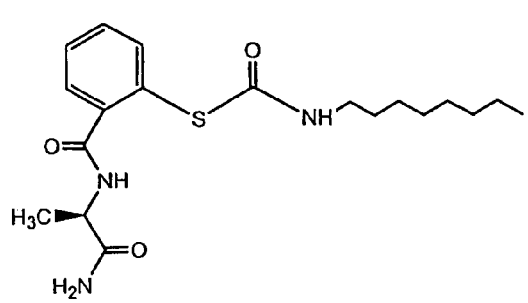
Figure 1:
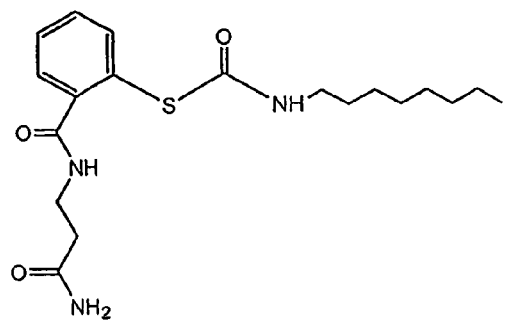
Figure 1:
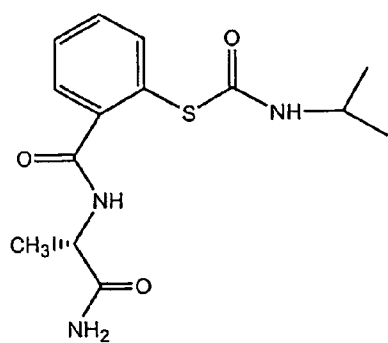
Figure 1:
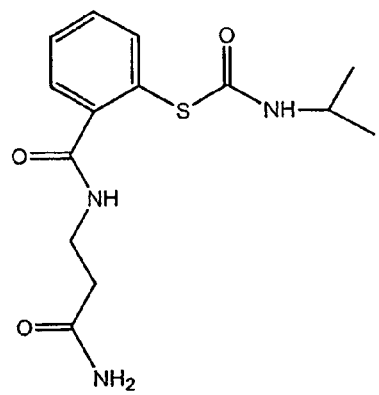
Figure 1:
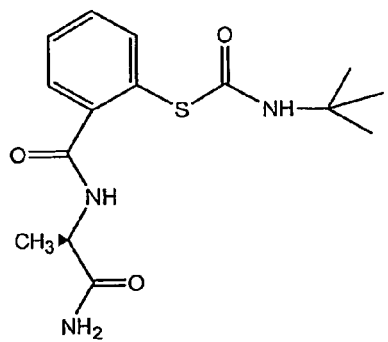
Figure 1:
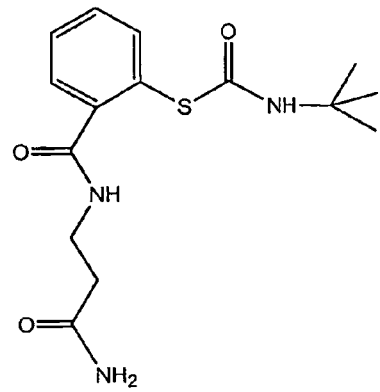
Figure 1:
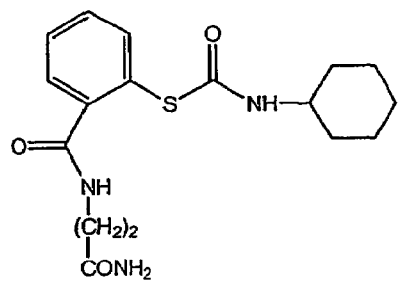
Figure 1:
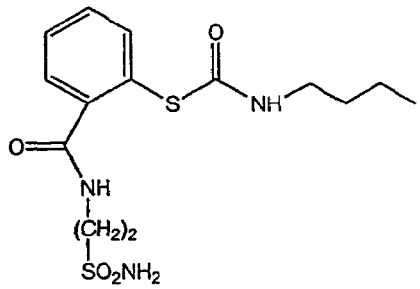
Figure 1:
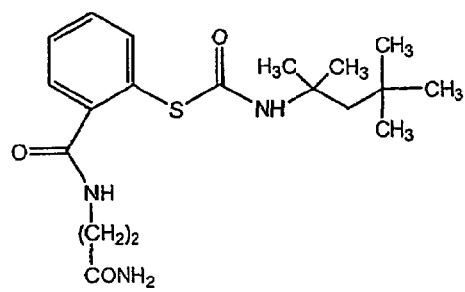
Figure 1:
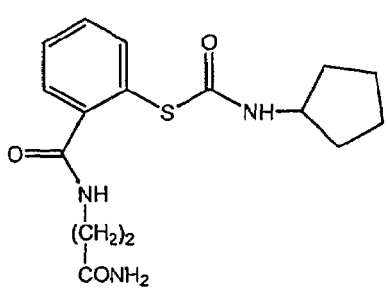
Figure 1:
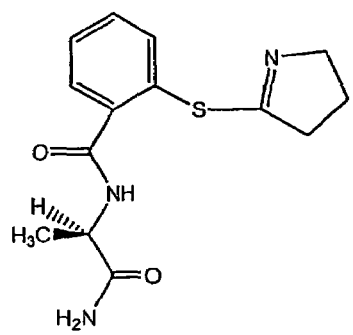
Figure 1:
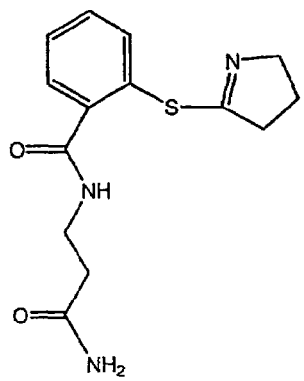
Figure 1:
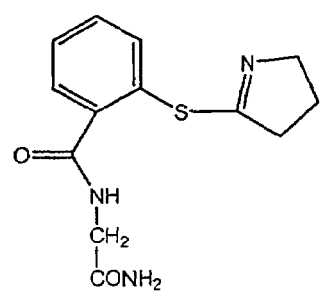
Figure 1:
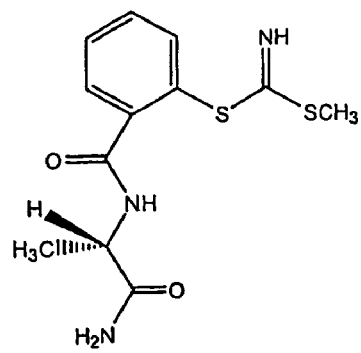
Figure 1:
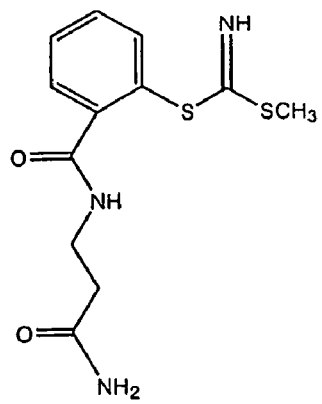
Figure 1:
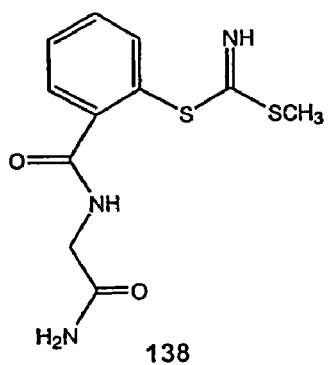
Figure 1:
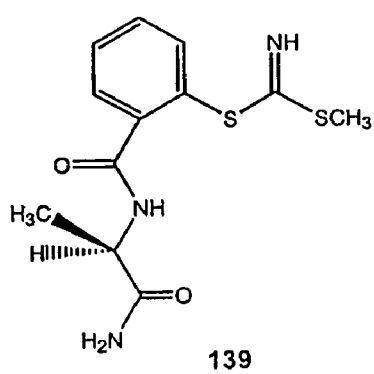
Figure 1:
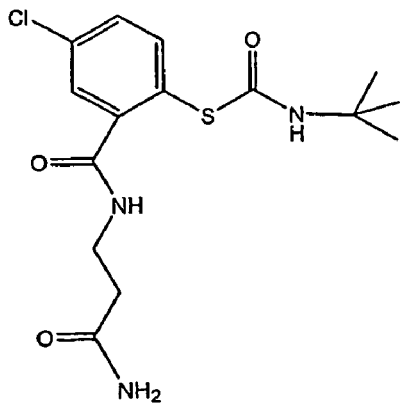
Figure 1:
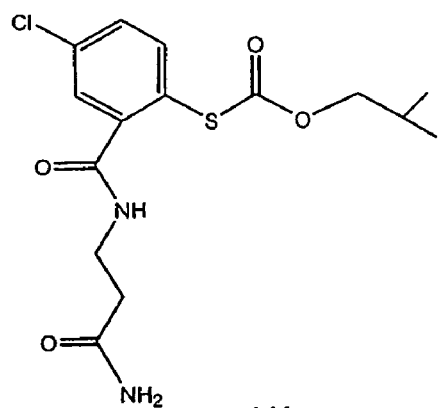
Figure 1:
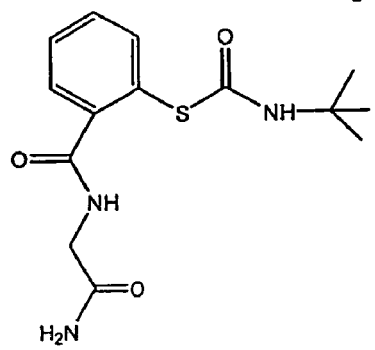
Figure 1:
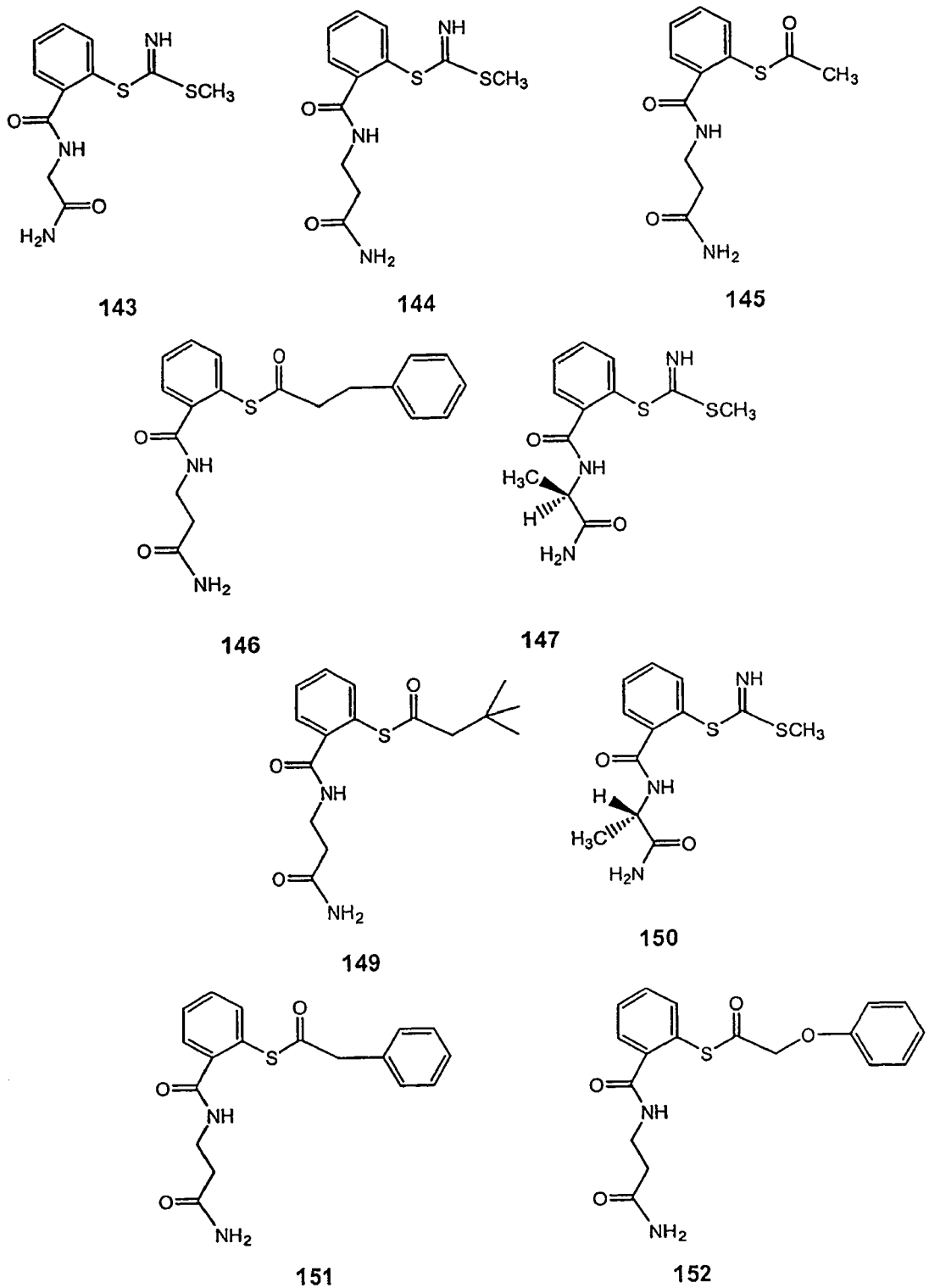
Figure 1:
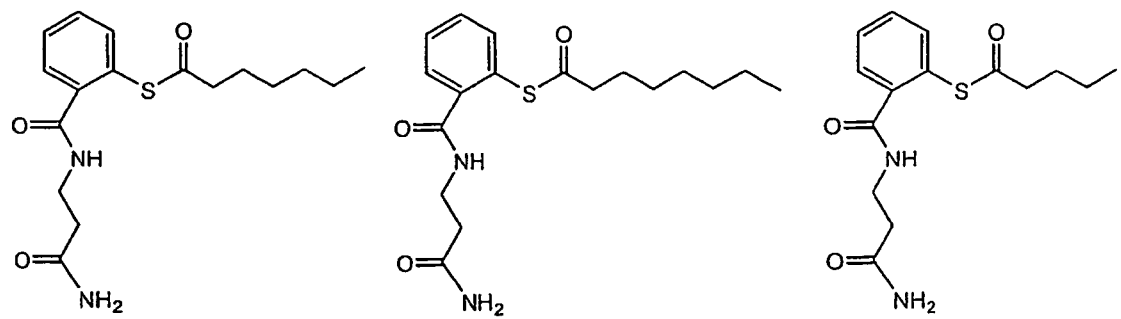
Figure 1:
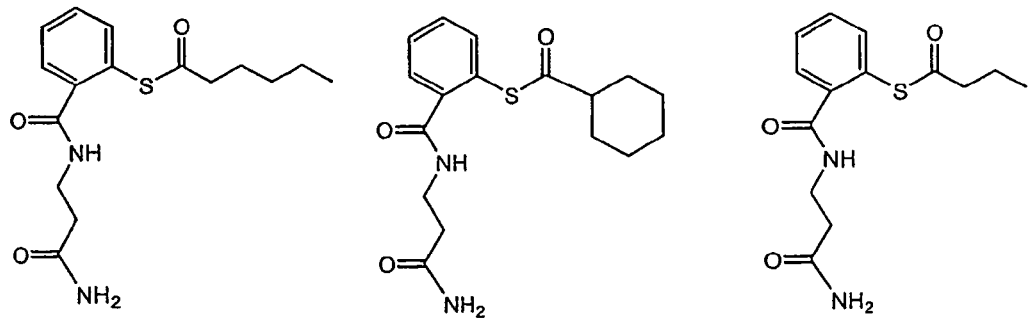
Figure 1:
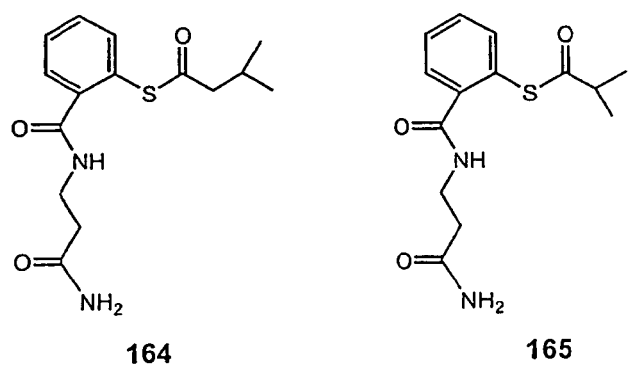
Figure 1:
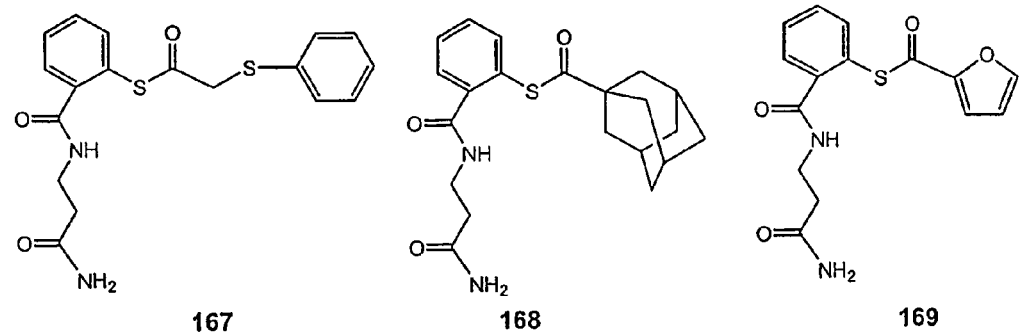
Figure 1:
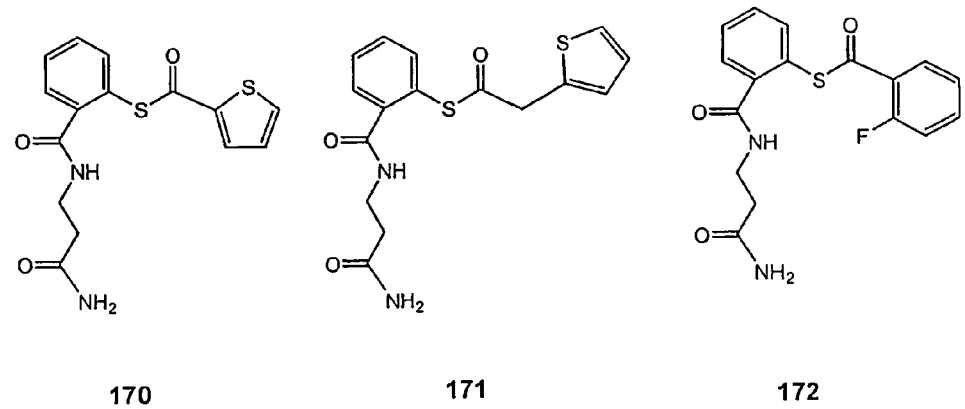
Figure 1:
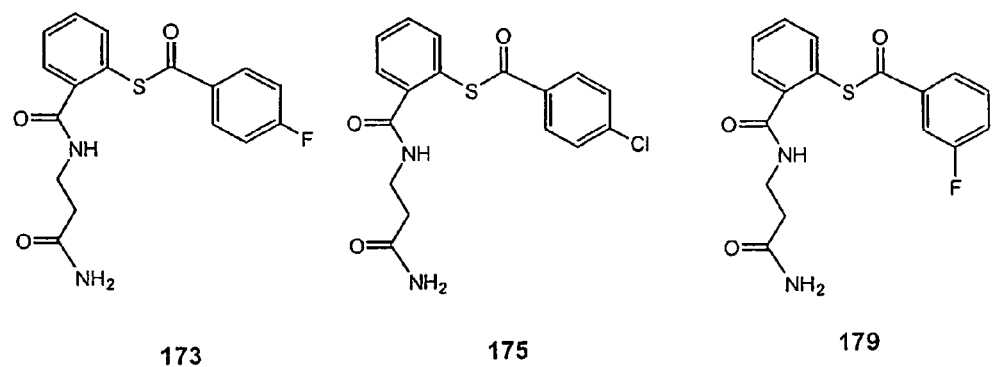
Figure 1:
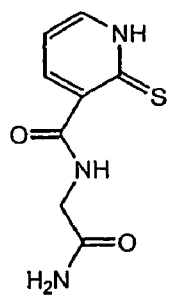
Figure 1:
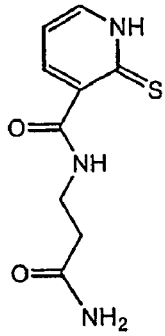
Figure 1:
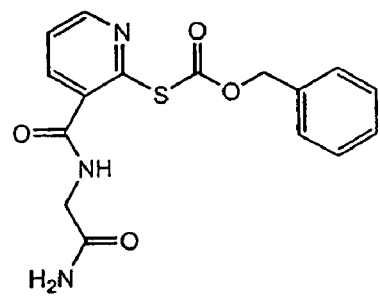
Figure 1:
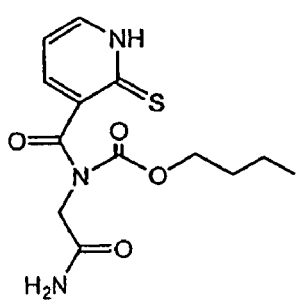
Figure 1:
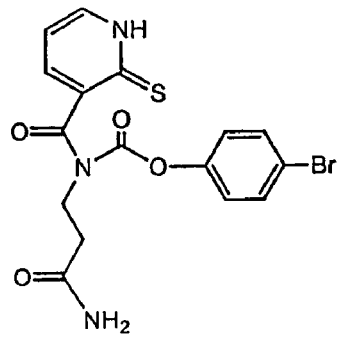
Figure 1:
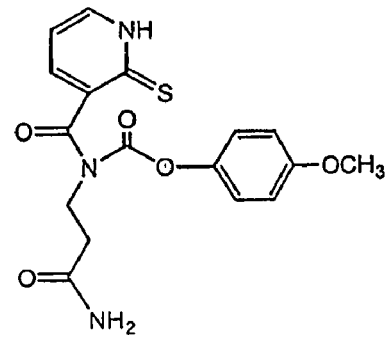
Figure 1:
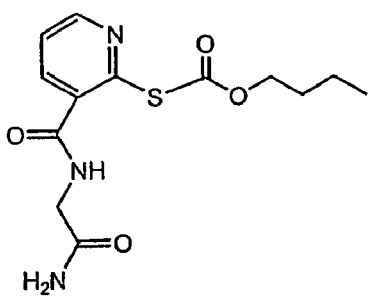
Figure 1:
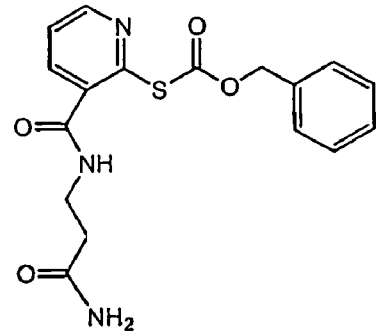
Figure 1:
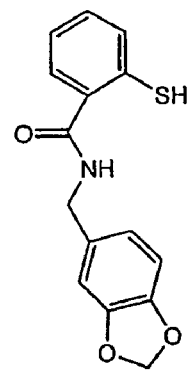
Figure 1:
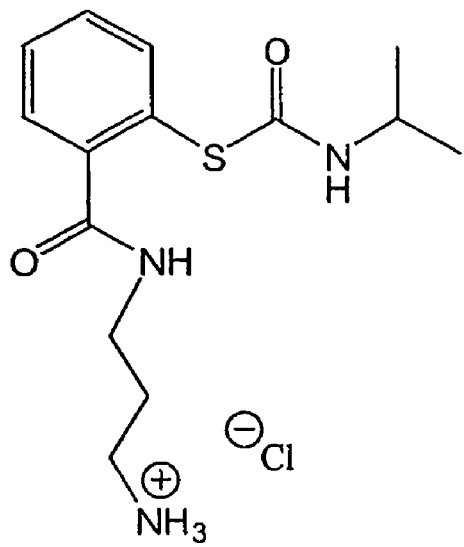
Figure 1:
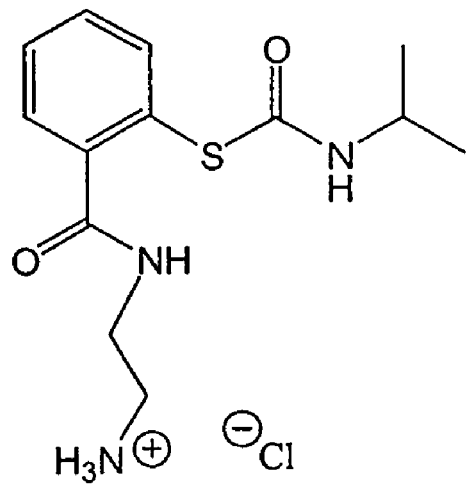
Figure 1:
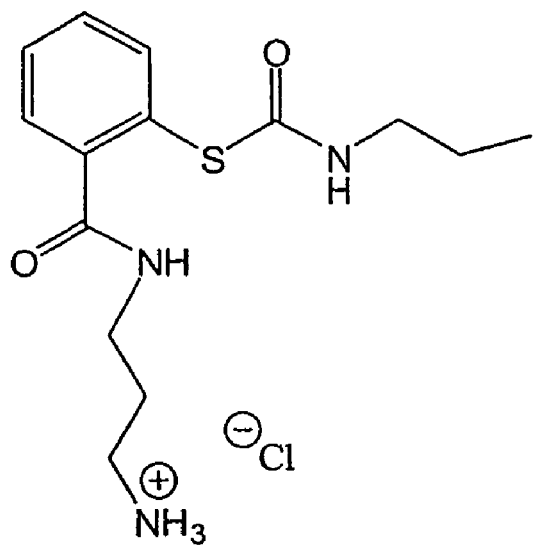
Figure 1:
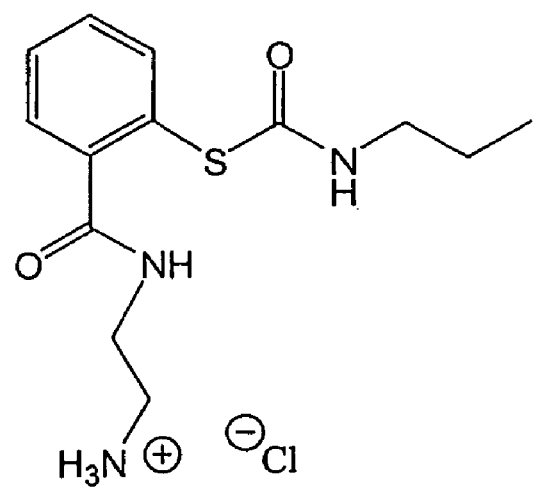
Figure 1:
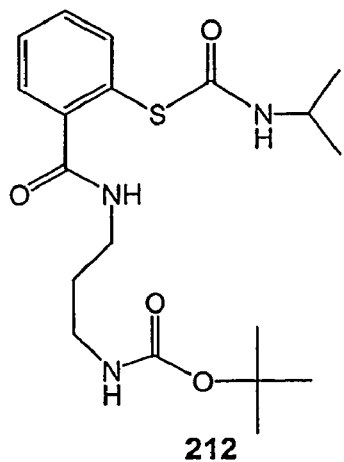
Figure 1:
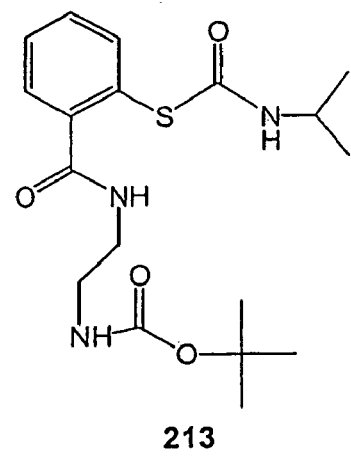
Figure 1:
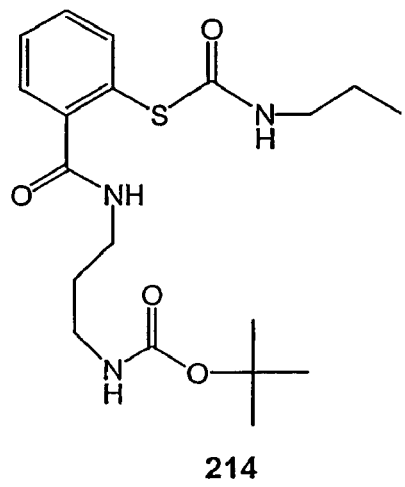
Figure 1:
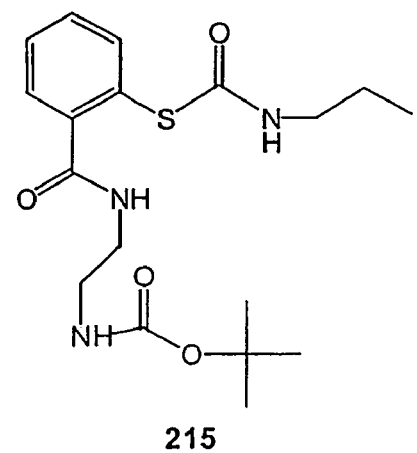
Figure 1:
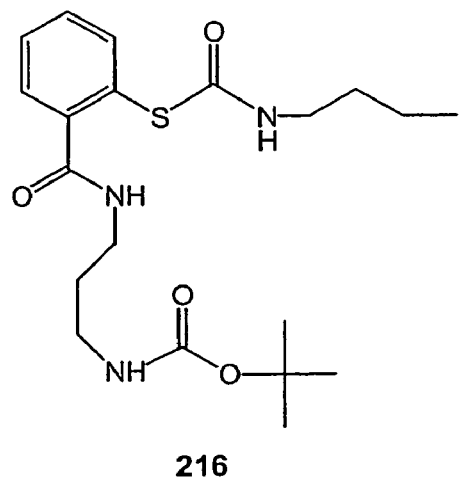
Figure 1:
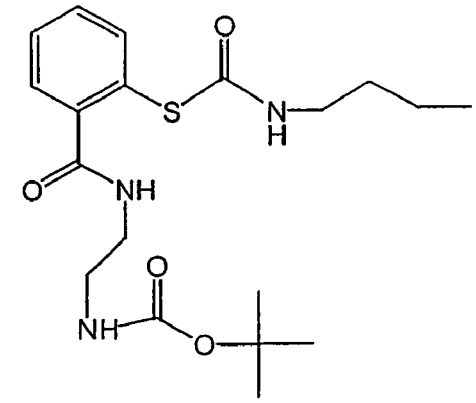
Figure 1:
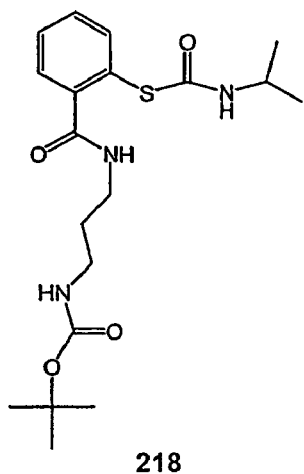
Figure 1:
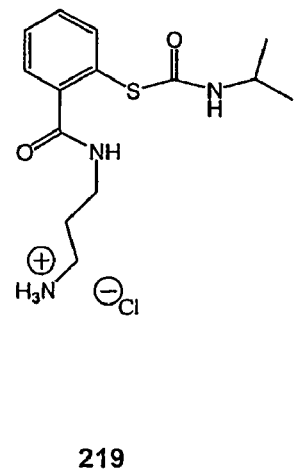
Figure 1:
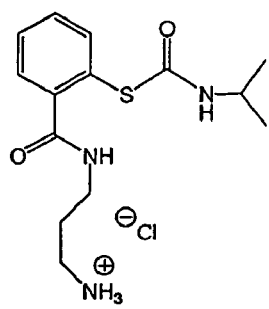
Figure 1:
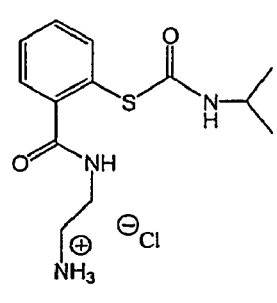
Figure 1:
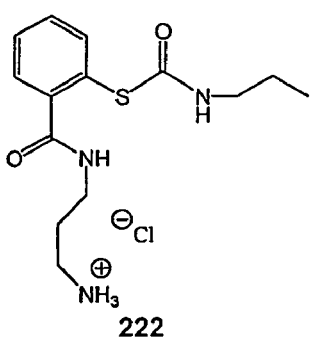
Figure 1:
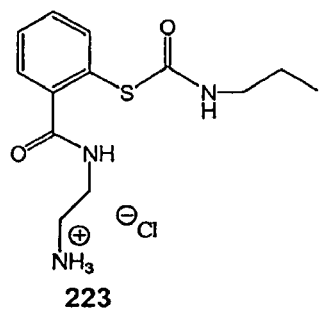
Figure 1:
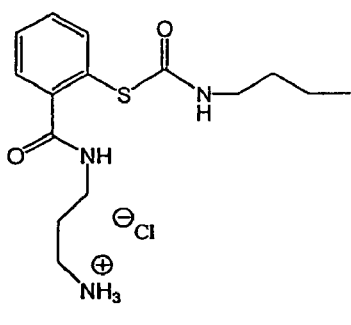
Figure 1:
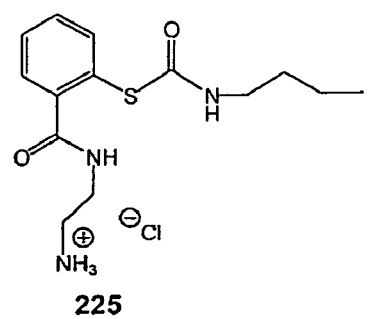
Figure 1:
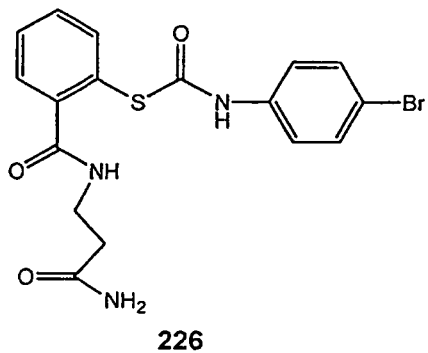
Figure 1:
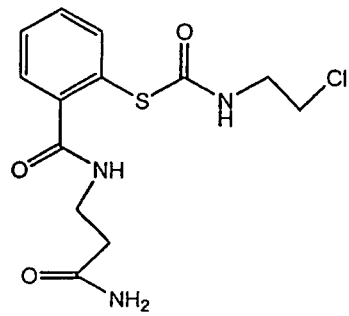
Figure 1:
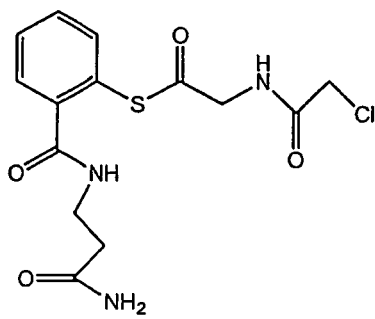
Figure 1:
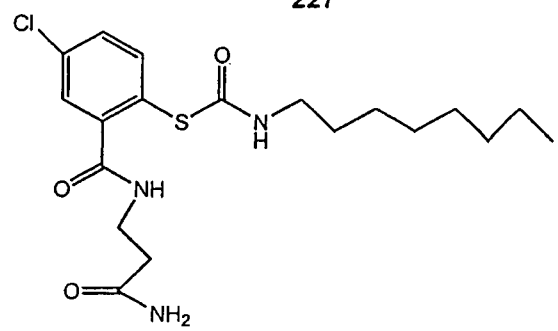
Figure 1:
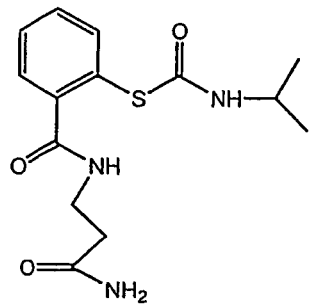
Figure 1:
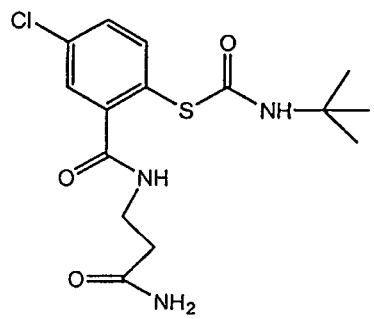
Figure 1:
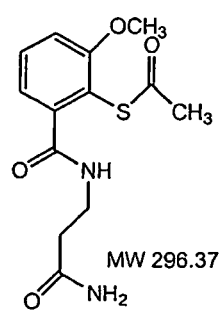

The present invention provides novel compounds, compositions and methods of using these compounds and compositions, inter alia, to inactivate viruses. Certain compounds of the present invention are capable of interacting with zinc finger containing proteins. Because many viruses require zinc finger-containing proteins for activity, these compounds can inactivate a broad range of viruses that contain zinc finger motifs. This inactivation can be effected when the compound contacts the virus's nucleocapsid, or any other zinc finger-containing protein, or other sensitive component of the virus. However, the compositions of the present invention can inactivate a virus by a variety of mechanisms, including, but not limited to, covalent interaction with metal-ion-complexing zinc fingers, and the invention is not limited by any particular theory or mechanism of action.

In one embodiment, the present invention provides a compound of formula (I),

$$K—J—Q—NR^1R^2 \tag{I}$$

wherein K, J, Q, N, $R^1$, and $R^2$ are as described above.

K is an aromatic six-membered ring attached to a carbonyl group and at least one sulfur-containing substituent (J). K may be a benzene ring which is optionally substituted with up to four additional substituents, or a pyridine ring which is optionally substituted with up to three additional substituents. The sulfur-containing substituent, J, is either ortho or meta relative to the carbonyl group on the aromatic ring. In a preferred embodiment, J is ortho to the carbonyl group. In some preferred embodiments, the aromatic ring is a benzene ring; in other preferred embodiments, it is a pyridine ring. In some preferred embodiments, the aromatic ring is a benzene ring that further contains at least one additional substituent. In some especially preferred embodiments, the benzene ring contains a third substituent that is ortho to J, so that the carbonyl, J, and the third substituent are in a 1, 2, 3 arrangement on the benzene ring.

The substituents other than J on the aromatic ring of K are independently selected from the group consisting of halogen, CF$_3$, optionally substituted alkyl, optionally substituted alkoxy, optionally substituted aryl, NO$_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido. Typically, optionally substituted alkyl, optionally substituted alkoxy, and halogen are preferred substituents.

J is a sulfur-containing group that may contain a thiol such as (CH$_2$)$_m$—SH, or it may contain an acylthiol of the formula (CH$_2$)$_m$—S—C(Z)—Y—R$^3$, where m is an integer from 0 to 2; Z is a member selected from the group consisting of O, S, and NR$^4$; and Y is a bond, O, S, or NR$^4$. J also may be a cyclic group of the following structure, where Y is a bond, O, S, or NR$^4$:

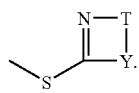

Often, J is preferably a thiol group such as —SH or —CH$_2$SH. In other preferred embodiments, however, J is an acylthio group such as —SC(O)— or —CH$_2$SC(O)—. In some of the more preferred embodiments, when J is an acylthio group, Y is a bond and Z is an oxygen atom. These compounds are referred to as thioesters.

R$^3$ is optionally substituted alkyl, optionally substituted aryl, optionally substituted arylalkyl, optionally substituted cycloalkyl, or optionally substituted cycloalkylalkyl. Compounds having an optionally substituted aromatic for R$^3$ are sometimes preferred when Y is a bond. Compounds having an optionally substituted alkyl group for R$^3$ are sometimes preferred when Y is NR$^4$. R$^3$ does not contain any cationic group such as an N-substituted pyridinium group, a sulfonium group, a tetraalkyl ammonium group, or a phosphonium group that cannot be neutralized by loss of a proton near physiological pH.

R$^4$ is H, optionally substituted alkyl, optionally substituted alkoxy, optionally substituted aryl, and optionally substituted acyl. R$^4$ is H in some preferred embodiments.

In some preferred embodiments, m is 0, and J is SH, and in some preferred embodiments, m is 0, and J is —S—C(Z)—Y—R$^3$. In other preferred embodiments, m is 1. In some preferred embodiments, Y is a bond, and in others Y is NR$^4$. In some more preferred embodiments, Y is a bond and R$^3$ is optionally substituted alkyl or optionally substituted aryl. In some more preferred embodiments, R$^3$ is an optionally substituted aryl.

R$^9$ is H, optionally substituted amino, optionally substituted acyl, optionally substituted acylamino, optionally substituted acyloxy, optionally substituted thioamido, hydroxy, optionally substituted alkyl, optionally substituted aryl, optionally substituted arylalkyl, optionally substituted cycloalkyl, or optionally substituted cycloalkylalkyl. In some preferred embodiments, R$^9$ is either H or an optionally substituted alkyl.

Q is a bond, optionally substituted alkylene, optionally substituted alkylene-C(O), optionally substituted phenylene, optionally substituted cycloalkylene, optionally substituted alkylcycloalkylene, optionally substituted cycloalkylene-alkyl, or a group from the following list of structures:

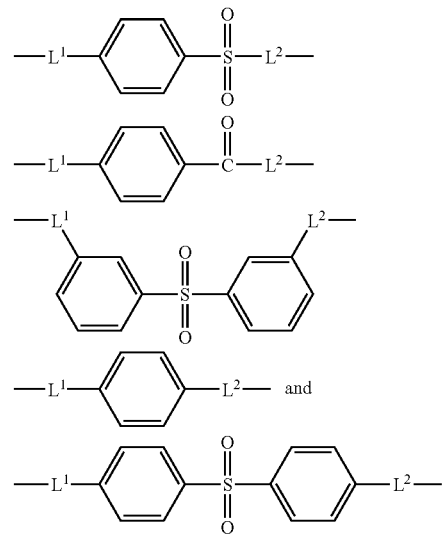

where L$^1$ and L$^2$ are members independently selected from the group consisting of a bond and an optionally substituted alkylene chain of up to 4 carbons.

In some preferred embodiments, Q is a bond, and in others it is an optionally substituted alkylene-C(O). In more preferred embodiments, Q is often an optionally substituted alkylene-C(O), wherein the alkylene-C(O) contains a chain of up to about 4 carbon atoms. In other preferred embodiments, Q is an optionally substituted phenylene or one of the phenyl-containing groups shown above. In some preferred embodiments containing L$^1$ and L$^2$, at least one of L$^1$ and L$^2$ is a bond, and the other one of L$^1$ and L$^2$ is a bond or an alkylene chain of up to about 4 carbons.

R$^1$ is H, optionally substituted alkyl, optionally substituted aryl, optionally substituted heteroaryl, optionally substituted heteroalkyl, or optionally substituted heterocycloalkyl. In many preferred embodiments, R$^1$ is H or an optionally substituted alkyl group.

Preferably, R$^1$ is H or an optionally substituted alkyl group. In some more preferred embodiments, R$^1$ is H or methyl, or R$^1$ and R$^2$ together form an optionally substituted ring of 5 or 6 atoms.

R$^2$ is H, hydroxyl, amino, optionally substituted alkyl, optionally substituted aryl, optionally substituted alkylamine, optionally substituted arylamine, optionally substituted alkoxy, optionally substituted acyl, optionally substituted aminoacyl, optionally substituted alkoxyacyl, optionally substituted alkylthioacyl, optionally substituted arylaminoacyl, optionally substituted aryloxyacyl, optionally substituted arylthioacyl, optionally substituted heteroaryl, optionally substituted heteroalkyl, optionally substituted heterocycloalkyl or optionally substituted acylamino. Alternatively, R$^1$ and R$^2$ are optionally linked together to form an optionally substituted ring of up to about seven atoms including the N to which both are attached.

In some preferred embodiments, R$^2$ is H, and in others it is an alkyl group. In still other preferred embodiments, R$^2$ is an acyl group. In some embodiments, especially when K is K$^3$, R$^2$ is preferably a substituted alkyl group containing at least one polar substituent such as hydroxyl, amino, alkylamine, alkoxy, thiol, sulfonyl, sulfoxide, carboxamido, alkoxycarbonyl (e.g., CH$_3$OC(O)—CH$_2$CH$_2$—) or aryloxycarbonyl groups, or a relatively polar aryl or arylalkyl group such as a substituted benzyl group containing more than one heteroatom such as O, N, or S, for example. Exemplary $R^2$ groups include H, methyl, ethyl, methoxyethyl, ethoxycarbonylethyl, 4-(benzodioxolanyl)methyl, and the like.

Especially preferred compounds of the present invention are more specifically described by Templates I-VIII:

Template I
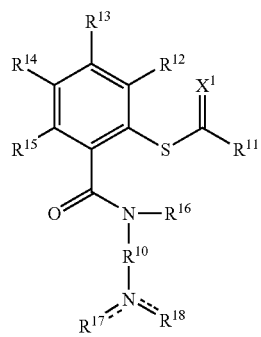

Template II
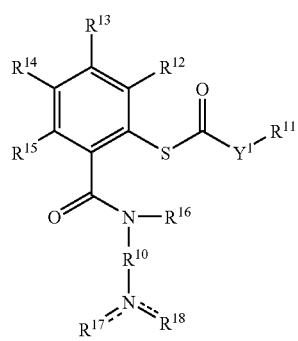

Template III
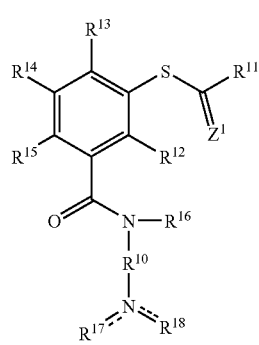

Template IV
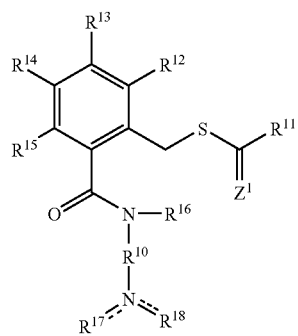

Template V
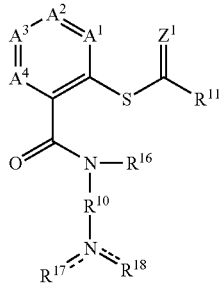

Template VI
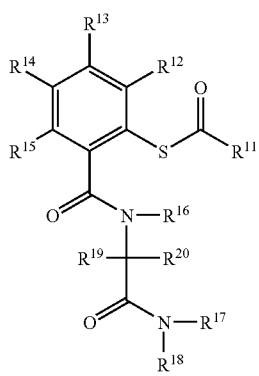

Template VII
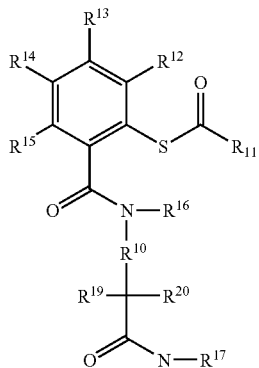

Template VIII
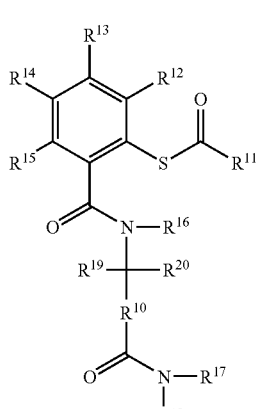

For these Templates, $R^{10}$ is optionally substituted alkylene-C(O)—, alkylene, phenylene, cycloalkylene, or a substructure from the following list:

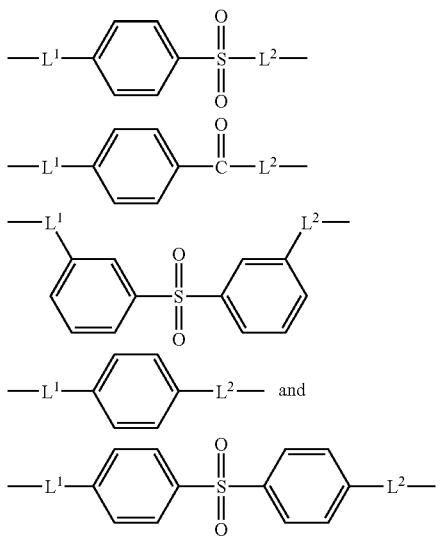

where $L^1$ and $L^2$ are independently a bond or optionally substituted alkylene.

For compounds represented by Templates I-V, $R^{10}$ is preferably optionally substituted alkylene-C(O)—. More preferred compounds of Templates I-V often have $R^{10}$ as —$CH_2C(O)$—, —$CH_2CH_2C(O)$—, or —$CH(Me)C(O)$—. For compounds of the structure represented by Templates VI through VIII, $R^{10}$ is often preferably one of the illustrated substructures. Typically, only one of $L^1$ and $L^2$ in any given compound containing the illustrated substructures is other than abond.

$R^{11}$ is an alkyl, cycloalkyl, heterocycloalkyl, aryl, or heteroaryl group, each of which is optionally substituted. In Template V, one or two of A, B, C and D is nitrogen, making the central ring a pyridine, a pyrimidine, a pyridazine or a pyrazine.

$R^{12}$, $R^{13}$, $^{14}$ and $R^{15}$ are independently selected from H, alkyl, cycloalkyl, heterocycloalkyl, aryl, heteroaryl, alkoxy, alkylamino, arylamino, alkylthio, acyl, acylamino, acyloxy, acylthio, halogen, hydroxy, amino, thioamido, and mercapto groups. In some preferred embodiments, $R^{12}$ is a substituent other than H, such as, for example, optionally substituted alkyl or alkoxy.

$R^{16}$, $R^{17}$ and $R^{18}$ are groups independently selected from H, alkyl, cycloalkyl, heterocycloalkyl, aryl, heteroaryl, alkoxy, alkylamino, arylamino, alkylthio, acyl, acylamino, acyloxy, acylthio, hydroxy, amino, thioamido, and mercapto. Often, in preferred compounds, at least two of these groups are hydrogen atoms. Some preferred embodiments have $R^{16}$, $R^{17}$ and $R^{18}$ each as hydrogen, while some embodiments have an alkyl group for at least one of the three groups. Still other preferred embodiments have an acyl group for $R^{17}$ or $R^{18}$.

$R^{19}$ and $R^{20}$ are groups independently selected from H, alkyl, cycloalkyl, heterocycloalkyl, aryl, and arylalkyl, heteroaryl. In some preferred embodiments, both $R^{19}$ and $R^{20}$ are H. In other preferred embodiments, $R^{19}$ and $R^{20}$ are either H or optionally substituted lower alkyl. Some preferred embodiments are derived from the essential amino acids, so they include the corresponding amino acid alkyl or arylalkyl groups as $R^{20}$.

$X^1$ in Template I is selected from $NR^{21}$ and S. When $X^1$ is nitrogen, $R^{21}$ is sometimes preferably H and sometimes preferably lower alkyl.

$Y^1$ in Template II is selected form the group consisting of $NR^{21}$, O, S, and $C(Z_1)$. In many preferred embodiments, $Y^1$ is $NR^{21}$, where $R^{21}$ is H or optionally substituted alkyl. $Z^1$, when present, is often preferably O.

FIG. 1 illustrates some of the most preferred embodiments of the present invention.

Some compounds within the present invention possess one or more ionizable groups. For example, a pyridine ring or a relatively basic amine may be present within $R^3$, or $NR^1R^2$ may be a basic amino group. Such compounds are capable of forming salts with relatively acidic compounds, and the present invention includes such salts. It especially contemplates the formation of pharmaceutically acceptable inorganic salts, such as those formed by contacting a relatively basic compound of the present invention with hydrochloric acid, hydrobromic acid, or phosphoric acid, and pharmaceutically acceptable organic salts, such as those formed by contacting a relatively basic compound of the present invention with acetic acid, oxalic acid, maleic acid, citric acid, toluenesulfonic acid, and the like.

Some compounds within the present invention possess one or more chiral centers, and the present invention includes each separate enantiomer of such compounds as well as mixtures of the enantiomers. Other compounds within the present invention possess double bonds that can exist as geometric isomers, and the invention includes both cis and trans isomers of such double bonds. Still other compounds within the present invention can exist in multiple tautomeric forms, and the invention includes each stable tautomer of such compounds.

Where multiple chiral centers or multiple geometric isomers or multiple tautomers or combinations of two or more such features exist in compounds of the present invention, the invention includes each combination as well as mixtures thereof.

Some preferred compounds of the present invention possess a chiral center in the Q group that is derived from an alpha-amino acid. In such compounds, Q is a substituted methylene group. For some of these compounds, the isomer derived from an L-amino acid is preferred, and for some of these compounds the isomer derived from a D-amino acid is preferred. In other embodiments of this type, a mixture of both isomers is preferred.

Because of their antiviral activity, the compounds of this invention are useful for the manufacture of medicaments. These medicaments include formulations and compositions useful for the treatment of viral diseases affecting mammals, including humans. They are also useful for inhibiting the transmission of viral diseases from one host to another. Such medicaments typically include pharmaceutically acceptable excipients, fillers, and diluents, and may optionally include other active ingredients such as other antiviral agents.

The present invention also includes pharmaceutical compositions containing compounds of formula (I). These compositions may be pharmaceutical formulations, or they may be combinations of the compounds of the present invention with food, cosmetic, biological, or other items that benefit from treatment with an anti-retroviral agent.

The compositions of the present invention can be used to tag, attenuate or inactivate any organelle, cell or virus comprising a zinc finger-containing protein or other sensitive molecule. In one aspect of the invention, the compositions of the present invention inactivate retroviruses, such as, for example, HIV-1.

In one aspect, the compositions of the present invention are not affected (i.e., their activity is not greatly diminished in vivo) by the reducing environment of biological fluids. Thus, they are effective as therapeutic agents in the treatment of viral, especially retroviral, infections. The virucidal action of the compositions of the present invention can be extracellular or intracellular. Thus, when used as systemic therapeutic agents, they can decrease (slow the rate of), or block, cell to cell transmission of virus and/or the expansion of reservoirs of latent virus. The virucidal activity of the compositions of the present invention is also useful in in vitro applications, such as, e.g., making inactivated viruses to be used as, e.g., reagents or vaccines, and as sterilizing reagents and topical microbiocides.

Although the compositions, including the pharmaceuticals, of the invention are not limited by any particular mechanism or theory, they may selectively target highly conserved, mutationally intolerant viral components, such as the zinc finger region of nucleocapsid proteins. This effectively addresses problems of drug resistance. In addition, the compounds of the present invention may have the capacity to disable virus extracellularly during transit as well as intracellularly during early and late phases of the replication process. This renders them useful for inhibition or prevention of transmission of a viral infection from one host to another.

A "zinc finger" motif is a highly conserved and essential structure found in many viruses, including retroviruses. For example, Gag and Gag-Pol proteins in the Retroviridae, except for Spumaviruses, contain a highly conserved zinc finger motif (CCHC, where C=cysteine and H=histidine) within the nucleocapsid p7 (NCp7) protein portion of the polyprotein (see definitions below). The absolute conservation of the metal chelating cysteine and histidine residues along with other residues of the protein, and the participation of NCp7 in essential functions during early and late phases of virus replication, identifies this feature as an especially appealing antiviral target. Mutations of the chelating residues in the zinc finger yield a non-infectious virus. Because these zinc fingers are identical in most retroviruses, certain compositions of the present invention that are able to inhibit their function may therefore function as broad spectrum antiviral therapeutic drugs, effective against HIV variants that have developed resistance to other antiviral agents.

As noted above, some compounds of the present invention can inactivate HIV-1. While not bound by any particular mechanism or theory, they may interact with HIV-1 nucleocapsid proteins. HIV-1's nucleocapsid (NC) protein, NCp7, contains two zinc fingers separated by only seven amino acid residues (see, e.g., Henderson (1992) J. Virol. 66:1856). Both zinc fingers are essential for infectivity (Aldovini (1990) J. Virol. 64:1920; Gorelick (1990) J. Virol. 64:3207). Thus, the HIV-1 nucleocapsid is a particularly vulnerable target for zinc finger inactivating agents such as certain compounds of the present invention.

Because all evidence points toward complete conservation of the chelating residues and some other key residues within the fingers, the compounds of the present invention can be used as broad-spectrum antiviral agents. Mutation of any of the zinc finger residues results in loss, severe compromise or attenuation of virus infectivity. Even mutations that maintain metal ion-chelating properties of the fingers (CCHC to CCHH or CCCC, where C=cysteine and H=histidine), result in loss of infectivity. Thus, there is no known evidence for a pathway of single or multiple zinc finger mutations leading to restoration of the protein's activity.

In one aspect, the present invention provides compounds characterized by acylthiol and N-substituted carboxylic acid amide groups both linked to an aryl or heteroaryl ring structure. These compounds fall into twelve subgroups defined by a combinatorial arrangement of the components of the acylthio group (J in formula (I)). These components are a carbon atom doubly bonded to Z, which is an oxygen, nitrogen or sulfur atom, and linked to a sulfur atom through a single bond, and also linked to a carbon, nitrogen, oxygen or sulfur atom through a single bond (Y—$R^3$). Each of these subgroups is within the scope of the present invention.

Without being bound by any particular theory or mechanism of action, as part of an antiretroviral drug, the acylthiol linkage may provide a weakly reactive bond that promotes transfer of the acyl group to a nucleophilic target-site atom when the drug is bound in a favorable orientation in a binding site on a protein. This site can be a highly conserved component of a retrovirus, such as the zinc finger loops of the nucleocapsid protein, e.g., NCp7 of HIV-1. The target locus for covalent modification can be one or more cysteine side chains therein. The covalent interaction (acylation) at this site may result in essentially irreversible inactivation of the conserved target structure of the virus, serving to reduce its rate of replication in the host cell and, further, to disturb the pattern of packaging of the genomic RNA in either the budding or cell-free virion.

It has recently also been found that in certain compounds of the present invention containing a free thiol group, the thiol group interacts with the NCp7 zinc finger. These thiol compounds can be given as antiviral agents, or they may be formed as a result of enzyme-promoted or chemical hydrolysis of an acylthiol in vivo, or they may form as a result of the acylation of a zinc finger by an acylthiol compound of the present invention. They may act as ligands displacing the normal chelating bonds between the finger loop cysteines and the central zinc ion. Zinc ions are not ejected in these cases, but resulting small shifts in conformation of the affected loop apparently disturb critical interactions with genomic RNA during the assembly of new viral particles. Thus, like the acylthiols, these free component thiol compounds of the present invention are sometimes highly potent antivirals that are effective to prevent or treat viral infections.

Thiols, by their chemical nature, may not be the best chemotype to give directly as an antiviral drug, however. The pKa values for certain thiols can be as low as 5 to 6 for some aromatic thiols, for example. At physiological pH, such thiols exist substantially as negatively charged (thiolate) species. Their charge may impede absorption and passive membrane transmission. In addition, aromatic thiolates are highly nucleophilic and potentially reactive toward disulfide bonds and other electrophilic structures. For example, they can be employed in catalytic re-scrambling of mismatched cystines in proteins, much in the same manner as protein disulfide isomerase (PDI) which likewise possesses a low pKa thiol (a special cysteine side chain) in its active site (Gough, *J Amer. Chem. Soc.* 124, 3885-3892 (2002)).

Certain of the acylthiols of the present invention overcome these disadvantages possessed by their component thiols, by serving as prodrugs which modify the physical properties and metabolic susceptibility until the compound has time to reach its molecular target. Furthermore, certain acylthiol compounds of the present invention produce the inhibitory activity of a thiol compound and the covalent inactivation of an acylthiol compound. In these compounds, the acyl group may remain intact until the compound reaches a zinc finger protein. The compound then reacts with the zinc finger cysteine, transferring an acyl group onto the cysteine sulfur atom as described above. This inactivates one viral protein molecule, and releases a free thiol. The free thiol can then bind to a second zinc finger protein, resulting in a second inhibitory event. Therefore, certain acylthiol compounds operate by two distinct mechanisms, and can be considered simultaneously a drug and a prodrug.

For such compounds, it is advantageous that the in vivo hydrolysis rate be low enough so that most of the administered acylthiol compound reaches a zinc finger-containing protein before either chemical or enzymatic hydrolysis occurs. This allows it to acylate a first zinc finger protein and also, in the form of a free thiol compound, inhibit a second zinc finger protein. Therefore, slow in vivo hydrolysis is sometimes an advantage for acylthiol compounds of the present invention when used to treat retroviral infections, because slow hydrolysis increases the opportunity for the acylation of a zinc finger protein to occur before the acylthiol is hydrolyzed by other mechanisms operating within the host organism.

I. Definitions

To facilitate understanding the invention, a number of terms are defined below.

The term "halo" or "halogen" as used herein refers to fluorine, chlorine, bromine, or iodine.

As used herein, the term "alkyl", alone or in combination with other terms such as alkylamino, refers to refer a genus of radicals including branched and unbranched, saturated or unsaturated, monovalent hydrocarbon radicals, including substituted derivatives and equivalents thereof. In one aspect, the hydrocarbons have from 1 to about 20 carbons, and often preferably from 1 to about 10 carbons. When the alkyl group has from 1 to about 6 carbon atoms, it is referred to as a "lower alkyl." "Alkyl" groups also include alkyl chains optionally interrupted with one or two members, which may be the same or different, selected from the group consisting of a double bond, a triple bond, O, S, NR", C(O), and C(NR"), so long as the alkyl group is attached through a carbon atom of its alkyl chain. R" on NR" or C(NR") may be H, acyl, lower alkyl, or alkoxy. Exemplary alkyl radicals include, e.g., structures containing one or more methylene, methine and/or methyne groups arranged in acyclic and/or cyclic forms. Branched structures having a branching motif similar to isopropyl, tert-butyl, isobutyl, 2-ethylpropyl, etc. are also included. As used herein, the term encompasses "substituted alkyls."

"Substituted alkyl" refers to alkyls as just described, containing one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, arylamino, aryloxyalkyl, mercapto, thia, aza, oxo, alkoxycarbonyl, alkylaminocarbonyl, both saturated and unsaturated cyclic hydrocarbons, heterocycles and the like. The number of such groups that may be present is limited by the number of valences available on the alkyl group radical. These groups may. be attached to any carbon of the alkyl moiety. Additionally, these groups may be pendent from, or integral to, the alkyl chain.

The term "alkylene" as used herein, either alone or in combination with other terms, refers to an alkyl group as described above which contains two unoccupied valences, and is hence a diradical. Such diradicals attach to two groups that will be specified, in addition to being optionally substituted as described above. "Alkylene-C(O)", for example, refers to an alkylene chain attached to a carbonyl group [C(O)] at one of its two unoccupied valences. This alkylene-C(O) group must attach to one group through an unoccupied valence of the alkyl chain portion of the alkylene, and to a second group through the unoccupied valence of the carbonyl carbon atom that occupies one of the two radical positions of the alkylene.

"Substituted alkylene" refers to alkylenes as just described, containing one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, arylamino, aryloxyalkyl, mercapto, thia, aza, oxo, both saturated and unsaturated cyclic hydrocarbons, heterocycles and the like. The number of such groups that may be present is limited by the number of valences available on the alkylene group radical. These groups may be attached to any carbon of the alkylene moiety. Additionally, these groups may be pendent from, or integral to, the alkylene chain.

As used herein, the term "cycloalkyl", alone or in combination with other terms, refers to substantially carbocyclic rings of 3 to about 8 atoms, and includes fused, bridged, and spiro-fused ring systems, including bicyclic and tricyclic ring systems containing a total of up to about 16 ring atoms. Such cycloalkyl groups are optionally substituted, and the rings are optionally interrupted with one or two members, which may be the same or different, selected from the group consisting of a double bond, a triple bond, O, S, NR", C(O), and C(NR"), where R" is H, optionally substituted alkyl or optionally substituted acyl, so long as the cycloalkyl group is attached through a carbon atom; no ring smaller than five ring atoms can include a double bond in the ring; and no ring smaller than about 7 atoms can include a triple bond within the ring.

"Substituted cycloalkyl" refers to cycloalkyls as just described, containing one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, arylamino, aryloxyalkyl, mercapto, thia, aza, oxo, both saturated and unsaturated cyclic hydrocarbons, heterocycles and the like. The number of such groups that may be present is limited by the number of valences available on the cycloalkyl group radical. These groups may be attached to any carbon of the cycloalkyl moiety. Additionally, these groups may be pendent from, or integral to, the cycloalkyl ring.

As defined herein the term "heteroalkyl", alone or in combination with other terms, refers to any alkyl group, as defined above, wherein one or more of its carbon atoms (other than the one which links the radical to other structures) is replaced by an atom of another element (a "heteroatom", e.g., N, S, O, Si, P, etc.). It includes optionally substituted heteroalkyl groups.

The term "heterocycloalkyl" refers to a cyclic alkyl group possessing at least one heteroatom in its cyclic structure, and includes optionally substituted heterocycloalkyl groups.

The term "alkylamino" is used herein, either alone or in combination with other terms, to refer to the to the —NRR' group, which is attached through the N (nitrogen) atom, and where R and R' are H or optionally substituted lower alkyl, optionally substituted aryl, arylalkyl or substituted arylalkyl, wherein the alkyl, aryl, substituted aryl, arylalkyl and substituted arylalkyl groups are as described herein. Suitable alkylamino radicals include, for example, amino, methylamino, ethylamino, phenylamino, substituted phenylamino, benzylamino, phenethylamino, tert-butylamino, dimethylamino, pyrrolidino, morpholino, and the like.

The term "alkoxy" is used herein, either alone or in combination with other terms, to refer to the to the —OR group, which is attached through the O (oxygen) atom, and where R is a lower alkyl, substituted lower alkyl, aryl, substituted aryl, arylalkyl or substituted arylalkyl, wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy phenethyloxy, tert-butoxy, and the like.

The term "aryl" is used herein, either alone or in combination with other terms, to refer to an aromatic substituent that may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, fluroenyl, diphenylmethyl and benzophenone among others. The term "aryl" encompasses "arylalkyl."

"Substituted aryl" refers to aryl as just described and including one or more functional groups such as lower alkyl, acyl, halogen, alkylhalos (e.g., $CF_3$), hydroxy, amino, alkoxy, alkylamino, acylamino, acyloxy, phenoxy, mercapto, each of which is optionally substituted. Both saturated and unsaturated cyclic hydrocarbons which are fused to the aromatic ring(s), linked covalently or linked to a common group such as a methylene or ethylene moiety are included. The linking group may also be a carbonyl such as in cyclohexyl phenyl ketone. The term "substituted aryl" encompasses "substituted arylalkyl."

As used herein the term "heteroaryl", either alone or in combination with other terms, refers to any aryl group, as defined above, wherein one or more of its ring atoms is replaced by a heteroatom (a "heteroatom", e.g., N, S, O, etc). It includes bicyclic and tricyclic fused ring systems where each ring is aromatic and at least one of the aromatic rings contains a heteroatom. It further includes bicyclic and tricyclic ring systems where one or more of the rings is not aromatic, as long as at least one of the rings is an aromatic ring that contains a heteroatom.

"Substituted heteroaryl" refers to heteroaryl as just described and including one or more functional groups such as lower alkyl, acyl, halogen, alkylhalos (e.g., $CF_3$), hydroxy, amino, alkoxy, alkylamino, acylamino, acyloxy, phenoxy, mercapto, each of which is optionally substituted. Both saturated and unsaturated cyclic hydrocarbons which are fused to the heteroaromatic ring(s), linked covalently or linked to a common group such as a methylene or ethylene moiety are included. The linking group may also be a carbonyl such as in cyclohexyl pyridinyl ketone. The term "substituted heteroaryl" encompasses "substituted heteroarylalkyl."

The term "arylalkyl" is used herein, either alone or in combination with other terms, to refer to a subset of "aryl" in which the aryl group is further attached to an alkyl group, as defined herein.

The terms "array", "microarray", "DNA array", "nucleic acid array" and "biochip" are used interchangeably herein, and include all known variations of these devices. In alternative aspects of the invention, the devices and methods of the present invention incorporate, in whole or in part, designs of arrays, and associated components and methods, as described, e.g., in U.S. Pat. Nos. 6,197,503; 6,174,684; 6,156,501; 6,093,370; 6,087,112; 6,087,103; 6,087,102; 6,083,697; 6,080,585; 6,054,270; 6,048,695; 6,045,996; 6,022,963; 6,013,440; 5,959,098; 5,856,174; 5,770,456; 5,700,637; 5,556,752; 5,143,854.

"Contacting" refers to the act of bringing components of an interaction (e.g., a compound of formula (I) with a zinc finger protein or a viral protein) or a reaction into adequate proximity such that the interaction or reaction can occur. More generally, as used herein, the term "contacting" can be used interchangeably with the following: bound to, combined with, added to, mixed with, passed over, flowed over, etc.

As used herein, the term "Gag-Pol protein" refers to the polyprotein translation product of HIV-1 or other retroviruses, as described, e.g., by Fehrmann (1997) Virology 235: 352-359; Jacks (1988) Nature 331: 280-283. The "Gag protein" is processed by a viral protease to yield mature viral proteins, see, e.g., Humphrey (1997) Antimicrob. Agents & Chemotherapy 41: 1017-1023; Karacostas (1993) Virology 193: 661-671.

As used herein, "isolated," when referring to a molecule or composition, such as, for example, a compound of the present invention, a compound bound to a polypeptide, a polypeptide-RNA complex or a virus, or a compound-inactivated virus, means that the molecule or composition is separated from at least one other compound, such as a protein, other nucleic acids, etc., or other contaminants with which it is associated in vivo or in its naturally occurring state. In the context of compounds made by synthetic means, an isolated composition also includes a partially, or substantially, purified preparation containing the active ingredient. Thus, a compound, polypeptide or virion is considered isolated when it has been separated from any other component with which it is naturally associated, e.g., cell membranes, as in a cell extract, serum, and the like. An isolated composition can, however, also be substantially pure. An isolated composition can be in a homogeneous state and can be in a dry state or an aqueous solution. Purity and homogeneity can be determined, for example, using analytical chemistry techniques such as polyacrylamide gel electrophoresis (SDS-PAGE) or high performance liquid chromatography (HPLC).

As used herein, the term "nucleocapsid protein" or "NC protein" refers to the retroviral nucleocapsid protein, which is an integral part of the virion nucleocapsid where it coats the dimeric RNA genome, as described by Huang (1997) J Virol. 71: 4378-4384; Lapadat-Tapolsky (1997) J. Mol. Biol. 268: 250-260. HIV-1's nucleocapsid protein is termed "NCp7," see also Demene (1994) Biochemistry 33: 11707-11716.

The term "retrovirus" as used herein refers to viruses of the Retroviridae family. These viruses can have ssRNA transcribed by reverse transcriptase, as described by, e.g., P. K. Vogt, "Historical introduction to the general properties of retroviruses." In Retroviruses, eds. J. M. Coffin, S. H. Hughes and H. E. Varmus, Cold Spring Harbor Laboratory Press, 1997, pp. 1-26; Murphy et al. (eds.) Archives of Virology/Supplement 10, 586 pp. (1995) Springer Verlag, Wien, N.Y. For a general description of the Retroviridae family, see the Committee on International Taxonomy of Viruses, Virology Division of the International Union of Microbiology Societies viral classifications and taxonomy. Retroviridae family members containing zinc finger motif-containing polypeptides and whose activity, e.g., replication or infectivity, can be inhibited by the compounds of the present invention include, e.g., avian sarcoma and leukosis retroviruses (alpharetroviruses), mammalian B-type retroviruses (betaretroviruses) (e.g., mouse mammary tumor virus), human T-cell leukemia and bovine leukemia retroviruses (deltaretroviruses) (e.g., human T-lymphotropic virus 1), murine leukemia-related group (gammmaretroviruses), D-type retroviruses (epsilonretroviruses (e.g., Mason-Pfizer monlcey virus), and lentiviruses. Lentiviruses include, e.g., bovine, equine feline, ovine/caprine, and primate lentivirus groups, such as human immunodeficiency virus type 1 (HIV-1). Examples of particular species of viruses whose replicative capacity inactivated by the compounds of the present invention include HIV-1, HIV-2, SIV, BIV, EIAV, Visna, CaEV, HTLV-1, BLV, MPMV, MMTV, RSV, MuLV, FeLV, BaEV, and SSV retroviruses.

As used herein, the term "acylthiol" refers to a chemical structure, G—S—(C=X)—G', wherein G and G' represent any two groups except that G usually joins to the sulfur atom (S in the -2 oxidation state) through a C—S bond, while G' may join to the 'C=X' carbon via a C—C bond, a C—O bond, a C—S bond, or a C—N bond. X represents O, S, or NR", where R" is H, alkyl, hydroxy, or alkoxy, As used herein, the terms "thiolester" and "thioester" may be used interchangeably, and they refer to a chemical structure, G—S—(C=O)—G', wherein G and G' represent any two groups except that G usually joins to the sulfur atom (S in the -2 oxidation state) through a C—S bond and G' must join to the carbonyl carbon via a C—C bond. These thioesters are a subset of acylthiols that are sometimes preferred embodiments of the present invention.

As used herein, the term "zinc finger" refers to a polypeptide motif consisting of cysteines and/or histidines that coordinate metal ions giving rise to structures involved in protein/nucleic acid and/or protein/protein interactions. The compounds of the present invention are capable of modifying the structure of zinc finger peptides in such a way that allows eventual dissociation of the metal ions. Typically, the metal ion is a divalent cation, such as those of zinc or cadmium. A zinc finger motif-containing protein is commonly a highly conserved and essential structure in viruses. Zinc finger motifs are found in human papilloma virus (HPV), particularly, HPV E6 and E7 proteins (see, e.g., Ullman (1996) Biochem. J. 319: 229-239), influenza virus (see, e.g., Nasser (1996) J. Virol. 70: 8639-8644). In most subfamilies of Retroviridae, including avian sarcoma and leukosis retroviruses, mammalian B-type retroviruses, human T-cell leukemia and bovine leukemia retroviruses, D-type retroviruses, and lentiviruses, the invariable zinc finger motif is the most highly conserved structure. Retroviral nucleocapsid, Gag and Gag-Pol proteins have zinc finger motifs. In retroviruses, the zinc finger motif typically consists of 14 amino acid residues, with four residues being invariant, one exemplary zinc finger motif is described as Cys(X)2Cys(X)4His(X)4Cys and is referred to as a "CCHC zinc finger" (Henderson (1981) J. Biol. Chem. 256: 8400). Zinc fingers chelate zinc through their histidine imidazole and cysteine thiolates (Berg (1986) Science 232: 485; Bess (1992) J. Virol. 66: 840; Chance (1992) Proc. Natl. Acad. Sci. U.S.A. 89: 10041; South (1990) Adv. Inorg. Biochem. 8: 199; South (1990) Biochem. Pharmacol. 40: 123-129). CCHC zinc fingers perform essential functions in retroviral infectivity, such as packaging genomic RNA. They are also essential for early events in virus infection.

As used herein, the term "antiviral activity" means a compound has demonstrated some degree of antiviral activity in any assay, e.g., the XTT cytoprotection assay or p24 ELISA assays. As used herein, the term "virucidal" includes any degree of viral attenuation, including, but not limited to, complete inactivation or killing of a virus.

As used herein, terms such as "viral infectivity" or "index of infectivity" refers to the capacity of virus to pass from an infected cell to an uninfected cell, bringing about productive infection of the uninfected cell. For example, measurements of infectivity may be carried out by the MAGI assay, wherein the uninfected recipient cells are Hela CD4 HIV LTR Gal cells.

As used herein, the terms "inhibit the transmission of the virus" and "antiviral activity" mean the ability of a compound to negatively affect viral replicative capacity in any way. Such inhibition of transmission, e.g., loss in replicative-capacity can be measured using any means known in the art. For example, a compound is inhibiting the transmission of the virus (having antiviral activity) if it diminishes a virus' ability to produce progeny, (when in the form of a virion) fuse with a cell, enter a cell, bud from a cell, survive intracellularly or extracellularly, reverse transcribe its RNA genome, translate viral proteins, process polyproteins with proteases, effect intracellular assembly of viral components into a capsid, and the like. The ability of a compound of the present invention to inhibit the transmission of a virus is not limited by any chemical or biological mechanism or pathway, A compound can inhibit infectivity or transmission (decrease replicative capacity) of a virus by, e.g.: binding to a nucleocapsid protein, such as NCp7; preventing binding of NCp7 to viral RNA or another nucleic acid; being involved in a specific chemical attack resulting in a stable or transient adduct; promoting the formation of inter- and intramolecular disulfide bonds through consequent destabilization of the NCp7 zinc finger loops; interacting with other conserved or non-conserved residues within the NCp7 protein which results in loss of function; and the like.

Unless otherwise defined, terms used herein are intended to have the meaning that would be understood by a person of ordinary skill in the art for that term in its instant context.

II. Compounds and Methods of Synthesis

The present invention provides novel compounds for inactivating viruses, such as retroviruses. The skilled artisan will recognize that the compounds of the present invention can be synthesized using a variety of procedures and methodologies, which are well described in the scientific and patent literature, e.g., Organic Syntheses Collective Volumes, Gilman et al. (Eds), John Wiley & Sons, Inc., NY; Venuti (1989) Pharm. Res. 6: 867-873; the Beilstein Handbook of Organic Chemistry (Beilstein Institut fuer Literatur der Organischen Chemie, Frankfurt, Germany); Beilstein online database and references obtainable therein. The invention can be practiced in conjunction with any method or protocol known in the art, which is well described in the scientific and patent literature. Therefore, only a few general techniques will be mentioned prior to presenting specific methodologies and examples relative to the novel acylthiols and methods of the present invention.

Organic reagents and intermediates can be obtained from, e.g., Sigma/Aldrich/Fluka (St. Louis, Mo.; Milwaukee, Wis.), Fisher/Acros (Raleigh, N.C.) and Lancaster Synthesis, Inc. (Windham, N.H.). Solvents and other chemicals were reagent grade. Structure and composition of all compounds were verified by $^1$H NMR and, when necessary, by EI MS, and analyzed by silica layer TLC, eluting with chloroform-methanol mixtures and viewing with UV light. Isolation and purification of reaction products were accomplished by standard techniques, which would be obvious to one of ordinary skill in the art.

Compounds of the present invention can be synthesized by combining reactions known to persons of ordinary skill in the art of chemical synthesis. Reactions specifically useful for preparing compounds of this invention are described in Bioorg. Med. Chem. 10, 1263-73 (2002) and J Med. Chem. 42, 67-86 (1999), both of which are incorporated herein by reference. The general scheme used to prepare these compounds consists of the preparation of an aryl carboxylic acid disulfide compound of formula (II).

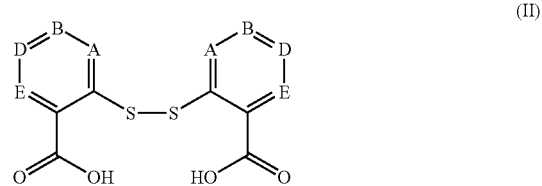

Many such compounds and the methods for their preparation are well known to those of skill in the art. The benzoic acid moieties are activated by methods well known in the art, and are used to acylate amine compounds of formula (III). Methods for such activation include formation of acyl halides, such as acyl chlorides, and activated esters, such as N-acyloxysuccinimides. Also, many other methods for dehydratively forming amide bonds from an amine and a carboxylic acid are known, including coupling with reagents such as dialkyl carbodiimides.

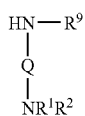

Many compounds of formula (III) are known, and methods for preparation of compounds of formula (III) are well known to persons of skill in the art.

Where appropriate, reactive functional groups other than the amine which is intended to react with the activated benzoic acid group can be protected to prevent undesired side reactions. Methods for selecting, attaching, and removing such protecting groups are well known to those of ordinary skill in the art, and are described, for example, in Peter Wuts and Theodora Greene's book, *Protective Groups in Organic Synthesis* (1999).

Acylation of compound (III) produces a disulfide of formula (IV), which is reduced to produce the free thiol compound of formula (V), for example, using TCEP-HCl (tris(2-carboxyethyl) phosphine hydrochloride).

Compounds of formula (V) are the component thiol compounds of the present invention, and can optionally be acylated with a wide variety of active acylating agents to produce the acylthiol compounds of formula (I). The required acylating agents are well known, and conditions for such acylations are obvious to those of ordinary skill in the art.

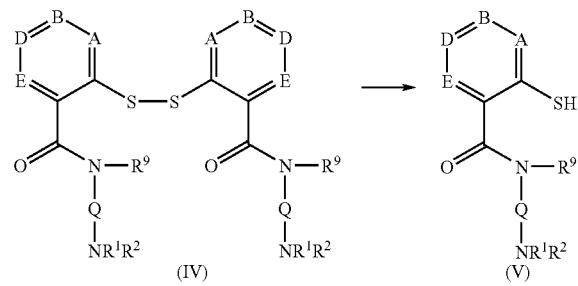

Some preferred compounds of the present invention are set forth in FIG. 1.

III. Compositions

The invention provides a composition comprising a bio-organic, inorganic or other material and an amount of one or more compounds of the present invention effective to inactivate or attenuate a viral protein or a virion that comes in contact with the material, e.g., a virus contaminating the material. The material can be bio-organic, such as, e.g., blood plasma, nutrient media, protein, a pharmaceutical, a cosmetic, a sperm or oocyte preparation, cells, cell cultures, bacteria, viruses, foods, drinks. They can be surgical or other medical materials, such as, e.g., implant materials or implantable devices (e.g., plastics, artificial heart valves or joints, collagens), prostheses, medical materials (e.g., tubing for catheterization, intubation, IVs) and containers (e.g., blood bags, storage containers), and the like. Some preferred compounds for incorporation in compositions of this invention are set forth in FIG. 1.

A. Virucidals

A compound of the present invention can be in the form of a composition that is applied to any of the above materials as a virucidal reagent and removed before the material's use. The virucidal composition can contain a mixture of different compounds of the present invention in varying amounts. For example, compounds of the present invention can be added to cell cultures to reduce the likelihood of viral contamination, providing added safety for the laboratory workers.

B. Pharmaceutical Formulations

The invention provides pharmaceutical formulations comprising one or more of the compounds of the present invention. The compounds of the present invention can be used in pharmaceutical compositions that are useful for administration to mammals, particularly humans, for the treatment of viral infections, especially retroviral, infections. The compounds of the present invention may be formulated alone or in combination with other pharmacologically active ingredients. Of special interest are formulations including a second antiviral agent such as, for example, nucleoside analogs, nucleotide analogs, reverse transcriptase inhibitors, integrase inhibitors, fusion inhibitors and protease inhibitors that are active against retroviruses such as HIV.

The compounds of the present invention can be formulated as pharmaceuticals for administration in a variety of ways. Typical routes of administration include both enteral and parenteral. These include, e.g., without limitation, subcutaneous, intramuscular, intravenous, intraperitoneal, intramedullary, intrapericardiac, intrabursal, oral, sublingual, ocular, nasal, topical, transdermal, transmucosal, vaginal or rectal. The mode of administration can be, e.g., via swallowing, inhalation, injection or topical application to a surface (e.g., eyes, mucous membrane, skin). Particular formulations typical and appropriate for specific modes of administration are familiar to those of skill in the art. Various contemplated formulations include, e.g., aqueous solution, solid, aerosol, liposomal and transdermal formulations. Details on techniques for formulation and administration are well described in the scientific and patent literature, see, e.g., the latest edition of "Remington's Pharmaceutical Sciences" (Maack Publishing Co, Easton Pa).

1. Aqueous Solutions for Enteral, Parenteral or Transmucosal Administration

Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances to enhance stability, deliverability or solubility, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. The intravenous solution can include detergents and emulsifiers such as lipids. Aqueous solutions also are useful for enteral administration as tonics and administration to mucous or other membranes as, e.g., nose or eye drops. In exemplary preparations, the composition can contain a compound in an amount of about 1 mg/ml to 100 mg/ml, or, about 10 mg/ml to about 50 mg/ml.

2. Formulations for Enteral or Transdermal Delivery

Solid formulations can be used for enteral administration. They can be formulated as, e.g., pills, tablets, powders or capsules. For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally from about 5%-95% of active ingredient, preferably from about 10% to about 60% active ingredient.

An exemplary non-solid formulation is for enteral (oral) administration. The carrier can be selected from various oils including those of petroleum, animal, vegetable or synthetic origin, e.g., peanut oil, soybean oil, mineral oil, sesame oil, and the like. See Sanchez, et al., U.S. Pat. No. 5,494,936. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Nonionic block copolymers synthesized from ethylene oxide and propylene oxide can also be pharmaceutical excipients; copolymers of this type can act as emulsifying, wetting, thickening, stabilizing, and dispersing agents, see, e.g., Newman (1998) Crit. Rev. Ther. Drug Carrier Syst. 15:89-142.

An exemplary unit dosage form, such as a tablet, can be between about 50 mg/unit to about 2 grams/unit, preferably between about 100 mg/unit to about 1 gram/unit.

3. Topical Administration: Transdermal/Transmucosal Delivery

Systemic administration can also be by transmucosal or transdermal means. For transmucosal or transdermal administration, e.g., intra-vaginal or intra-rectal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays, for example, or using suppositories. For topical administration, the agents are formulated into ointments, creams, salves, powders and gels. In one embodiment, the transdermal delivery agent can be DMSO. Transdermal delivery systems can also include, e.g., patches.

The compounds can also be administered in sustained delivery or sustained release mechanisms, which can deliver the formulation internally. For example, biodegradeable microspheres or capsules or other biodegradeable polymer configurations capable of sustained delivery of a composition can be included in the formulations of the present invention (see, e.g., Putney (1998) Nat. Biotechnol. 16:153-157).

4. Formulation for Delivery by Inhalation

For inhalation, the formulated compound of the present invention can be delivered using any system known in the art, including dry powder aerosols, liquids delivery systems, air jet nebulizers, propellant systems, and the like. See, e.g., Patton (1998) Biotechniques 16:141-143; inhalation delivery systems by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute 0.1%-20% by weight of the composition, preferably 0.25%-5%. The balance of the formulation is ordinarily propellant.

Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve. See, e.g., Edwards (1997) Science 276:1868-1871. An exemplary nebulizer or aerosolizer device for administering compounds of this invention typically delivers an inhaled dose of about 1 mg/m3 to about 50 mg/m3. Delivery by inhalation is particular effective for delivery to respiratory tissues for the treatment of respiratory conditions including an inflammatory component.

5. Other Formulations

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. For a general discussion of pharmacokinetics, See, Remington's Pharmaceutical Sciences, supra, Chapters 37-39.

IV. Methods of Use

The compounds and compositions of the present invention can be used to treat or prevent viral infections. They are also useful for the inactivation of viruses, and such inactivated viruses are useful as vaccines, for example, or for the production or detection of antibodies. The compounds are also useful for detecting viruses containing zinc finger proteins, and for other purposes. Some preferred compounds for use in the following methods are set forth in FIG. 1.

A. Use as Pharmaceuticals

The compounds of the present invention are used for the treatment and prevention of viral infection, particularly, retroviral infections. The amount of compound adequate to accomplish this is defined as a "therapeutically effective dose." The dosage schedule and amounts effective for this use, ie., the "dosing regimen," will depend upon a variety of factors, including frequency of dosing, the stage of the disease or condition, the severity of the disease or condition, the general state of the patient's health, the patient's physical status, age and the like. In calculating the dosage regimen for a patient, the mode of administration also is taken into consideration. The dosage regimen must also take into consideration the pharmacokinetics, i.e., the compound's rate of absorption, bioavailability, metabolism, clearance, and the like (see, e.g.; the latest Remington's edition, supra).

Single or multiple administrations of the compositions can be carried out with dose levels and pattern being selected by the treating physician. The administrations provide an amount of a compound of the present invention sufficient to treat the patient effectively. The total effective amount of a compound of the present invention can be administered to a subject as a single dose, either as a bolus or by infusion over a relatively short period of time, or it can be administered using a fractionated treatment protocol, in which the multiple doses are administered over a more prolonged period of time. One skilled in the art would know that the concentration of a compound of the present invention required to obtain an effective dose in a subject depends on many factors including, e.g., the pharmacokinetics, possible hydrolysis products, the age and general health of the subject, the route of administration, the number of treatments to be administered and the judgment of the prescribing physician. In view of these factors, the skilled artisan would adjust the dose so as to provide an effective dose for a particular use.

B. Inactivated Viruses as Vaccines

The compounds of the present invention can be used to inactivate viruses, e.g., retroviruses, such as HIV-1. In one aspect, the compounds of the present invention act by covalently attacking a nucleocapsid zinc finger, leading to disorganization of these structures and ejection of coordinated zinc ions. It will be readily apparent to those of skill in the art that once inactivated, a virus, e.g., a retrovirus, can be used, for example, as a vaccine or an immune stimulator, as a prophylactic, or as components in standard ELISA assays for the diagnosis of retroviral infections. Making use of these novel compositions and methods can involve incorporating a variety of standard procedures and reagents.

The invention provides an isolated and inactivated virus, where the virus is inactivated by a method comprising contacting the virus with a compound of the present invention, wherein contacting said virus with said compound inactivates said virus. In one embodiment the isolated and inactivated virus further comprises a vaccine formulation. A vaccine formulation of the present invention can also comprise an isolated complex of a viral protein or peptide with a compound of the present invention.

The complexed, inactivated viruses of the present invention are used in vaccine formulations that are useful for administration to mammals, e.g., humans, to treat and generate immunity to of a variety of viral diseases, particularly retroviral infections, such as HIV-1. The vaccine formulations can be given single administrations or a series of administrations. When given as a series, inoculations subsequent to the initial administration are given to boost the immune response and are typically referred to as booster inoculations.

The vaccines of the present invention contain as an active ingredient an immunogenically effective amount of a compound-complexed, inactivated, virus. Useful carriers are well known in the art, and include, e.g., thyroglobulin, albumins such as human serum albumin, tetanus toxoid, polyamino acids such as poly(D-lysine: D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are also advantageously used to boost an immune response.

C. Other Uses of Inactivated Viruses and Proteins Complexed to Compounds of the Present Invention In addition to uses as vaccines, inactivated viruses and viral proteins complexed to compounds of the present invention have a variety of other uses. For example, complexed viral proteins or inactivated viruses can be used as reagents for the detection of corresponding anti-viral antibodies. A very commonly used test to determine if an individual is infected with a virus, such as HIV, is to screen for the presence of antiviral antibodies. In one aspect of the invention, a compound-inactivated virion or complexed viral protein is used in these detection tests to, e.g., trap and detect antigens or control antigens. See, e.g., Hashida (1997) J. Clin. Lab. Anal. 11:267-286; Flo (1995) Eur. J. Clin. Microbiol. Infect. Dis. 14:504-511.

In alternative aspects of the invention, the inactivated virion orcomplexed viral protein is a crystallization reagent for X-ray crystallographic analysis or other ultrastructural studies, see, e.g., Yamashita (1998) J. Mol. Biol. 278:609-615; Wu (1998) Biochemistry 37:4518-4526. In alternative aspects of the invention, they are used as molecular weight, pI or other controls in various physicochemical experiments and methodologies.

D. Kits and Apparatus

In an additional aspect, the present invention provides kits embodying the methods and apparatus herein. Kits of the present invention comprise one or more compounds or compositions of the present invention, and, they optionally comprise one or more of the following: instructions for practicing the methods described herein, and/or for using the compound or composition; one or more assay components; a container for holding the compound, assay components, or apparatus components useful for manipulating compounds or practicing the methods herein, and/or, packaging materials.

In a further aspect, the present invention provides for the use of any compound, apparatus, apparatus component or kit herein, for the practice of any method or assay herein, and/or for the use of any apparatus or kit to practice any assay or method herein.

In a further aspect, the present invention provides for the use of any compound, composition, virus, inactivated virus or viral component, cell, cell culture, mammal, apparatus, apparatus component or kit of the present invention, for the practice of any method or assay herein, and/or for the use of any apparatus or kit to practice any assay or method herein and/or for the use of viruses, cells, cell cultures, compositions or other features herein as a medicament. The manufacture of all components herein as medicaments for the treatments described herein is also provided and apparent upon review of the foregoing.

E. Detecting the Dissociation of a Metal ion from a Zinc Finger Motif

The invention provides methods and kits to select compounds capable of dissociating a divalent ion chelated with a zinc finger motif. The motif can be an isolated peptide or polypeptide, or, it can be a substructure of a viral protein or a virion. The method includes contacting the zinc finger with a compound of the present invention, preferably an acylthiol, and subsequently detecting the dissociation of the metal ion from the zinc finger protein. The cation is commonly zinc. Any methodology known in the art can be used to detect the dissociation of the metal ion. Exemplary means include, e.g., capillary electrophoresis, immune-blotting, nuclear magnetic resonance (NMR), high performance liquid chromatography (HPLC), detecting release of radioactive zinc-65, detecting fluorescence, or detecting gel mobility shift, and other techniques which would be apparent to one of skill upon review of this disclosure. These procedures can be practiced with any protocol known in the art, which are well described in the scientific and patent literature. A few exemplary techniques are set forth below.

As the invention provides a genus of novel compounds capable of dissociating a metal ion from a zinc finger in vitro, detection of the dissociation of the metal ion identifies some of the compounds within the scope of the present invention. For example, a zinc ejection assay can be used as a screen to identify compounds within the scope of the present invention. One strategy for such screening uses the XTT cytoprotection assay to monitor anti-viral activity. Alternative strategies use a Trp37 zinc ejection assay (see, e.g., U.S. Pat. No. 6,046,228) or a N-propyl gallate (NPG) fluorescence zinc ejection assay to identify compounds of the present invention that are able to act at the cellular level, e.g., on the NCp7 protein or its Gag or Gag-Pol precursors.

Certain compounds within the scope of the invention are capable of ejecting zinc from a zinc finger at some measurable rate. The rate of this effect is not necessarily indicative of potency for antiviral activity, however. Compounds which eject zinc slowly, i.e., with slow kinetics, are preferable for some uses, especially for certain in vivo applications. A "weak cation ejector" compound of the present invention would have a zinc ejection rate of about 0.86 RFU/min, or lower, as measured by the Trp37 zinc finger fluorescence assay. A "high" ejection rate would be in the range of approximately 8 RFU/min, or higher.

1. Capillary Zone Electrophoresis (CZE)

Retroviral zinc finger proteins complex with two zinc ions, each with a formal charge of 2+. Reagents that react with the protein and remove the zinc ions cause a change in the conformation and charge of the protein. Thus, the electrophoretic mobility of the reacted protein will differ from the mobility of the unreacted protein. Changes in electrophoretic mobility of the protein can easily be detected by the standard technique of capillary zone electrophoresis (CZE). For a general description of CZE, see, e.g., Capillary Electrophoresis, Theory and Practice (Academic Press, Inc. Grossman and Colburn (eds.) (1992). Capillary zone electrophoresis has the advantage of simple automation, since many different samples can be loaded and analyzed in successive runs. Each run requires about 10 minutes and each sample tube can be analyzed multiple times. An exemplary kit utilizing CZE for analysis of compounds to be screened for CCHC zinc finger reactivity can contain about 100 µg of purified retroviral NC protein complexed with zinc in, for example, 1.0 ml of water; this could be used for the testing of approximately 1000 test compounds.

2. Release of Radioactive Zinc from Zinc-65 Labeled NCp7

Another exemplary screening method of the invention measures release of radioactive zinc from zinc-65 labeled NCp7. Purified HIV-1 NCp7 can be reconstituted with radioactive zinc-65 with a determined specific activity. By monitoring the release of radioactive zinc-65 caused by the reaction of a test compound with a retroviral NC protein, it is possible to determine the reactivity of the test compound.

A test compound can be added to a solution containing the NC protein complexed with radioactive zinc-65. Following the reaction, protein (reacted and unreacted) can be precipitated, for example, by immunoprecipitation or immunoadsorption methods using known antibodies, or by the addition of a calibrated amount of nucleic acid such that the NC protein saturates the binding sites on the nucleic acid matrix. Under conditions of low ionic strength, the saturated protein-nucleic acid complex forms a precipitate that can be removed by centrifugation. Alternatively, labeled nucleocapsid protein may be attached to a solid support, and test reagents added directly to the attached protein. Any reactions releasing zinc from the protein can be detected by the release of radioactive zinc-65 into the soluble supernatant. This general procedure can be automated depending on the equipment available. The invention provides a kit supplying retroviral nucleocapsid protein and appropriate precipitating agents for detecting the ability of test compounds to remove zinc from the protein.

3. Release of Radioactive Zinc from Zinc-65 Labeled Whole Virus

Another exemplary screening method of the invention measures release of radioactive zinc from zinc-65 labeled whole virus. Zinc is present in virus in quantities nearly stoichiometric with CCHC zinc finger arrays (Bess (1992) J. Virol. 66:840). Nearly all of the zinc is coordinated in the CCHC arrays (Summers (1992) Protein Science 1:563). Therefore, zinc released from a virus derives from zinc previously coordinated in CCHC arrays, rather than from unrelated proteins or other non-specific associations with the virion.

Purified virus can be produced from cells cultured in the presence of added zinc-65. Labeled virus can be isolated and purified by density gradient centrifugation in the presence of added EDTA to remove any unbound zinc. The purified virus can be any retrovirus of interest including, but not limited to, HIV-1, HIV-2 or SIV.

Compounds to be tested (compounds of the present invention) can be added to the purified radioactive virus under conditions appropriate for the test compound of choice (Rice 1993 Nature 361:473-475). Following the reaction, removal and/or inactivation of the reagent, the virus is disrupted by the addition of a non-ionic detergent (e.g., Triton X-100), and the viral core containing the NC protein complexed to nucleic acid is removed by centrifugation. Radioactive zinc-65 released into the supernatant indicates that the test compound penetrated the intact virus and disrupted the NC protein-zinc complex. The invention provides kits to determine whether test compounds can remove retroviral NC-chelated zinc; they can contain, inter alia, intact retrovirus particles with radioactive zinc-65 incorporated into their NC proteins, appropriate reaction buffers and a non-ionic detergent.

4. Fluorescence-Based Detection of Zinc Dissociation from Protein

Another exemplary screening method of the invention is a fluorescence-based detection of zinc dissociation from protein. This method measures changes in the intrinsic fluorescence of aromatic protein moieties. It is commonly used to monitor a reaction which involves a change in protein conformation. In the present invention, fluorescence can be used to monitor the loss of metal ion from a zinc finger, e.g., the loss of zinc from a CCHC retroviral zinc finger protein, after contact with a compound of the present invention. The intrinsic fluorescence of Trp 37 in the second zinc finger of HIV-1 NC protein can be used to monitor nucleic acid binding and conformation of the zinc finger complex.

Zinc ejection is measured by the ability of compounds to chemically attack the cysteines in purified NCp7 protein resulting in a loss of fluorescence due to the movement of the tryptophan 37 residue from an exposed to an internal position on the protein. Zinc ejection can be measured and expressed as either percent decrease in total fluorescence or decrease in relative fluorescence units per min during a 30 min assay (RFU/min). A compound is considered within the scope of the invention if any amount of zinc ejection is detected.

Artificial fluorescent probes can also be incorporated into a protein to provide for the detection of changes in conformation. Poly ethino-adenine, e.g., can be used as a fluorescent nucleotide to measure the extent of interaction between a compound of the present invention and a zinc finger (see, Karpel (1987) J. Biol. Chem 262:4961). Finally, a variety of known fluorescent zinc chelators capable of complexing liberated zinc may be used to monitor zinc loss. By monitoring the release of zinc from the CCHC zinc finger arrays, the effect of a given reagent may be determined (Rice (1996) *J Med. Chem.* 39:3606-3616; Rice (1996) *Science* 270:1194-1197).

5. Detection of Disulfide Cross-Linked NC Protein by Gel-Mobility Shift Assays

Another exemplary screening method of the invention involves detection of disulfide cross-linked NC protein by Gel-Mobility Shift Assays. Purified concentrated retrovirus and antisera against the purified NC protein of the virus can be used to test the ability of a specific compound to penetrate the virus and react with the NC protein by forming disulfide complexes in the core of the virus. Compounds are mixed with the whole retrovirus under reaction conditions appropriate for each compound. The virus is then removed from the reagent by centrifugation and disrupted in, e.g., standard SDS-PAGE sample buffer with (reduced) and without (non-reduced) 2-mercaptoethanol. The viral proteins are then separated by standard SDS--PAGE and the sample examined for the presence or absence of the monomeric zinc finger protein in the non-reduced sample. Depending upon the virus used in the experiment and the conditions of electrophoresis, the zinc finger protein can be visualized by protein staining methods, or by immuno-blot methods. Compounds which react with the zinc finger protein by attacking the zinc finger complexes and forming disulfide cross-linked products inactivate the virus. Thus, compounds of interest (i.e., those which cause cross-linking), including the compounds of the present invention, reduce the amount of monomeric zinc finger protein detected.

The treated virions can also be tested for infectivity. The virions are suspended in media (rather than solubilized) and added to target cells. The cultures are then examined to determine whether the virions are still active. To determine whether the treated virus particles are active, the cells are monitored for the presence of intracellularly-synthesized viral RNA using, for example, the polymerase chain reaction (PCR) (Rice (1993) Proc. Natl. Acad. Sci. USA 90:9721; Turpin (1996) J. Virol. 70:6180). Alternatively, cytoprotection assays can be used (Weislow (1993) J. Natl. Cancer Inst. 81:577). An example of a compound which can be used as a control in the gel mobility shift assay is azodicarbonamide (ADA), a compound which is commercially available from the Aldrich Chemical Company (Milwaukee, Wis.). ADA also inactivates HIV-1 virus, as determined using the PCR assay described above.

The invention provides a kit incorporating the gel-mobility shift concept to screen the compounds of the present invention for various activities. For example, it can be used to identify and study compounds which are able to penetrate intact virus and to induce disulfide cross-links in the viral zinc finger proteins. An exemplary kit would contain, for example, purified concentrated retrovirus and appropriate size standards to monitor the change in mobility through the gel due to disulfide cross-linking.

6. High Performance Liquid Chromatography of Purified NC Proteins for Structural Characterization of Reaction Products Another exemplary screening method of the invention uses high performance liquid chromatography (HPLC) of purified NC proteins for structural characterization of proteins reacted with the compounds of the present invention. For example, highly purified retroviral zinc finger proteins can be produced by expression from vectors generated through recombinant DNA technology. These proteins, when reconstituted with zinc, as described by Summers (1992) Protein Science 1:563-567, provide the source of the NC proteins containing the zinc fingers that are the targets for attack by compounds of the present invention. When the zinc finger proteins react with identified compounds, the reaction produces a covalent change in the zinc finger protein, and the modified protein can be separated from the unreacted protein by, for example, reversed phase HPLC.

The purified proteins and these separation methods are used to obtain sufficient modified protein (i.e., products of the reaction) for chemical and structural analysis. The purified reaction products are isolated and their structures determined by standard N-terminal Edman degradation. However, for any specific reagent, the gradients and HPLC conditions will depend upon the NC protein and the reaction products. This procedure can be used to identify compounds which react with HIV-1 zinc fingers. The invention provides kits standardizing these techniques; they may contain, for example, purified retroviral zinc finger proteins.

7. Nuclear Magnetic Resonance (NMR)-Based Detection of Zinc Loss

Another exemplary screening method of the invention uses NMR to monitor the loss of zinc from a protein upon contact with a compound of the present invention, e.g., a retroviral zinc finger protein (see, e.g., Rice (1993) Nature 361:473-475; McDonnell (1997) J. Med. Chem. 40:1969; Rice (1997) Nature Medicine 3:341-345). One of skill is familiar with the general technique of NMR and its many applications to monitor protein-ligand interactions. Briefly, the atoms in retroviral zinc finger proteins bound to zinc share a different local environment than zinc finger proteins that lack zinc. The difference in local environment leads to distinct NMR spectra for protein molecules that bind zinc, versus those that do not. By monitoring, for example, the proton (1H) spectrum of a sample containing metal ion-chelated zinc finger protein and a compound of the present invention over time, it is possible to measure whether the compound causes the protein to loose its zinc ion. Since NMR can be used to provide the percent of protein molecules that are bound to zinc over time, it is also possible to use this technique to define the reaction kinetics of a given reaction. Similarly, NMR may be used to monitor the effect of test compounds upon the binding of zinc finger proteins to nucleic acid complexes. The invention provides kits containing e.g., purified retroviral zinc finger proteins and oligonucleotides, in addition to the compounds of the present invention, to standardize the practice of this method.

V. General Methods

A. Detection of Antiviral Activity

Certain compounds within the scope of the present invention have displayed antiviral activity (i.e., any ability to decrease or diminish the transmission of or the replicative capacity of a virus). The antiviral activity of these compounds can be determined empirically by clinical observation or objectively using any in vivo or in vitro test or assay, e.g. the XTT cytoprotection assay (described herein), measuring Tat-induced activity (as in the HeLa-CD4-LTR-beta-gal (MAGI cells) assay and detecting Tat-induced beta-galactosidase activity, see, e.g., Tokunaga (1998) J. Virol. 72:6257-6259), and the like.

One exemplary means to determine antiviral activity is with CEM-SS cells and virus (e.g., HIV-1RF) (MOI=0.01) using the XTT (2,3-bis[2-methoxy-4-nitro-5-sulfophenyl]-5-

[(phenylamino)carbonyl]-2H-tetrazolium hydroxide) cytoprotection assay, as described by Rice (1993) PNAS 90:9721-9724, and Rice (1997) Antimicrob. Agents Chemother. 41:419-426. Briefly, cells are infected with HIV-1RF (or other virus to be tested) in the presence of various dilutions of test compounds or control compounds. The cultures are incubated for seven days. During this time, control cultures without protective compounds (i.e., compounds with anti-viral activity) replicate virus, induce syncytia, and result in about 90% cell death. The cell death is measured by XTT dye reduction. XTT is a soluble tetrazolium dye that measures mitochondrial energy output, similar to MTT. Positive controls using dextran sulfate (an attachment inhibitor) or 3'-azido-2', 3'-dideoxythymidine, AZT (a reverse transcriptase inhibitor) are added to each assay. Individual assays are done in duplicate using a sister plate method. Effective antiviral concentrations providing 50% cytoprotection ($EC_{50}$), and cellular growth inhibitory concentrations causing 50% cytotoxicity ($IC_{50}$) are calculated. Activity data using this assay for selected compounds of the present invention are presented in Table 1 below.

Alternatively, any virus can be grown in culture, or in an in vivo (animal) model, in the presence or absence of a compound or a compound-containing pharmaceutical formulation to test for anti-viral, viral transmission-inhibiting activity and efficacy. Any virus, assay or animal model which would be apparent to one of skill upon review of this disclosure can be used, see, e.g., Lu (1997) Crit. Rev. Oncog. 8:273-291; Neildez (1998) Virology 243:12-20; Geretti (1998) J. Gen. Virol. 79:415-421; Mohri (1998) Science 279:1223-1227; Lee (1998) Proc. Natl. Acad. Sci. USA 95:939-944; Schwiebert (1998) AIDS Res. Hum. Retroviruses 14:269-274.

For in vitro assays, any measurable decrease in the viral load of a culture grown in the presence of a compound test compound as compared to a positive or negative control compound is indicative of an anti-viral, transmission-inhibiting effect. Generally, between 10% and 99% reduction in viral load is observed, but typically a reduction of at least 30% is considered significant. Any relevant criteria can be used to evaluate the antiviral efficacy of a compound of the present invention or its composition or formulation.

B. Cloning and Expression of Retroviral Nucleocapsid Proteins

Certain compounds of the present invention are capable of dissociating a metal ion from a zinc finger in vitro. Zinc finger containing proteins are used to detect the dissociation of a metal ion from a zinc finger motif and in the methods and kits of the present invention. General laboratory procedures for the cloning and expression of zinc finger motifs and proteins containing these motifs can be found, e.g., current editions of Sambrook, et. al., Molecular Cloning A Laboratory Manual (2nd Ed.), Vol. 1-3, Cold Spring Harbor Laboratory, Cold Spring Harbor, New York, 1989; CURRENT PROTOCOLS IN MOLECULAR BIOLOGY, Ausubel, ed. Greene Publishing and Wiley-Interscience, New York (1987). Sequences and sources of zinc fingers, including nucleic acids, proteins and viral sources, are publicly available, for example, through electronic databases, such as, e.g., The National Center for Biotechnology Information at http://www.ncbi.nlm.nih.gov/Entrez/, or, The National Library of Medicine at http://www.ncbi.nln.nih.gov/PubMed/.

The nucleic acid compositions that may be used to express zinc finger-containing proteins, whether RNA, cDNA, genomic DNA, or a hybrid of the various combinations, can be isolated from natural sources, or may be synthesized in vitro. Recombinant DNA techniques can be used to produce polypeptides. In general, the DNA encoding the polypeptide or peptide of interest are first cloned or isolated in a form suitable for ligation into an expression vector. After ligation, the vectors containing the DNA fragments or inserts are introduced into a suitable host cell for expression of the recombinant polypeptides. The polypeptides are then isolated from the host cells. The nucleic acids may be present in transformed or transfected whole cells, in a transformed or transfected cell lysate, or in a partially purified or substantially pure form. Techniques for nucleic acid manipulation of genes encoding zinc finger-containing proteins, such as subcloning nucleic acid sequences into expression vectors, labeling probes, DNA hybridization, and the like are described, e.g., in Sambrook and Ausubel, supra.

Once the DNAs are isolated and cloned, one can express the desired polypeptides in a recombinantly engineered cell such as bacteria, yeast, insect, or mammalian cells. One of skill in the art is knowledgeable in the numerous expression systems available for expression of the recombinantly produced proteins.

C. Evaluating activity in vivo

Compounds of the present invention are often highly active against simian immunodeficiency virus (SIV). Such compounds can be utilized for the treatment of SIV infections in, for example, macaque monkeys. This activity provides an ideal model for use in the optimization of formulations and administration regimens.

Alternatively, any virus can be grown in culture, or in an in vivo (animal) model, in the presence or absence of a compound of the present invention or a formulation containing such compound to test for antiviral, viral transmission-inhibiting activity and efficacy. Any virus, assay or animal model, which would be apparent to one of skill upon review of this disclosure, can be used, see, e.g., Lu (1997) Crit. Rev. Oncol. 8: 273-291; Neildez (1998) Virology 243: 12-20; Geretti (1998) J. Gen Virol 79: 415-421; Mohri (1998) Science 279: 1223-1227; Lee (1998) Proc. Natl. Acad. Sci. USA 95: 939-944; Schwiebert (1998) AIDS Res & Hum. Retroviruses 14: 269-274.

VI. EXAMPLES

The following examples describe ways to practice the present invention. They are in no way intended to limit the scope of the present invention, and variations of these procedures that would be obvious to persons of ordinary skill in the art are intended to be included in the invention.

A. Synthesis of compounds

Compounds of the present invention, including intermediates used in the making of these compositions, such as disulfides, can be synthesized by any method known in the art, see, e.g., Beilstein Handbook of Organic Chemistry, supra; Gilman, et al, supra. The following are exemplary synthetic protocols:

1. Example 1

Synthesis of 2,2'-dithiobis(5-chlorobenzoic acid)

A freshly made solution of sodium disulfide ($Na_2S_2$) was prepared as follows: A mixture of sodium sulfide ($Na_2S.9H_2O$) (15.40 g, 64.1 mmol) and powdered sulfur (2.06 g, 64.1 mmol) in 50 ml water was heated and efficiently stirred to dissolve the sulfur. A solution of sodium hydroxide (2.33 g, 58.3 mmol) in 30 ml water was then added to the hot solution, and the mixture was cooled to 0° C.

To a solution of 2-amino-5-chlorobenzoic acid (10 g, 58.3 mmol) in 50 ml water was added 6 M hydrochloric acid (23.3 ml, 139.9 mmol). The mixture was cooled to 0° C., and a chilled solution of 2.0 M sodium nitrite (29.1 ml, 58.2 mmol) was added gradually while maintaining the temperature below 5° C.

To the alkaline solution of sodium disulfide was added the above diazotized solution with constant stirring, at a temperature below 5° C. The mixture was allowed to warm to room temp. and was stirred overnight. The solution was acidified with 6 M hydrochloric acid (21 ml, 126 mmol) until the pH was less than 2. The precipitate thus obtained was filtered and washed with water.

In order to remove excess sulfur, the precipitate was dissolved by boiling with a solution of anhydrous sodium carbonate $Na_2CO_3$ (3.52 g, 33.2 mmol) in 30 ml water (pH ~8.1). The undissolved material was filtered off and washed with hot water. The filtrate and washes were acidified in order to reprecipitate the product. The product was filtered off and crystallized from ethanol. Yield: 9.0 g (82.3%). TLC (EM silica on glass) showed one spot (UV), using chloroform-ethyl acetate 7:3 v/v as the mobile phase. $^1$H NMR(DMSO-$d_6$): 7.26(d, 2H, Ar—H), 7.34(d, 2H, Ar—H), 7.98(s, 2H, Ar—H), 13.96 (brs, 2H, COOH).

2. Example 2

Synthesis of 3,3'-dithiobis(benzoic acid)

This disulfide was prepared from 3-aminobenzoic acid using the same procedure as described above.
$^1$H NMR(DMSO-$d_6$): 7.24-7.32(m, 2H, Ar—H), 7.36(d, 2H, Ar—H), 7.44(d, 2H, Ar—H), 8.04(s, 2H, Ar—H), 13.08 (brs, 2H, COOH).

3. Example 3

Synthesis of 2,2'-dithiobis(nicotinoyl chloride)

A mixture of 2-mercaptonicotinic acid (1.0 g, 6.45 mmol), toluene (10 ml) and thionyl chloride (5 ml) was refluxed for 3 h. The yellow product, which crystallized out on cooling, was collected and washed with carbon disulfide and then with chloroform; mp, 212-214° C., yield 85%. $^1$H NMR(DMSO-$d_6$): 7.26-7.32(m, 2H, H-5 &H-5'), 8.26(d, 2H, H-6&H-6'), 8.52(d, 2H, H-4&H-4').

4. Example 4

Synthesis of Di-N-succinimidyl 2,2'-dithiobis(benzoate)

To a solution of 2,2'-dithiosalicylic acid (2.0 mmol) in a mixture of THF (14 ml) and 2-propanol (6 ml) was added N-hydroxysuccinimide (4.4 mmol) and 1,3-diisopropylcarbodiimide (4.1 mmol). The solution was stirred at room temp. for 4 h. The white precipitate (product) thus obtained was filtered and washed with 2-propanol (20 ml) in portions, yielding di-N-succinimidyl 2,2'-dithiobis(benzoate) (89%).
$^1$H NMR(DMSO-$d_6$): 3.0(s, 8H, 4CH$_2$), 7.52-7.64(m, 2H, Ar—H), 7.80-7.94(m, 4H, Ar—H), 8.32(d, 2H, Ar—H).

5. Example 5

Synthesis of Di-N-succinimidyl 3,3'-dithiobis(benzoate)

This compound was prepared from 3,3'-dithiobis(benzoic acid) in the same manner as the above, 2,2' isomer. $^1$H NMR (DMSO-$d_6$): 2.90(s, 8H, 4CH$_2$), 7.70(t, 2H, Ar—H), 7.96-8.06(m, 4H, Ar—H), 8.22(s, 2H, Ar—H).

6. Example 6

Synthesis of Di-N-succinimidyl 2,2'-dithiobis(5-chlorobenzoate)

This compound was prepared from 2,2'-dithiobis(5-chlorobenzoic acid) in the same manner as for the above derivatives. $^1$H NMR(DMSO-$d_6$): 2.92(s, 8H, 4CH$_2$), 7.74(d, 2H, Ar—H), 7.86(d, 2H, Ar—H), 8.24(s, 2H, Ar—H).

7. Example 7

Synthesis of Di-N-succinimidyl 2,2'dithiobis(nicotinoate)

A mixture of crude 2,2'-dithiobis(nicotinoyl chloride) (0.35 g, 1.0 mmol), N-hydroxysuccinimide (0.26 g, 2.2 mmol), diisopropylcarbodiimide (0.33 ml, 2.1 mmol, added to activate free carboxyl groups present in the crude bis-acid chloride), THF (9 ml) and 2-propanol (4 ml) was stirred overnight. The precipitated product was collected and washed with 2-propanol (15 ml) and dried in vacuo. Yield: 80%. $^1$H NMR(DMSO-$d_6$): 2.94(brs, 8H, 4CH$_2$)7.47-7.52(m, 2H, H-5&H-5), 8.58(d, 2H, H-6&H-6'), 8.76(d, 2H, H-4&H-4').

8. Example 8

Synthesis of N-Benzyloxycarbonyl (Z)-β-alanine amide

A well stirred solution of Z-β-alanine (11.72 g, 52.6 mmol) and N-methylmorpholine (5.88 ml, 52.5 mmol) in 300 ml CH$_2$Cl$_2$ was cooled to −20° C., and. isobutyl chloroformate (6.6 ml, 50.0 mmol) was added. After being stirred for 20 min, 2.0 M ammonia in 2-propanol (30 ml, 60 mmol) was added gradually at −20° C. with constant stirring. The pure product was isolated by extraction with dichloromethane/water. Yield, 6.0 g (55%); melting point, 130-131° C.

Z-D-Alanine amide was prepared in like manner as P-alanine amide.

9. Example 9

Synthesis of N,N'-(2,2'-Dithiobisbenzoyl)bis(β-alaninamide)

Z-βalaninamide (5.11 g, 23 mmol) was dissolved in 100 ml methanol under nitrogen atmosphere, and 10% Pd/C (11% of the sample weight, 0.60 g) was suspended in 40 ml of methanol and added The mixture was hydrogenated at 1 atm for 3 h. TLC was used to check for complete removal of the Z group. The Pd/C was filtered off and the filtrate was rotary evaporated to give an oily residue(~2.18 g). The residue was diluted with 50 ml DMF, di-N-succinimidyl 2,2'-dithiobis(benzoate) (5.01 g, 10 mmol) was added, and the reaction mixture was stirred overnight. The DMF was rotary evaporated and 50 ml of water was added to the residue. The precipitate obtained was filtered and dried over CaCl$_2$. Yield: 3.91 g (87%); $^1$H NMR (DMSO-$d_6$): 2.44(t, 4H, 2CH$_2$), 3.46(q, 4H, 2CH$_2$),

10. Example 10

Synthesis of N,N'-(2,2'-Dithiobisnicotinoyl)bis(glycinamide)

To a mixture of di-N-succinimidyl 2,2'-dithiobis(nicotinoate) (0.50 g, 1 mmol), glycinamide hydrochloride (0.33 g, 3, mmol) and triethylamine (0.4 ml, 3 mmol) in DMF (5 ml) was stirred for 8 hr. After completion of the reaction, the solvent was evaporated to dryness and diluted with water. The precipitate thus obtained was filtered and dried over $CaCl_2$. Yield: 85%. $^1$H NMR(DMSO-$d_6$): 3.85(d, 4H, 2CH$_2$), 7.13 (brs, 2H, 2NH$_2$), 7.26-7.30(m, 2H, H-5&H-5'), 7.47(brs, 2H, 2NH$_2$), 8.12(d, 2H, H-6&H-6'), 8.48(d, 2H, H-4&H-4'), 8.99 (t, 2H, 2NH).

11. Example 11

Synthesis of N-(2-Mercaptobenzoyl)-β-alaninamide

To the mixture of N,N'-(2,2'-dithiobisbenzoyl)bis(β-alaninamide) (2.00 g, 4.5 mmol) in DMF (18 ml) and water (2 ml) was added tris(2-carboxyethyl)phosphine hydrochloride (TCEP.HCl) (1.5 g, 5.2 mmol) and triethylamine (0.50 ml, 4.6 mmol). The mixture was stirred at room temp. for 1 h and then added to ethyl ether (200 ml). The precipitate was collected, washed with water (3×20 ml) and dried under vacuum to yield 1.56 g (77%) of the title compound. $^1$H NMR (DMSO-$d_6$): 2.40(t, 2H, CH$_2$), 3.42(q, 2H, CH$_2$), 5.40 (s, 1H, SH), 6.90(s, 1H, NH$_2$), 7.20(t, 1H, Ar—H), 7.33(t, 1H, Ar—H), 7.40-7.55 (m, 3H, Ar—H&NH$_2$), 8.48(t, 1H, NH).

12. Example 12

Synthesis of N-(1,2-dihydro-2-thioxonicotinoyl)glycinamide

To a stirred suspension of N,N'-(2,2'-dithiobisnicotinoyl) bis(glycinamide) (0.42 g, 1.0 mmol) in 1.0 M HCl (5 ml) was added slowly sodium metabisulfite (0.5 g, 5 mmol), dissolved in about 1 ml of water. The mixture was stirred at room temp. for 1 h, and the solid material was collected by filtration and dried over $CaCl_2$. Yield: 90%. $^1$H NMR(DMSO-$d_6$): 3.91(d, 2H, CH$_2$), 7.0(t, 1H, H-5), 7.14(brs, 1H, NH$_2$), 7.50(brs, 1H, NH$_2$), 7.94(t, 1H, H-6), 8.37(d, 1H, H-4), 10.65(t, 1H, NH), 14.10 (brs, 1H, NH).

13. Example 13

Synthesis of N-[2-(terf-Butylcarbamylthio)benzoyl]-β-alaninamide

To a well stirred mixture of N-(2-mercaptobenzoyl)-β-alaninamide (0.45 g, 2.0 mmol) in 8 ml DMF was added tert-butyl isocyanate (3.0 mmol). The reaction mixture was stirred for 8-10 h at room temp. After completion of the reaction, all of the DMF was removed in vacuo and the residue was treated with ethyl ether. The white precipitate that formed was washed with water, dried in vacuo/$CaCl_2$ and crystallized from acetonitrile. Yield: 89%. $^1$H NMR (DMSO-$d_6$): 1.30(s, 9H, 3CH$_3$), 2.38(t, 2H, CH$_2$), 3.40(q, 2H, CH$_2$), 6.86(brs, 1H, NH$_2$), 7.30-7.60(m, 5H, Ar—H, NH$_2$), 8.06(s, 1H, NH), 8.26(t, 1H, NH).

14. Example 14

Synthesis of N-[2-(2-Bromoethylcarbamylthio)benzoyl]-β-alaninamide

To a solution of N-(2-mercaptobenzoyl)-β-alaninamide (0.90 g, 4.0 mmol) in DMF (20 ml) was added 2-bromoethyl isocyanate (0.91 g, 6.0 mmol). The reaction mixture was stirred for 6 h. The solvent was evaporated to dryness, and the residue was treated with ethyl ether (20 ml) with vigorous stirring. The precipitate obtained was filtered, washed with water and dried over $CaCl_2$. Yield: 87%. $^1$H NMR (DMSO-$d_6$): 2.36(t, 2H, CH$_2$), 3.42(q, 2H, CH$_2$), 3.54(s, 4H, 2CH$_2$), 6.88(brs, 1H, NH$_2$), 7.36-7.66(m, 5H, Ar—H, NH$_2$), 8.26(t, 1H, NH), 8.66(brs, 1H, NH).

15. Example 15

Synthesis of N-[2-(2-Pyridinioethylcarbamylthio) benzoyl]-β-alaninamide bromide

A solution of N-[2-(2-bromoethylcarbamylthio)benzoyl]-β-alaninamide (0.37 g, 1.0 mmol) in pyridine (5 ml) was stirred for 8 h under nitrogen. The pyridine was removed in vacuo, and the crude product was purified by column chromatography on silica using chloroform-methanol(7:3 v/v) as eluent. Yield: 82%. $^1$H NMR (DMSO-$d_6$): 2.38(t, 2H, CH$_2$), 3.40(q, 2H, CH$_2$), 3.72(q,2H, CH$_2$), 4.72(t, 2H, CH$_2$), 6.92 (brs, 1H, NH$_2$), 7.36-7.58(m, 5H, Ar—H, NH$_2$), 8.26(t, 2H, Py-H), 8.36(t, 1H, NH), 8.66(t, 1H, Py-H), 9.12(d, 2H, Py-H).

16. Example 16

Synthesis of N-[2-(2-Bromoethyloxycarbonylthio) benzoyl]glycinamide

To a solution of N-(2-mercaptobenzoyl)glycinamide (1.05 g, 5.0 mmol) in N,N-dimethylcaetamide (DMA, 25 ml) was added 2-bromoethyl chloroformate (1.22 g, 6.5 mmol). The reaction mixture was stirred for 8 h, the solvent was evaporated to dryness, and the residue was triturated with ethyl ether (25 ml. The resulting precipitate was filtered, washed with water and dried over $CaCl_2$ Yield: 89%. $^1$H NMR (DMSO-$d_6$): 3.71(t, 1H, CH$_2$), 3.78(d, 2H, CH$_2$), 3.86(t, 1H, CH$_2$), 4.45(t, 1H, CH$_2$), 4.51(t, 1H, NH$_2$), 7.30(brs, 1H, NH$_2$), 7.36-7.58(m, 5H, Ar—H, NH$_2$), 8.26(t, 2H, Py-H), 8.36 (t, 1H, NH), 8.52(t, 1H, NH), 8.66(t, 1H, Py-H), 9.12(d, 2H, Py-H).

17. Example 17

Synthesis of N-[2-(iso-Butyloxycarbonylthio)benzoyl]-L-alaninamide

To a solution of N-(2-mercaptobenzoyl)-L-alaninamide (0.22 g, 1.00 mmol) in DMA (5 ml) was added iso-butyl chloroformate (0.2 g, 1.50 mmol), and the mixture was stirred for 8 h. The solvent was evaporated to dryness, and the residue was triturated with ethyl ether (25 ml). The precipitate obtained was filtered, washed with water and dried over $CaCl_2$. Yield, 73%. The product was further purified by column chromatography on silica using chloroform-methanol (7:3 v/v) as eluent with 82% recovery. $^1$H NMR (DMSO-$d_6$): 0.94(d, 6H, 2CH$_3$), 1.34(d, 3H, CH$_3$), 1.96(m, 1H, CH), 4.06 (d, 2H, CH$_2$), 4.44quintet, 1H, CH), 7.16(brs, 1H, NH$_2$), 7.38(brs, 1H, NH$_2$), 7.54-7.80(m, 4H, Ar—H), 8.42(d, 1H, NH).

18. Example 18

Synthesis of N-[2-(Methylthioimidothio)benzoyl]--alaninamide

A mixture of N-(2-mercaptobenzoyl)-β-alaninamide (0.45 g, 2.00 mmol) and methyl thiocyanate (0.22 g, 3.00 mmol) in DMF (10 ml) was heated at 60° C. for 20 h. The solvent was removed in vacuo and the resulting residue was treated with ethyl ether. The precipitate obtained was collected, and pure product was isolated by column chromatography on silica using chloroform as eluent. Yield, 83%. $^1$H NMR (DMSO-$d_6$): 2.30-2.50(m, 5H, $CH_2$ & $CH_3$), 3.44(q, 2H, $CH_2$), 6.90 (brs, 1H, $NH_2$), 7.36(t, 2H, Ar—H, 7.44(brs, 1H, $NH_2$), 7.56-7.70(m, 2H, Ar—H), 8.02(d, 1H, NH), 8.60(t, 1H, NH).

19. Example 19

Synthesis of N-[2-(Ethylthiocarbonylthio)benzoyl]-D-alaninamide

To a solution of N-(2-mercaptobenzoyl)-D-alaninamide (0.22 g, 1.00 mmol) in DMF (5 ml) was added ethyl chlorothiolformate (0.19 g, 1.50 mmol) and the mixture was stirred for 8 h. The solvent was evaporated to dryness, and the resulting residue was treated with ethyl ether (25 ml) with vigorous stirring. The precipitate obtained was filtered, washed with water and dried over $CaCl_2$. Yield, 73%. The product was further purified by column chromatography using chloroform-methanol(7:3 v/v) as eluent with 82% recovery. $^1$ H NMR (DMSO-$d_6$): 1.24(t, 3H, $CH_3$), 1.34(d, 3H, $CH_3$), 3.0(q, 2H, $CH_2$), 4.40(quintet, 1H, CH), 7.14(brs, 1H, $NH_2$), 7.36 (brs, 1H, $NH_2$), 7.50-7.76(m, 4H, Ar—H), 8.4(d, 1H, NH).

B. Antiviral Activity of Compounds of the Invention

The invention provides methods for inactivating viruses, and, compositions comprising inactivated viruses, including, e.g., vaccine pharmaceutical compositions. The compounds of the present invention were demonstrated to have viral inactivating activity in mechanistic and target-based assays.

For in vitro assays, any measurable decrease in the viral load of a culture grown in the presence of a test compound as compared to a positive or negative control compound is indicative of an antiviral, transmission-inhibiting effect. Typically, at least a 30% reduction in viral load is observed, generally, between 10% and 99%. As discussed in the above definition section, any relevant criteria can be used to evaluate the antiviral efficacy of a composition or formulation containing a compound of the present invention.

1. Example 20

XTT Assay

A compound is within the scope of the invention if it displays any antiviral activity (i.e., any ability to decrease or diminish the transmission of or the replicative capacity of a virus). The antiviral activity can be determined empirically by clinical observation or objectively using any in vivo or in vitro test or assay, e.g., the XTT cytoprotection assay (described herein), measuring Tat-induced activity (as in the HeLa-CD4-LTR-beta-gal (MAGI cells) assay and detecting Tat-induced beta-galactosidase activity, see, e.g., Tokunaga (1998) J. Virol. 72: 6257-6259, and the like. A compound with any degree of measurable antiviral activity is within the scope of the invention even if no metal ion dissociation occurs or no metal ion dissociation is detectable.

One exemplary means to determine antiviral activity is with CEM-SS cells and virus (e.g., HIV-1RF) (MOI=0.01) using the XTT {2,3-bis[2-methoxy-4-nitro-5-sulfophenyl]-5- -[(phenylamino)carbonyl]-2H-tetrazolium hydroxide} cytoprotection assay, as described by Rice (1993) Proc. Natl. Acad. Sci. USA 90: 9721-9724, and Rice (1997) Antimicrob. Agents & Chemother. 41: 419-426. Briefly, cells are infected with HIV-1RF (or other virus to be tested) in the presence of various dilutions of test compounds and controls. The cultures are incubated for seven days. During this time, control cultures without protective compounds (i.e., compounds with antiviral activity) replicate virus, induce syncytia, and result in about 90% cell death. The cell death is measured by XTT dye reduction. XTT is a soluble tetrazolium dye that measures mitochondrial energy output, similar to MTT. Positive controls using dextran sulfate (an attachment inhibitor) or 3'-azido-2,3-dideoxythymidine, AZT (a reverse transcriptase inhibitor), are added to each assay. Individual assays are done in duplicate using a sister plate method. Effective antiviral concentrations providing 50% cytoprotection ($EC_{50}$), and cellular growth inhibitory concentrations causing 50% cytotoxicity ($IC_{50}$) are calculated. Table 1 provides activity data for illustrative compounds of the present invention. Compound numbers therein refer to the numbers used in FIG. 1.

TABLE 1

ANTIVIRAL ACTIVITY USING XTT ASSAY

| Compound Number | $EC_{50}$ (μM) | $IC_{50}$ (μM) | Therapeutic Index |
|---|---|---|---|
| 1 | 4.0 | 35.9 | 9.1 |
| 3 | >10 | 10.6 | — |
| 5 | 5.1 | 127.5 | 25 |
| 8 | 3.3 | 676 | 205 |
| 9 | 2.7 | 790 | 298 |
| 10 | 3.8 | >200 | >53 |
| 11 | 6.9 | 165 | 24 |
| 12 | 8.1 | 102 | 13 |
| 13 | 3.7 | 42 | 11 |
| 14 | 2.6 | 666 | 251 |
| 15 | >10 | >200 | — |
| 17 | >100 | 112 | — |
| 18 | 149 | >1000 | >6.7 |
| 19 | 2.9 | 461 | 161 |
| 20 | 3.6 | 135 | 38 |
| 21 | 5.2 | 197 | 38 |
| 22 | 9.7 | 22 | 2.3 |
| 23 | 4.5 | 107 | 24 |
| 24 | — | >200 | — |
| 25 | 31.8 | 573 | 18 |
| 26 | 2.5 | 35 | 14 |
| 77 | 1.37 | 230 | 168 |
| 78 | 1.58 | 57 | 36 |
| 80 | 3.07 | 200 | 65 |
| 81 | 2.07 | 200 | 97 |
| 82 | 2.94 | 200 | 68 |
| 83 | 2.16 | 128 | 59 |
| 84 | 2.36 | 64.4 | 27 |
| 85 | 0.72 | 110 | 153 |
| 86 | 0.8 | 112 | 140 |
| 87 | 0.71 | 11.4 | 16 |
| 88 | 0.48 | 9 | 19 |
| 89 | 0.92 | 8 | 8.7 |
| 90 | 0.97 | 200 | 206 |
| 91 | 1.58 | 138 | 87 |
| 92 | 0.95 | 153 | 161 |
| 93 | — | >316 | — |
| 94 | 0.5 | 70 | 140 |
| 95 | 0.85 | 22.6 | 27 |
| 96 | 1.32 | 27.5 | 21 |
| 97 | 0.55 | 29 | 53 |
| 98 | 0.47 | 130 | 277 |
| 99 | 1.19 | 23.1 | 19 |
| 100 | 0.45 | 128 | 284 |

TABLE 1-continued

ANTIVIRAL ACTIVITY USING XTT ASSAY

| Compound Number | EC$_{50}$ (μM) | IC$_{50}$ (μM) | Therapeutic Index |
|---|---|---|---|
| 101 | 1.36 | >316 | 232 |
| 102 | 5.21 | >316 | 60.6 |
| 103 | 3.34 | 254 | 76 |
| 104 | 1.16 | 186 | 160 |
| 105 | 1.6 | >316 | 198 |
| 106 | 1.89 | >316 | 167 |
| 107 | 3.96 | >316 | 79.8 |
| 108 | 7.05 | >316 | 45 |
| 109 | 9.55 | >316 | 33 |
| 110 | 1.53 | 5.23 | 3.4 |
| 111 | 0.48 | 4.9 | 10 |
| 112 | 1.05 | 5.2 | 5 |
| 113 | 0.69 | 103 | 148 |
| 114 | 0.42 | 86 | 203 |
| 115 | 0.59 | 117 | 196 |
| 116 | 0.53 | 77.6 | 147 |
| 117 | 0.51 | 32.2 | 64 |
| 118 | 0.53 | 38.7 | 74 |
| 119 | 0.30 | 54.4 | 179 |
| 120 | 0.50 | 11.2 | 23 |
| 121 | 0.76 | 81 | 107 |
| 122 | 0.43 | 39.4 | 92 |
| 123 | 0.23 | 38.3 | 167 |
| 124 | 0.16 | 40.2 | 251 |
| 125 | 0.77 | 76 | 98.6 |
| 126 | 0.33 | 55.1 | 167 |
| 127 | 0.36 | 125 | 347 |
| 128 | 0.37 | 142 | 384 |
| 129 | 0.55 | 11.9 | 21.6 |
| 130 | 304 | 37 | 0.12 |
| 131 | 0.45 | 35.8 | 80 |
| 132 | 0.81 | NA | — |
| 133 | — | 20 | — |
| 134 | 3.75 | 20 | 5.3 |
| 135 | — | 20 | — |
| 136 | 0.70 | 20 | 28.6 |
| 137 | 0.71 | 20 | 28.2 |
| 138 | 0.63 | 20 | 31.7 |
| 139 | 0.53 | 20 | 37.7 |
| 140 | 1.6 | 11.3 | 7.1 |
| 141 | 1.13 | 20 | 17.7 |
| 142 | 6.9 | 20 | 2.9 |

2. Example 21

Activity Against Resistant HIV Mutants

Using the same XTT assay, certain compounds of the present invention were tested against HIV mutants that have reduced susceptibility to current treatments, such as AZT. Data for selected compounds against two HIV mutations are presented in Table 2, which inlcudes AZT as a control. Note that the EC50 for compounds of the present invention is often similar between the two HIV strains, while the first strain is approximately 200-fold less sensitive to AZT.

TABLE 2

Activity against drug resistant HIV mutants.

| Compound No. | EC$_{50}$ (μM) | IC$_{50}$ (μM) | TI |
|---|---|---|---|
| HIV-1 144-44/PBMCs: mutation L10I/M46I/I54V/L63P/A71V/V82A/L90M | | | |
| 92 | 0.13 | >200 | >1494 |
| 129 | 0.17 | >200 | >1168 |
| 122 | 0.61 | >200 | >327 |

TABLE 2-continued

Activity against drug resistant HIV mutants.

| Compound No. | EC$_{50}$ (μM) | IC$_{50}$ (μM) | TI |
|---|---|---|---|
| 94 | 0.72 | >200 | >276 |
| 100 | 2.7 | 173 | 64 |
| 127 | 1.6 | >200 | >129 |
| 128 | 3.5 | 169 | 49 |
| AZT | 1.3 | >200 | >153 |
| HIV-1 1026040: mutation V32I/M46I/L63P/L90M | | | |
| 92 | 80.5 | >200 | >2.5 |
| 129 | 4 | >200 | >51 |
| 122 | 4 | >200 | >51 |
| 94 | 3.7 | >200 | >55 |
| 100 | 0.4 | 56 | 148 |
| 127 | 0.1 | >200 | >2000 |
| 128 | 2.5 | >200 | >80 |
| AZT | 0.006 | >1 | >167 |

3. Example 22

Activity Against Different Retroviruses

The highly conserved zinc finger motif is considered an appealing antiviral target in part because a compound targeting this protein is likely to be active against a wide variety of viruses. The compounds of the present invention often exhibit broad spectrum antiviral activity, which is attributed to their mode of action. Table 3 shows the activity of selected compounds of the present invention against HIV-1, HIV-2, and SIV to demonstrate this feature, using the same XTT cytoprotection assay described above.

TABLE 3

Activity against HIV-1, HIV-2, and SIV.

| Compound Number | EC$_{50}$ (μM) | IC$_{50}$ (μM) | Therapeutic Index |
|---|---|---|---|
| HIV-1 (RoJo/PBMCs) | | | |
| 92 | 1.9 | >200 | >105 |
| 94 | 2.7 | >200 | >73 |
| 100 | 0.75 | 173 | 230 |
| 122 | 3.4 | 189 | 56 |
| 127 | 1.1 | >200 | >181 |
| 128 | 0.8 | 169 | 225 |
| 129 | 3.8 | 184 | 48 |
| AZT | 0.01 | >4 | >400 |
| HIV-2 (Rod/CEM-SS) | | | |
| 92 | 0.63 | 105 | 167 |
| 94 | 1.1 | 136 | 122 |
| 100 | 2.7 | 142 | 53 |
| 122 | 0.077 | 37 | 475 |
| 127 | 1.6 | 133 | 84 |
| 128 | 3 | 155 | 53 |
| 129 | 0.104 | 6.54 | 63 |
| AZT | 0.017 | >1 | >61 |
| SIV (Mac 251) | | | |
| 92 | 0.28 | 32.8 | 118 |
| 94 | 0.58 | 30.8 | 54 |
| 100 | 1 | 41 | 41 |
| 122 | 0.25 | 34.2 | 138 |
| 127 | 4.6 | 42 | 9.1 |
| 128 | 0.98 | 123 | 125 |
| 129 | 0.29 | 21.8 | 76 |
| AZT | 0.02 | >1 | >40 |

4. Example 23

Activity in Other in vitro Assays

The compounds tested did not inhibit HIV-1 integrase, reverse transcriptase or protease enzyme activities. Assays for activity against HIV-1 reverse transcriptase rAdT (template/primer) and rCdG (template/primer) using recombinant HIV-1 reverse transcriptase were performed as described by Rice (1997) Antimicrob. Agents & Chemother. 41: 419-426. Substrate cleavage of recombinant HIV-1 protease in the presence of test compounds using an nuclear magnetic resonance-based methodology with the artificial substrate Ala-Ser-Glu-Asn-Trp-Pro-Ile-Val-amide (Multiple Peptide Systems, San Diego, Calif.) was performed as described by Rice (1997) supra. The ability of recombinant HIV-1 integrase to carry out 3' processing and strand transfer activities in the presence of test compounds was performed as described by Buckheit (1994) AIDS Res. & Human Retroviruses 10: 1497-1506, and Turpin (1998) Antimicrob. Agents & Chemother. 42: 487-494.

5. Example 24

Relative Rates of Hydrolysis

One of the advantages of the compounds of the present invention over previously identified antiretroviral agents is their increased hydrolytic stability, which improves their biological activity and reduces the amount of compound that must be delivered to a treated subject to produce the desired effect. The following Table shows half-lives in minutes for selected compounds of the present invention in a hydrolysis assay, using the p24 inhibition ELISA assay and the HIV transgenic mouse model spleen cells. A PATE compound having the following structure is included:

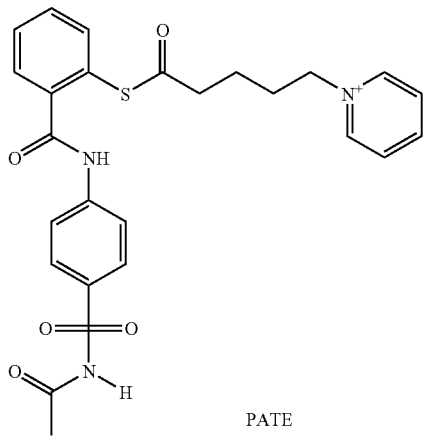

PATE

TABLE 4

Relative rates of hydrolysis of compounds of the present invention.

| Compound Number | $EC_{50}$ (μM) | $IC_{50}$ (μM) | Therapeutic Index | Half-life for hydrolysis (in min.) |
|---|---|---|---|---|
| 11 | 3.6 | >250 | >69 | 244 |
| 12 | 3.5 | 136 | 39 | 465 |
| 22 | 2.6 | 59 | 23 | 408 |
| 23 | 2.2 | 123 | 56 | >500 |
| 61 | 15.7 | — | — | 421 |
| PATE | 6.2 | >316 | >51 | 165 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A compound of Template III-V:

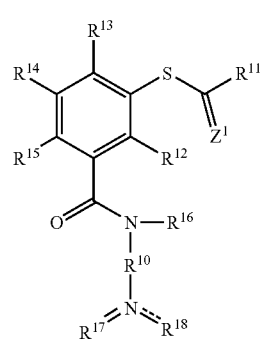

Template III

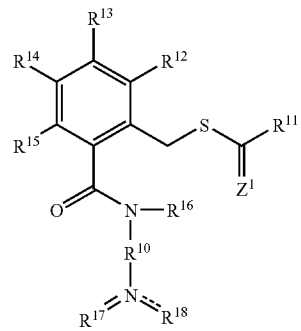

Template IV

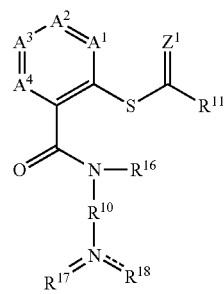

Template V $A^1$, $A^2$, $A^3$, and $A^4$ are each independently selected from the group consisting of CH, $CR^5$, $CR^6$, $CR^7$ and $CR^8$;

$R^5$, $R^6$, $R^7$ and $R^8$ are independently selected from the group consisting of halogen, $CF_3$, alkyl, alkoxy, aryl, $NO_2$, alkylthio, amino, acylamino, arylamino, acylthio, acyl, acyloxy, hydroxy, mercapto, cycloalkyl, heterocycloalkyl, heteroaryl and thioamido; each of which is optionally substituted with a member independently selected from the group consisting of lower alkyl, aryl, acyl, halogen, alkylhalo, hydroxy, amino, alkoxy, alkylamino, acylamino, thioamido, acyloxy, aryloxy, arylamino, aryloxyalkyl, mercapto, thia, aza, oxo, alkoxycarbonyl, alkylaminocarbonyl, saturated and unsaturated cyclic hydrocarbons and heterocycle;

$Z^1$ is a member selected from the group consisting of O, S, and $NR^4$;

R¹¹ is a member selected from the group consisting of alkyl, aryl, arylalkyl, cycloalkyl, cycloatkylallcyl, heterocycloalkyl, and heteroaryl; each of which is optionally substituted with a member independently selected from the group consisting of lower alkyl, aryl, acyl, halogen, alkylhalo, hydroxy, amino, alkoxy, alkylamino, acylamino, thioamido, acyloxy, aryloxy, arylamino, aryloxyalkyl, mercapto, thia, aza, oxo, alkoxycarbonyl, alkylaminocarbonyl, saturated and unsaturated cyclic hydrocarbons and heterocycle; and wherein R¹¹ does not contain a cationic group that cannot be neutralized by loss of a proton near physiological pH;

R⁴ is a member selected from the group consisting of H, alkyl, ailcoxy, aryl, and acyl; each of which is optionally substituted with a member independently selected from the group consisting of lower alkyl, aryl, acyl, halogen, alkylhalo, hydroxy, amino, alkoxy, alkylamino, acylamino, thioamido, acyloxy, aryloxy, arylamino, aryloxyalkyl, mercapto, thia, aza, oxo, alkoxycarbonyl, alkylaminocarbonyl, saturated and unsaturated cyclic hydrocarbons and heterocycle;

R¹⁶ is H;

R¹⁰ is a member selected from the group consisting of alkylene, alkylene-C(O), phenylene, cycloalkylene, aikylcycloalkylene, cycloalkylenealkyl;

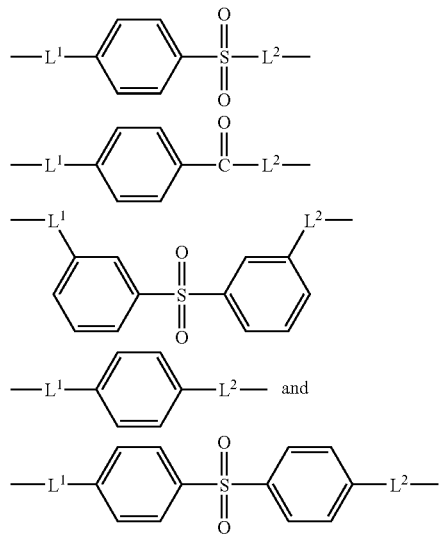

wherein L¹ and L² are members independently selected from the group consisting of a bond and an alkylene chain of up to 4 carbons; each of which is optionally substituted with a member independently selected from the group consisting of lower alkyl, aryl, acyl, halogen, alkylhalo, hydroxy, amino, alkoxy, alkylamino, acylamino, thioamido, acyloxy, aryloxy, arylamino, aryloxyalkyl, mercapto, thia, aza, oxo, alkoxycarbonyl, alkylaminocarbonyl, saturated and unsaturated cyclic hydrocarbons and heterocycle;

R¹⁷ is H;

R¹², R¹³, R¹⁴ and R¹⁵ are members independently selected from the group consisting of H, alkyl, cycloalkyl, heterocycloalkyl, aryl, heteroaryl, alkoxy, alkylamino, arylamino, alkylthio, acyl, acylamino, acyloxy, acylthio, halogen, hydroxy, amino, thioamido, and mercapto; and pharmaceutically acceptable salts thereof.

2. The compound of claim 1, wherein the compound has the formula of Template III.

3. The compound of claim 1, wherein the compound has the formula of Template IV.

4. The compound of claim 1, wherein the compound has the formula of Template V.

5. The compound of claim 4 wherein A³ and A⁴ are CH.

6. The compound of claim 4, wherein A¹ is CR⁵.

7. The compound of claim 4, wherein A¹ is CH.

8. The compound of claim 2 or 4, wherein Z¹ is O.

9. The compound of claim 1, wherein R¹¹ is a member of the group consisting of optionally substituted alkyl and optionally substituted aryl.

10. The compound of claim 1, wherein R¹¹ is optionally substituted aryl.

11. The compound of claim 1, wherein R¹⁰ is optionally substituted alkylene-C(O) or alkylene.

12. The compound of claim 11, wherein the alkylene portion of said optionally substituted alkylene-C(O) or alkylene comprises a chain of up to about 4 carbon atoms.

13. The compound of claim 1, wherein Z¹ is O.

14. The compound of claim 13, wherein R¹⁰ is optionally substituted alkylene-C(O) or alkylene.

15. The compound of claim 14, wherein R¹⁰ is selected from the group consisting of —CH₂—, —CH(Me)—, —CH(CH₂OH)—, —CH₂CH₂—, —CH(Me)CH₂— and —CH₂CH(Me)—, —CH₂—C(O)—, —CH(Me)—C(O)—, —CH(CH₂OH)—C(O)—, —CH₂CH₂—C(O)—, —CH(Me)CH₂—C(O)— and —CH₂CH(Me)—C(O)—.

16. The compound of claim 1, wherein said compound is selected from the group consisting of:

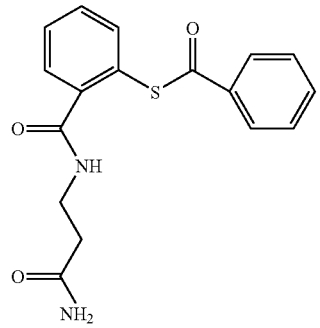

8

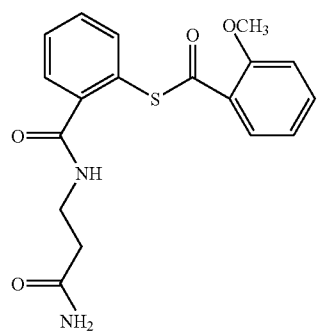

9

-continued
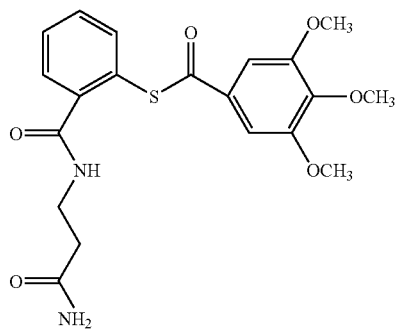
10
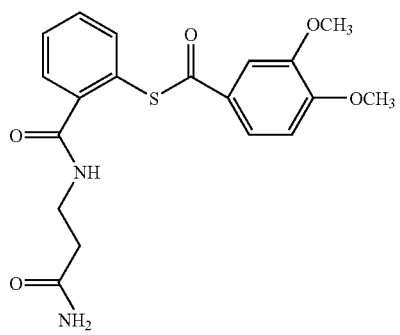
11
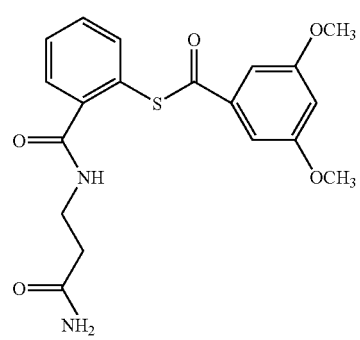
12
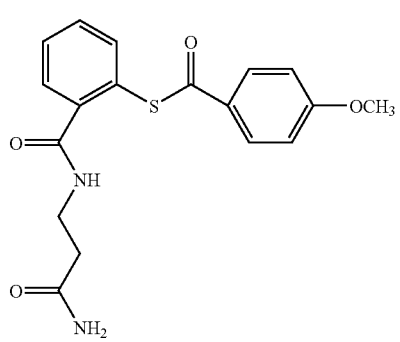
13
-continued
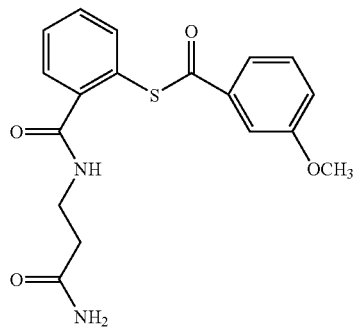
14
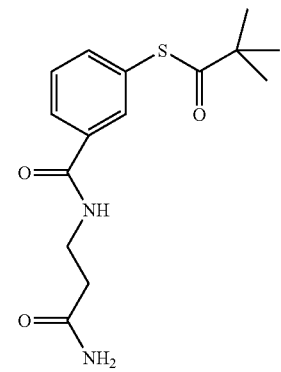
17
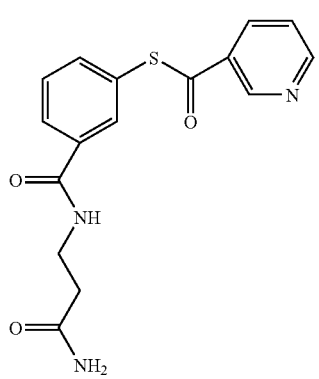
18
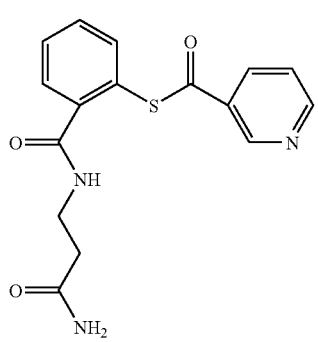
19

-continued
20
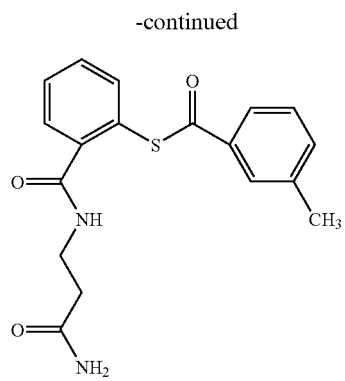
21
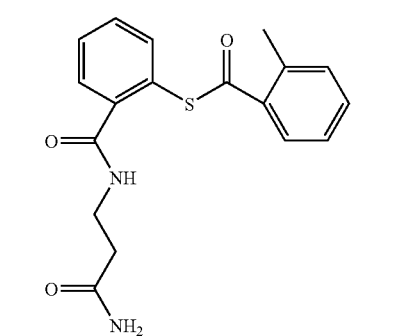
22
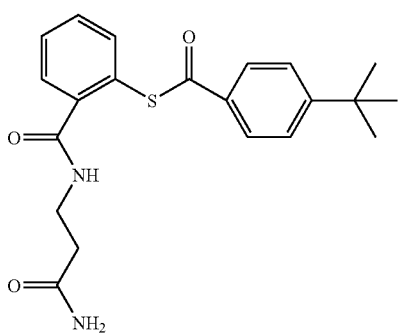
23
-continued
24
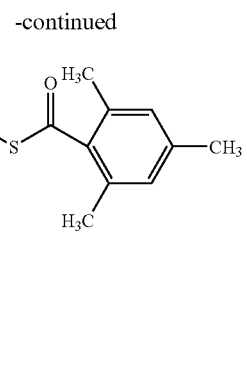
25
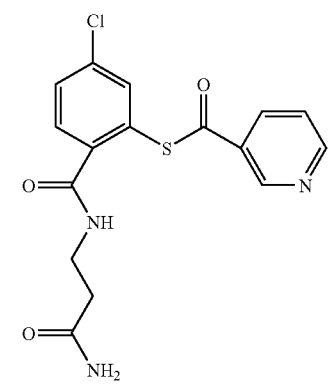
26
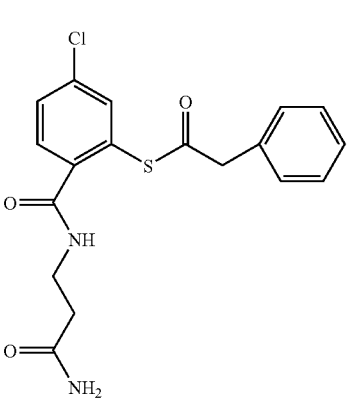
30
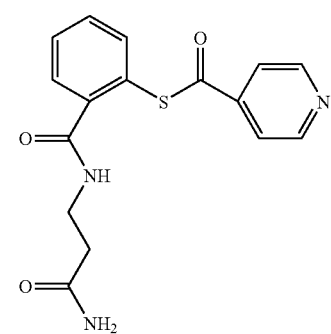

-continued
31
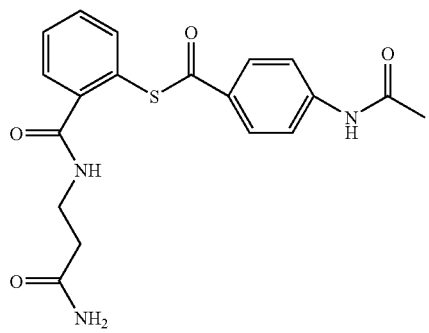
33
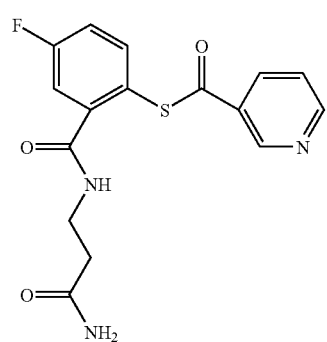
34
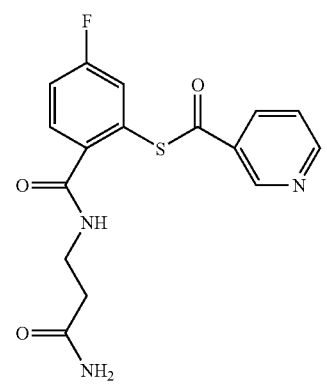
35
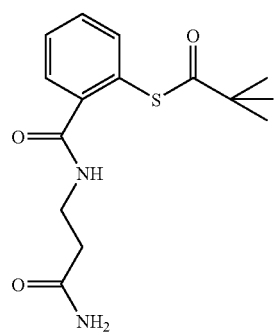
-continued
37
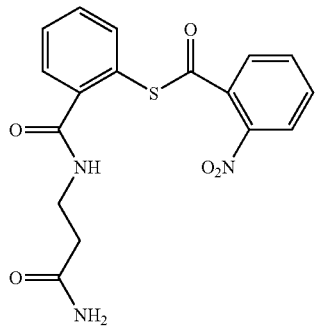
38
39
40
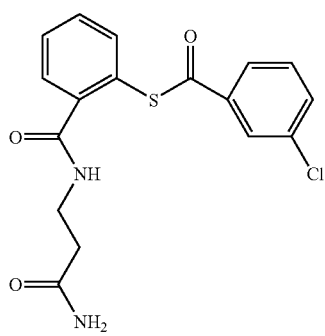

53 54
-continued
48
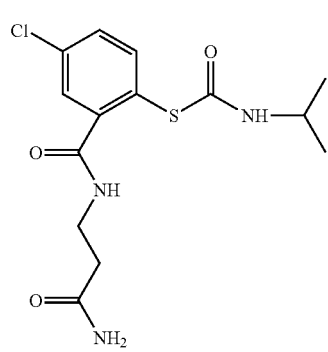
52
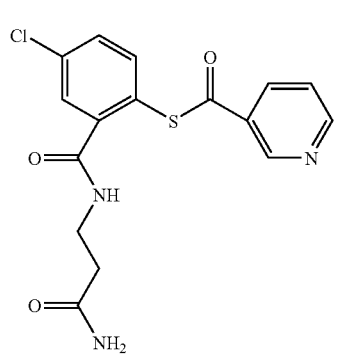
56
57
53
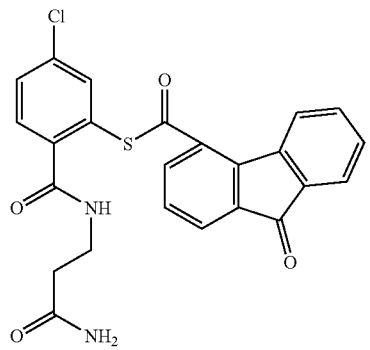
61
55
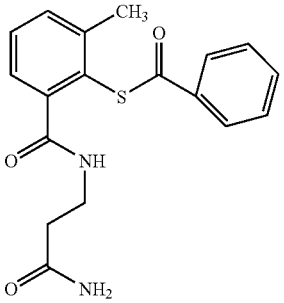
63
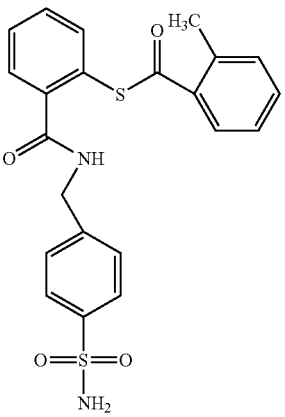

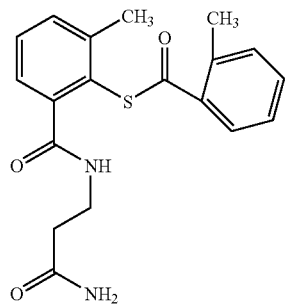
68
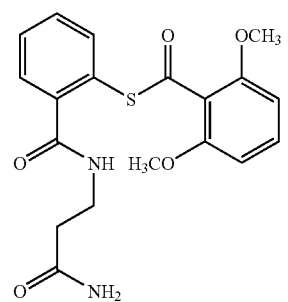
69
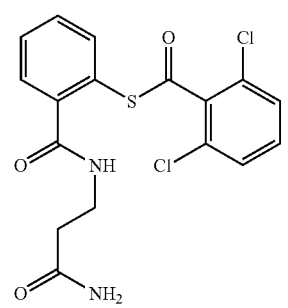
70
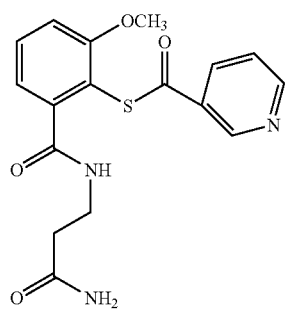
73
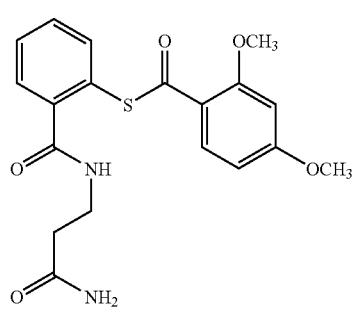
74
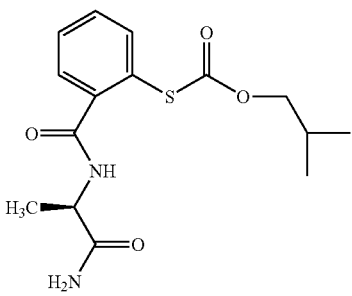
77
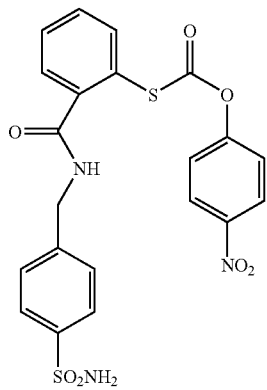
78
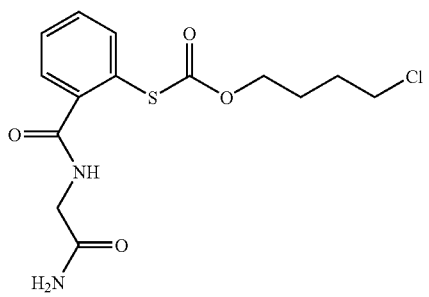
80
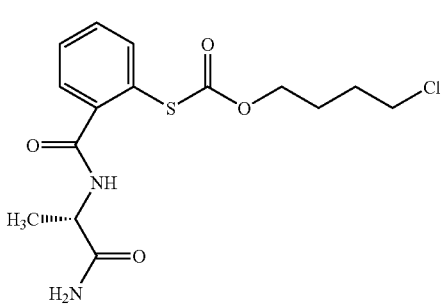
81
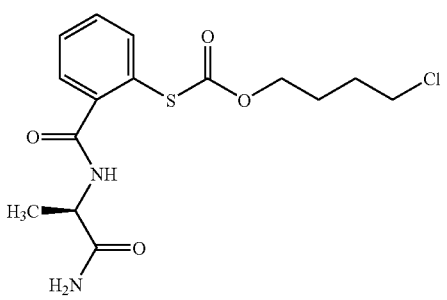
82

83
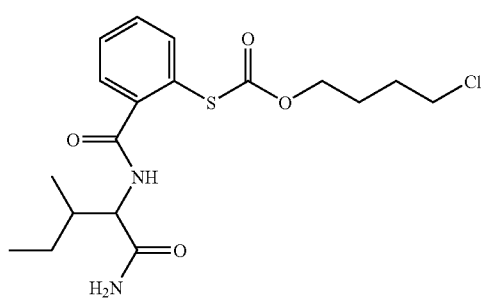
84
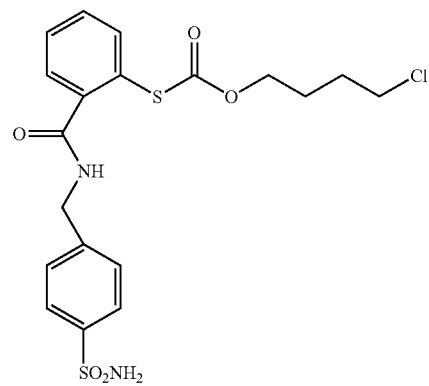
85
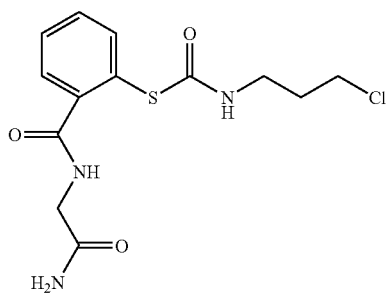
86
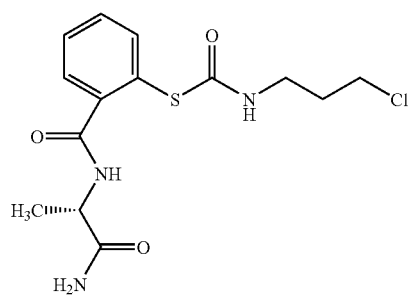
87
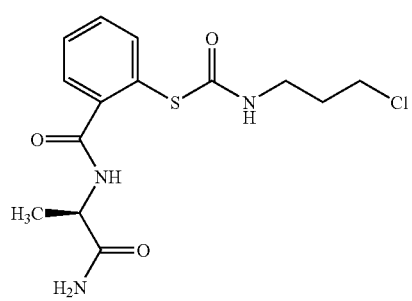
88
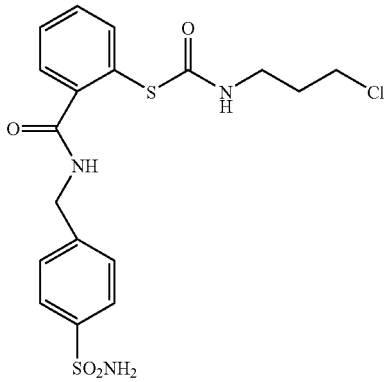
89
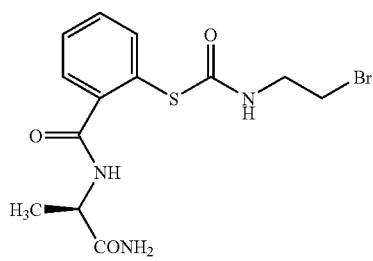
95
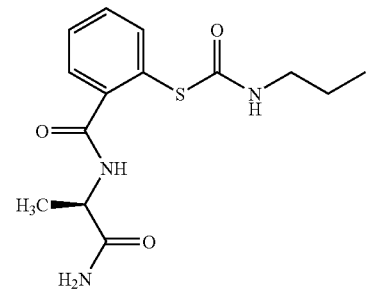
96
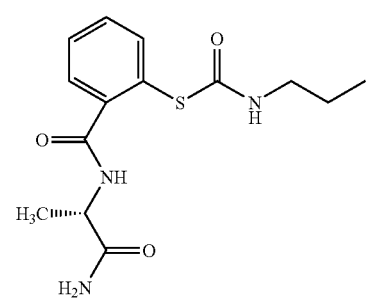
97
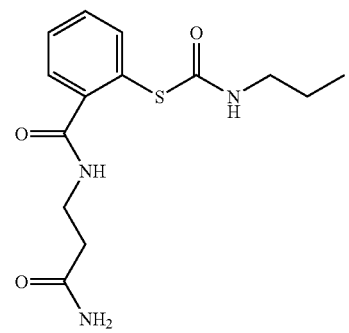

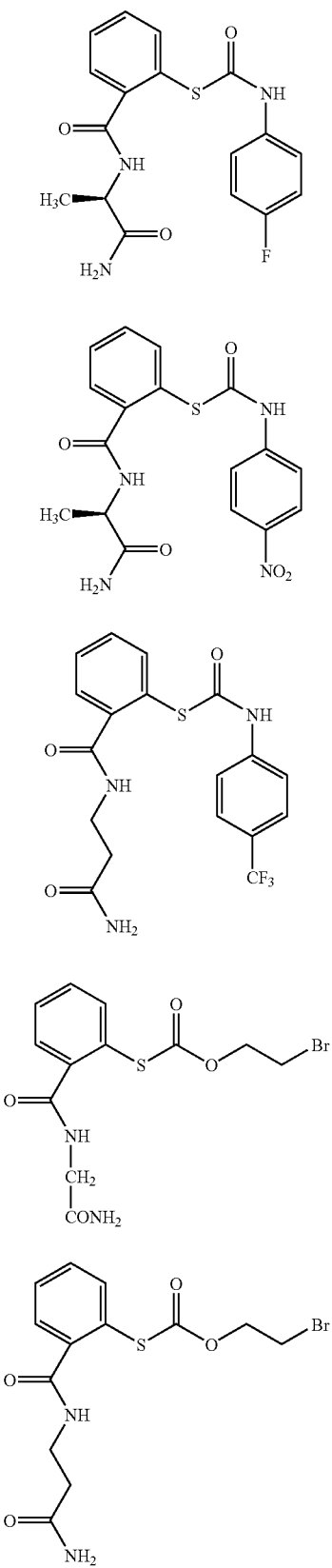
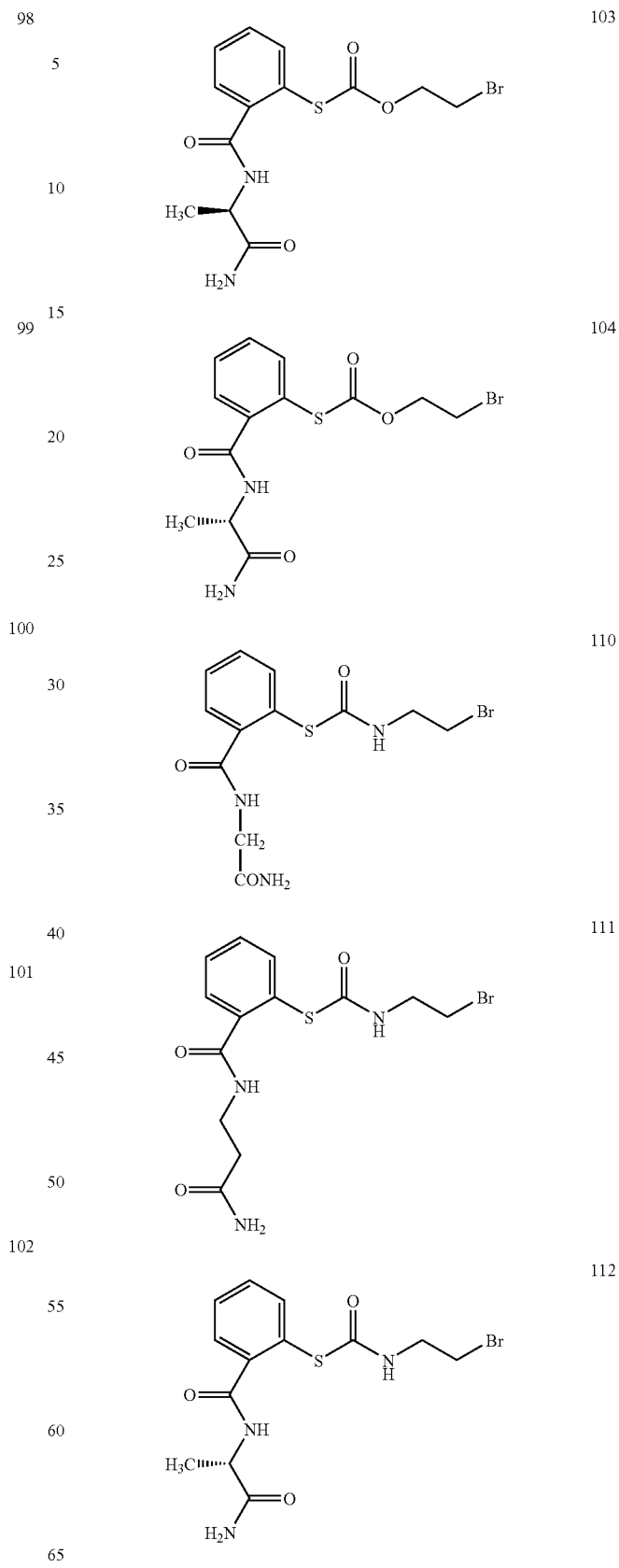

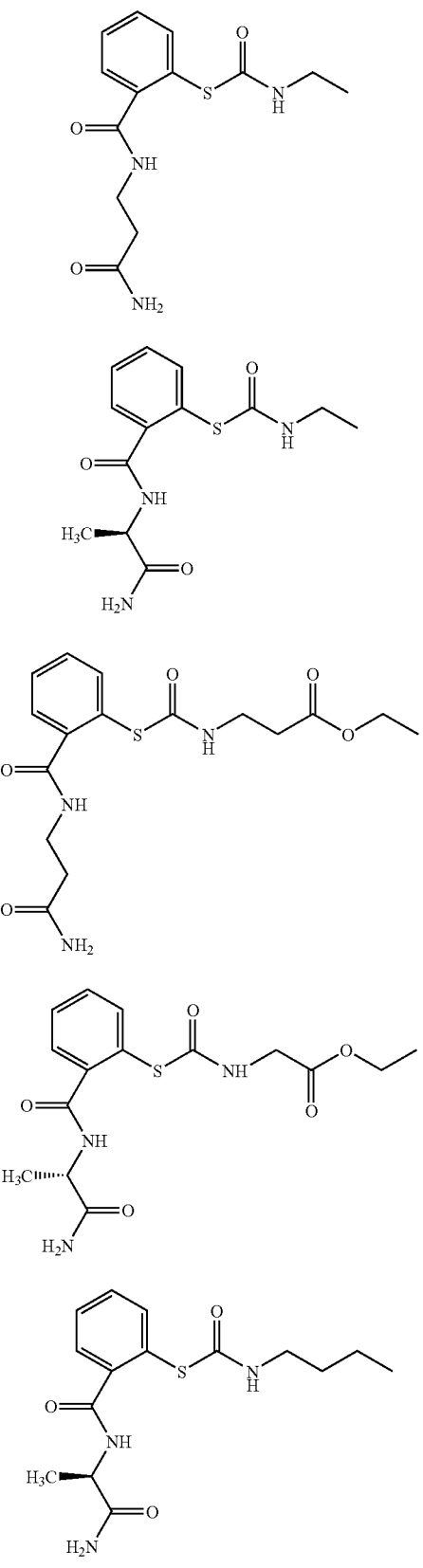

-continued
123
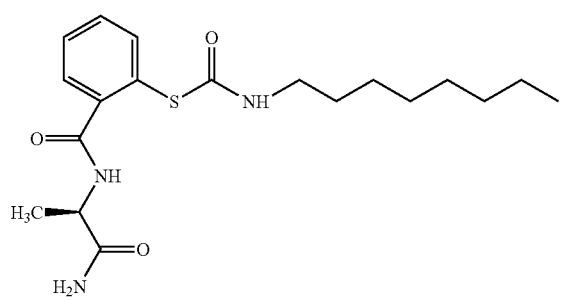
124
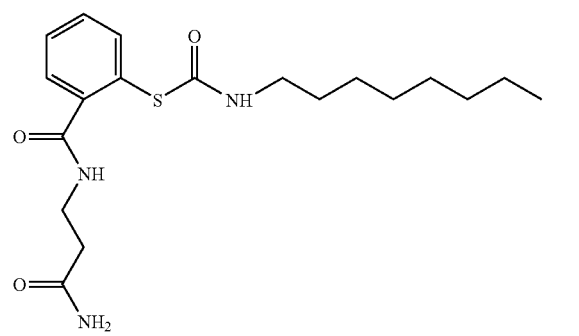
125
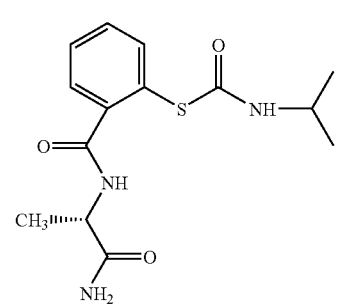
126
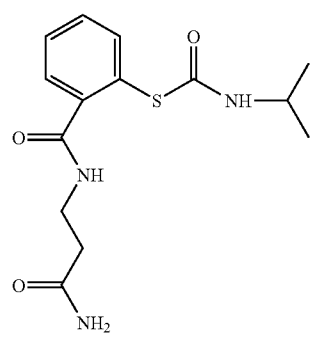
127
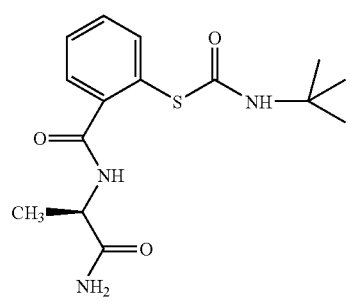
-continued
128
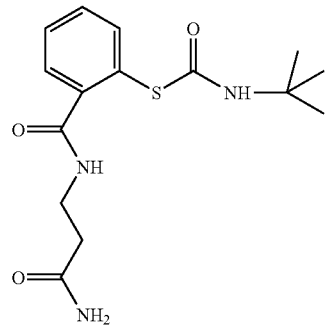
129
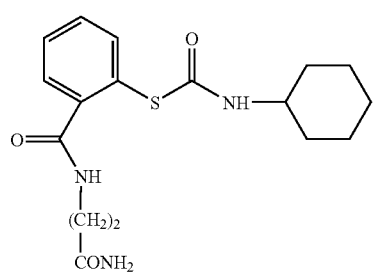
130
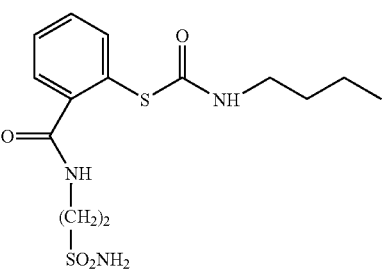
131
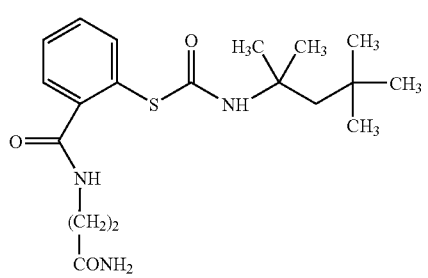
132
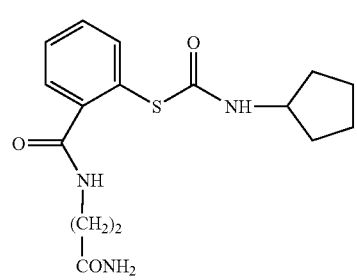

136 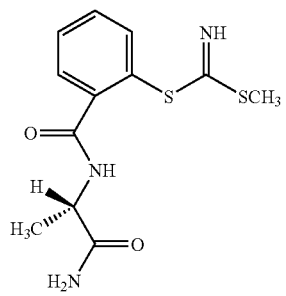
137 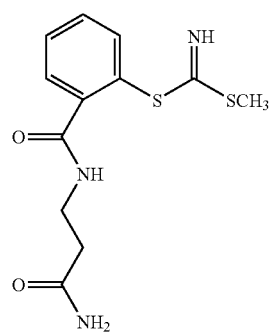
138 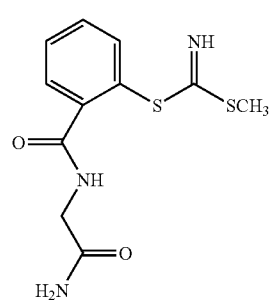
139 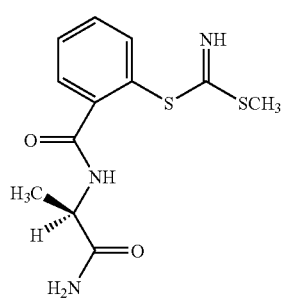
140 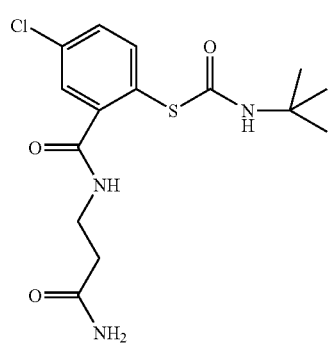
141 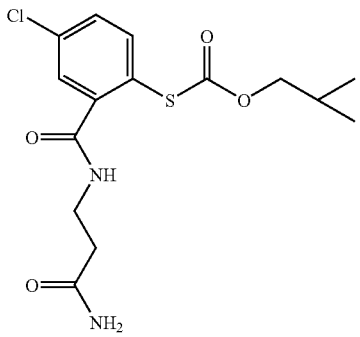
142 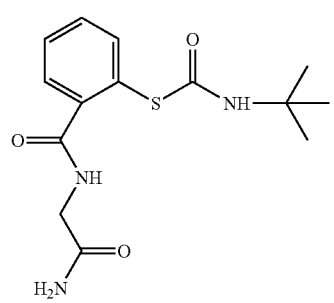
143 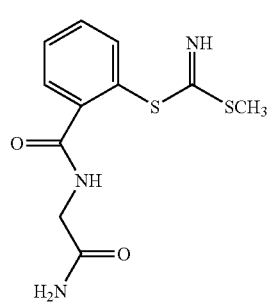
144 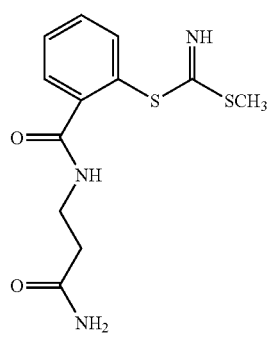
145 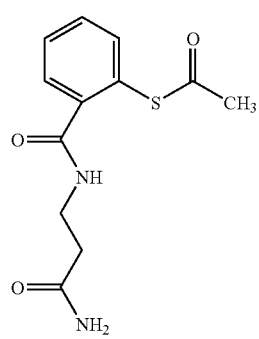

146
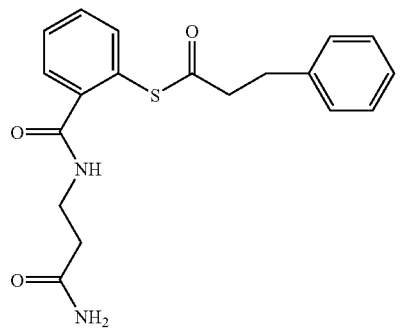
147
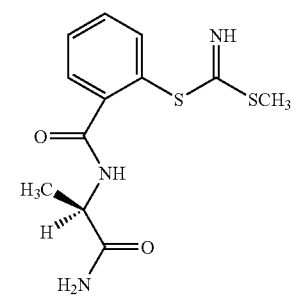
148
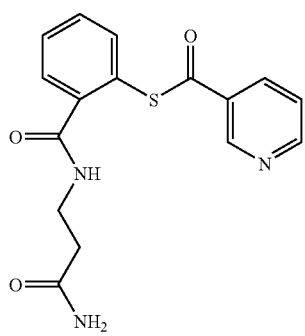
149
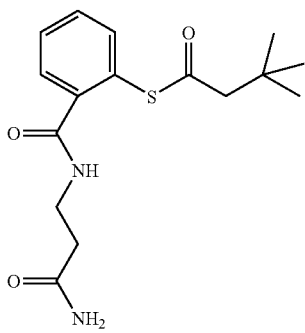
150
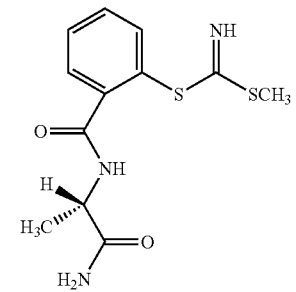
151
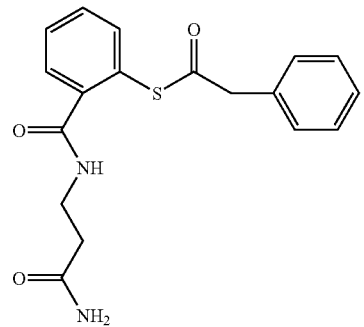
152
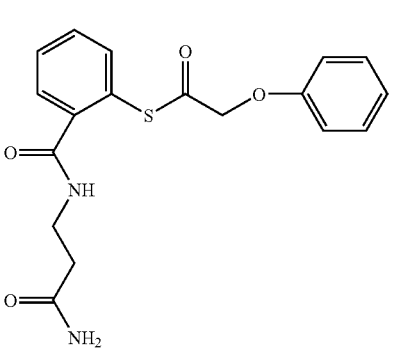
153
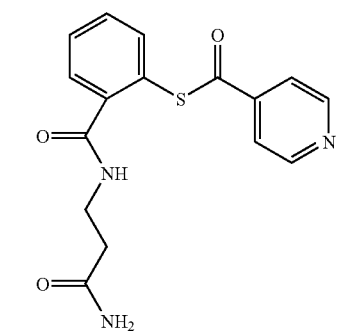
154
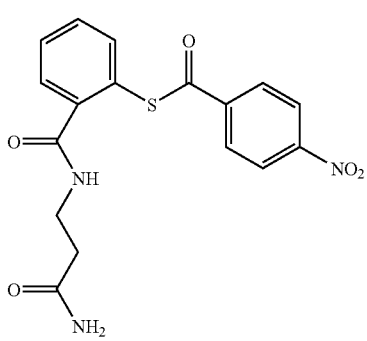

155 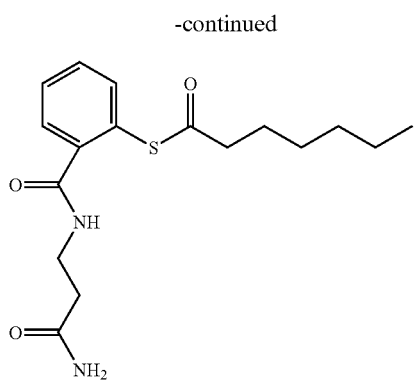
156 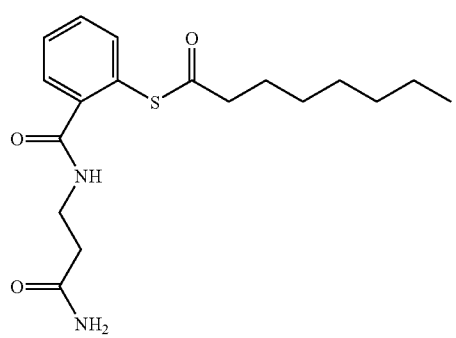
157 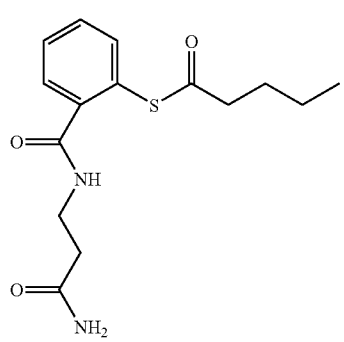
158 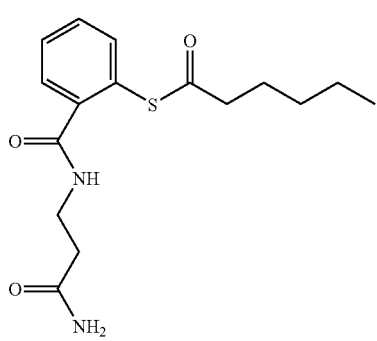
159 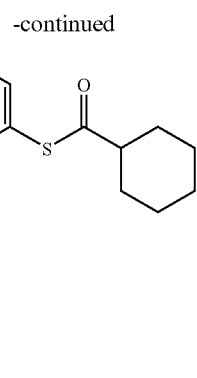
160 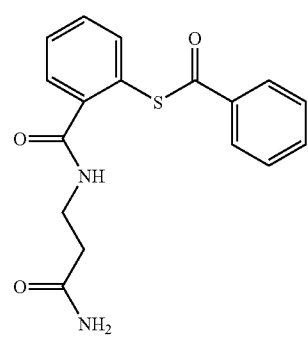
161 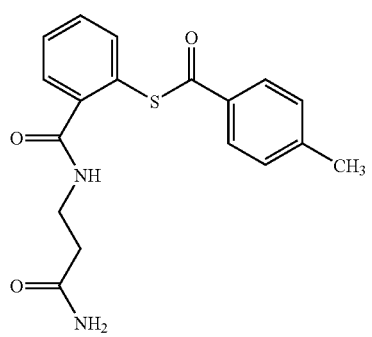
162 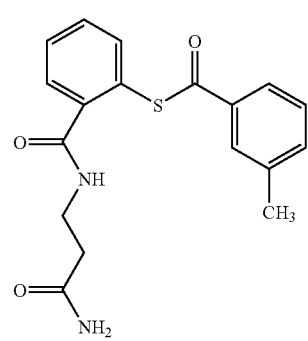

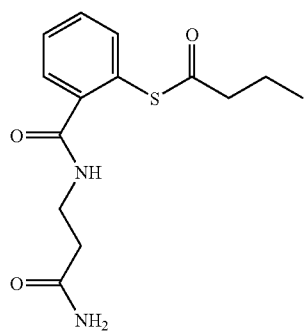
163
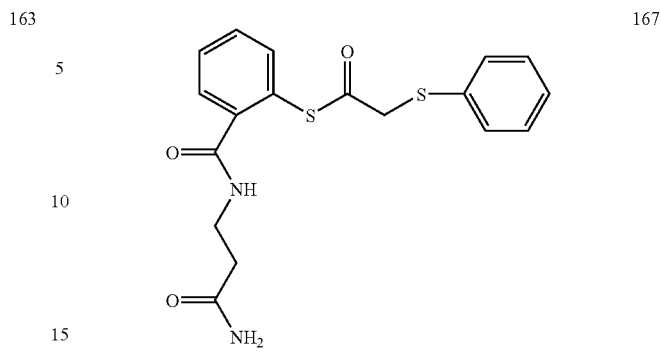
167
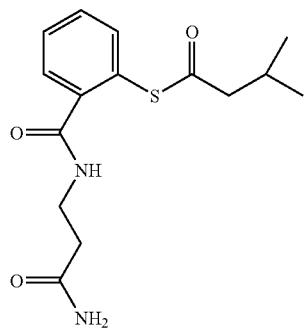
164
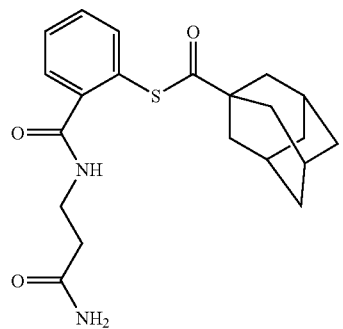
168
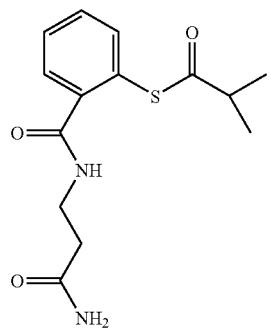
165
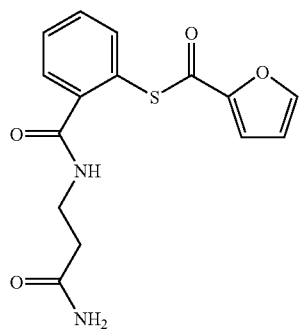
169
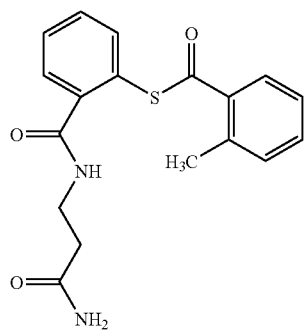
166
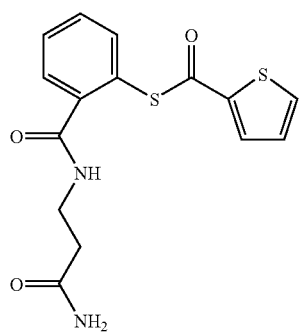
170

-continued
171 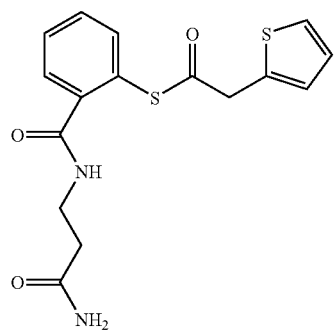
172 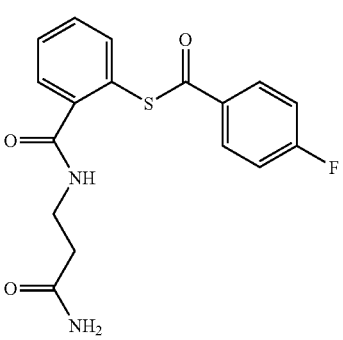
173 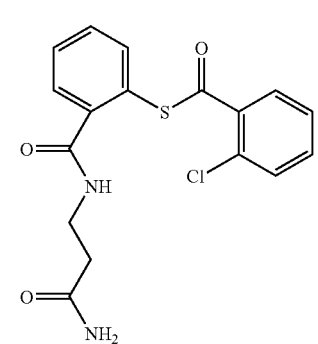
174
-continued
175 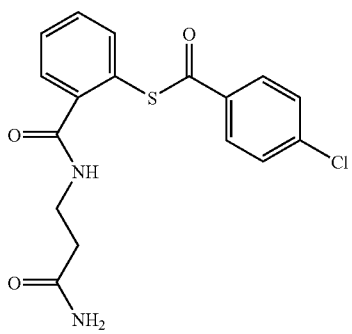
176 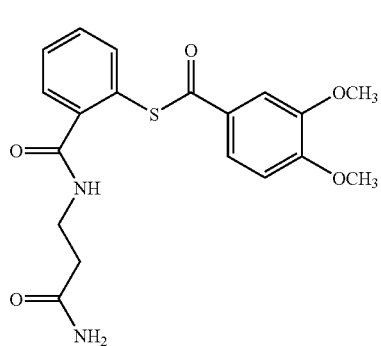
177 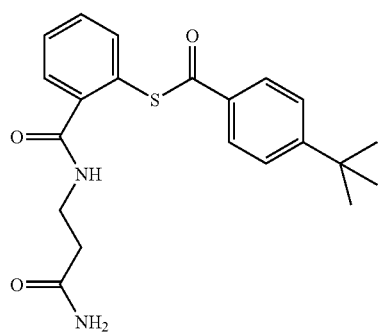
178 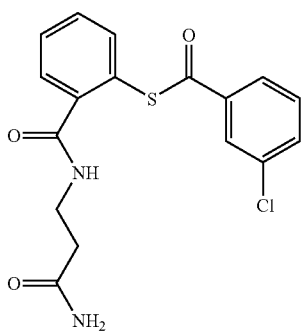

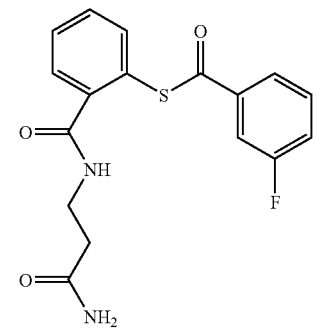
179
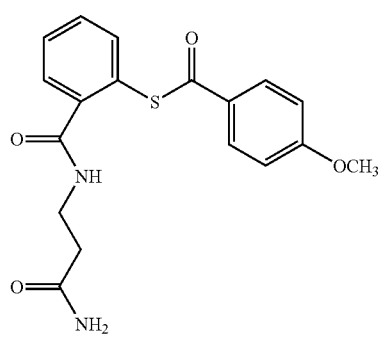
180
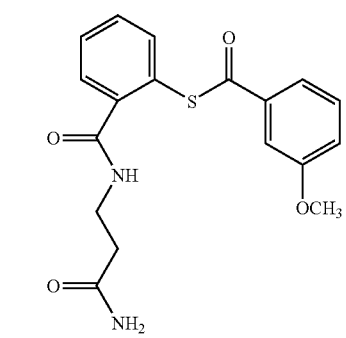
181
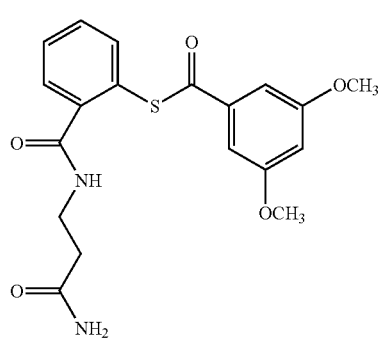
182
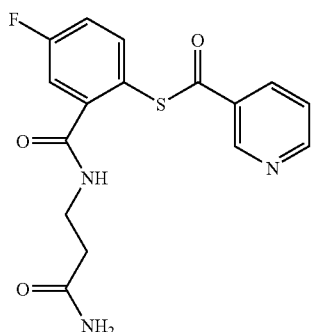
183
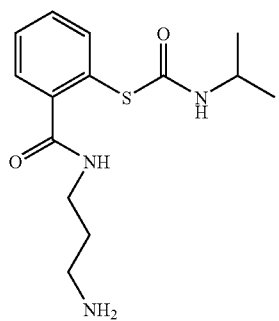
207
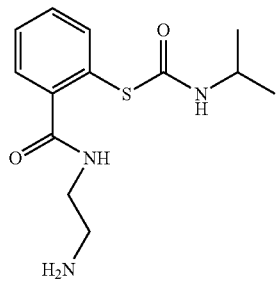
208
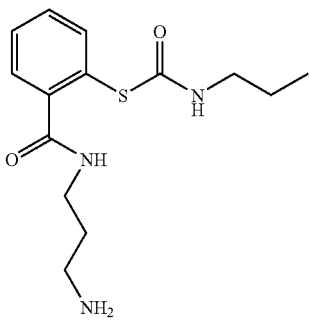
209
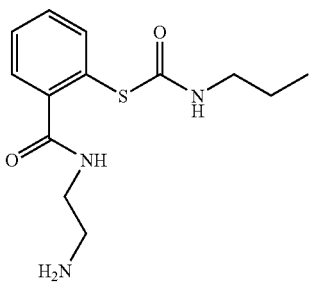
210

-continued
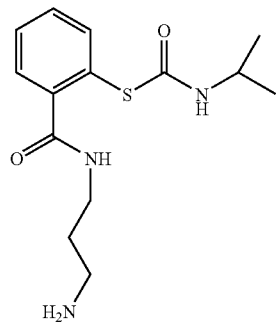 219
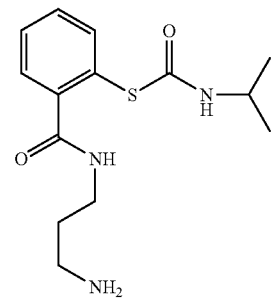 220
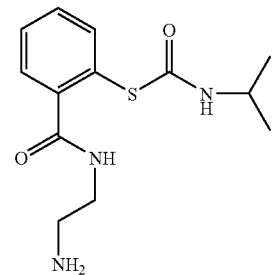 221
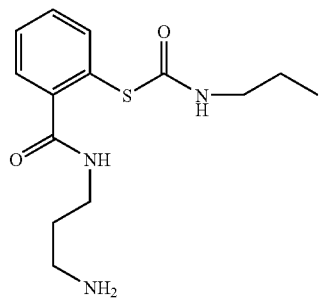 222
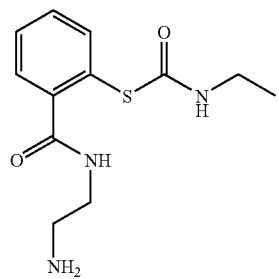 223
-continued
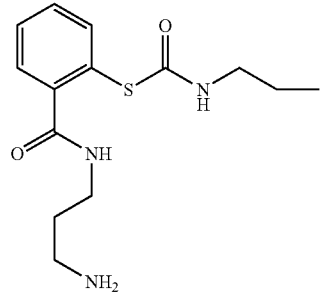 224
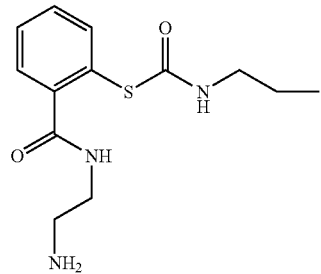 225
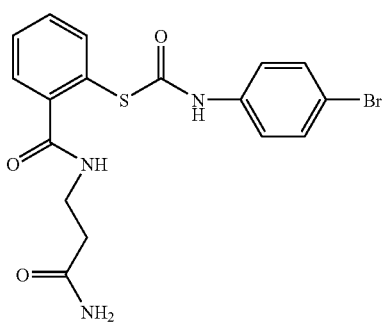 226
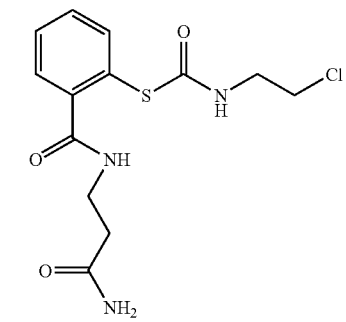 227
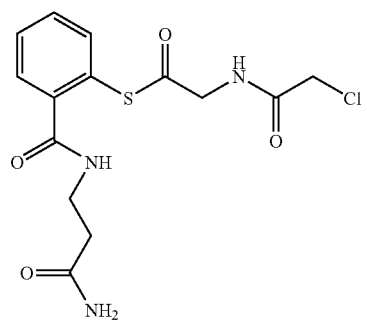 228

-continued

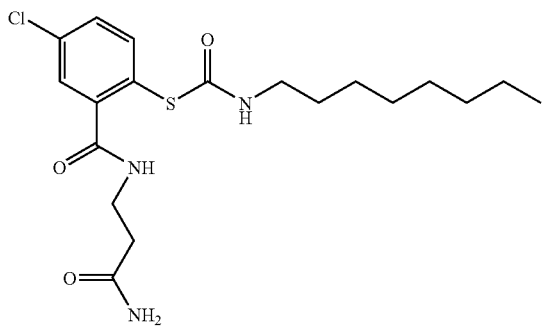

229

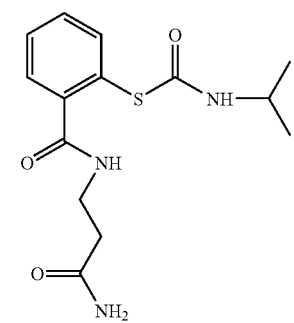

230

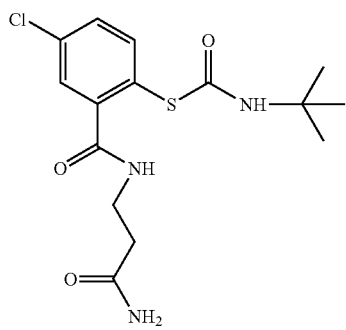

231

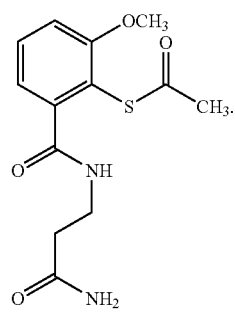

232

17. A composition, said composition comprising a compound of claim 1; or pharmaceutically acceptable salts thereof and an excipient therefor.

18. The composition of claim 17, wherein said excipient includes at least one pharmaceutically acceptable carrier or diluent.

19. The composition of claim 17, further comprising a second anti-retroviral agent.

20. The composition of claim 19, wherein said second anti-retroviral agent is a member selected from the group consisting of a nucleoside analogue, a nucleotide analogue, a reverse transcriptase inhibitor, an integrase inhibitor, a fusion inhibitor and a protease inhibitor.

21. The composition of claim 17, further comprising blood plasma, nutrient media, protein, a pharmaceutical, a cosmetic, a sperm or oocyte preparation, cells, cell cultures, bacteria, viruses, food or drink.

22. The compound of claim 15, wherein $R^{11}$ is an alkyl group.

23. The compound of claim 15, wherein $R^{11}$ is an optionally substituted aromatic group.

24. The compound of claim 23, wherein $R^{11}$ is pyridine.

25. The compound of claim 15, wherein $R^{10}$ is selected from the group consisting of —$CH_2$—C(O)—, —CH(Me)—C(O)— and —$CH_2CH_2$—C(O)—.

26. The compound of claim 15, selected from the group consisting of:

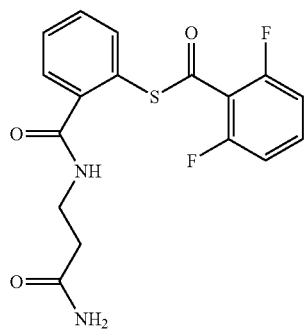

52

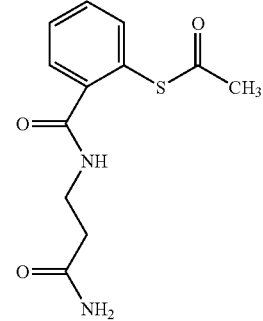

145

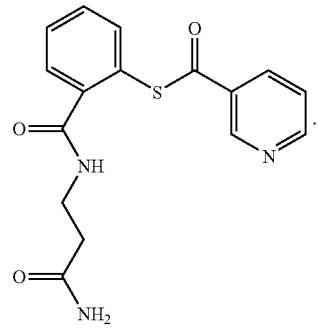

148

* * * * *